(12) United States Patent
Jin et al.

(10) Patent No.: US 6,265,400 B1
(45) Date of Patent: Jul. 24, 2001

(54) CYCLIC CARBAMATES AND ISOXAZOLIDINES AS IIB/IIIA ANTAGONISTS

(75) Inventors: Fuqiang Jin, Wilmington; Pasquale Nicholas Confalone, Greenville, both of DE (US)

(73) Assignee: Dupont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/340,950

(22) Filed: Jun. 28, 1999

Related U.S. Application Data

(60) Provisional application No. 60/091,030, filed on Jun. 29, 1998.

(51) Int. Cl.[7] .................. C07D 261/02; C07D 265/10; C07D 413/12; A61K 31/42; A61P 7/02
(52) U.S. Cl. ........................ 514/228.8; 544/96; 544/97
(58) Field of Search .................. 544/96, 97; 514/228.8

(56) References Cited

U.S. PATENT DOCUMENTS

| | | | |
|---|---|---|---|
| 5,710,159 | 1/1998 | Voss et al. | 514/275 |
| 5,849,736 | 12/1998 | Wityak et al. | 514/227.8 |

FOREIGN PATENT DOCUMENTS

| | | |
|---|---|---|
| 0478328 | 4/1992 | (EP) . |
| 0478363 | 4/1992 | (EP) . |
| 0512831 | 11/1992 | (EP) . |
| 9307867 | 4/1993 | (WO) . |
| 9514682 | 6/1995 | (WO) . |
| 9514683 | 6/1995 | (WO) . |
| 9806694 | 2/1998 | (WO) . |
| 9806707 | 2/1998 | (WO) . |

*Primary Examiner*—Bruck Kifle
*Assistant Examiner*—Hong Liu

(57) ABSTRACT

The present invention relates generally to cyclic carbamates and isoxazolidines or Formula (I)

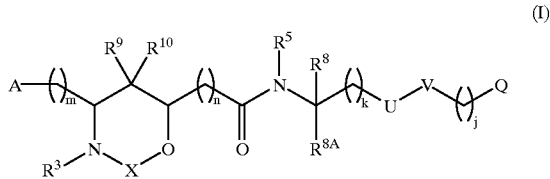

or their pharmaceutically acceptable salts thereof, which are useful as antagonists of the platelet glycoprotein IIb/IIIa fibrinogen receptor complex, to pharmaceutical compositions containing such compounds, processes for preparing such compounds, and to methods of using these compounds for the inhibition of platelet aggregation, as thrombolytics, and/or for the treatment of thromboembolic disorders.

28 Claims, No Drawings

CYCLIC CARBAMATES AND ISOXAZOLIDINES AS IIB/IIIA ANTAGONISTS

This application claims the benefit of U.S. Provisional Application No. 60/091,030, filed Jun. 29, 1998.

FIELD OF THE INVENTION

The present invention relates generally to cyclic carbamates and isoxazolidines which are useful as antagonists of the platelet glycoprotein IIb/IIIa fibrinogen receptor complex, to pharmaceutical compositions containing such compounds, processes for preparing such compounds, and to methods of using these compounds for the inhibition of platelet aggregation, as thrombolytics, and/or for the treatment of thromboembolic disorders.

BACKGROUND OF THE INVENTION

Hemostasis is the normal physiological process in which bleeding from an injured blood vessel is arrested. It is a dynamic and complex process in which platelets play a key role. Within seconds of vessel injury, resting platelets become activated and are bound to the exposed matrix of the injured area by a phenomenon called platelet adhesion. Activated platelets also bind to each other in a process called platelet aggregation to form a platelet plug. The platelet plug can stop bleeding quickly, but it must be reinforced by fibrin for long-term effectiveness, until the vessel injury can be permanently repaired.

Thrombosis may be regarded as the pathological condition wherein improper activity of the hemostatic mechanism results in intravascular thrombus formation. Activation of platelets and the resulting platelet aggregation and platelet factor secretion has been associated with a variety of pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury.

Platelets are activated by a wide variety of agonists resulting in platelet shape change, secretion of granular contents and aggregation. Aggregation of platelets serves to further focus clot formation by concentrating activated clotting factors at the site of injury. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely platelet glycoprotein IIb/IIIa complex (GPIIb/IIIa), which is the membrane protein mediating platelet aggregation. A recent review of GPIIb/IIIa is provided by Phillips et al. *Cell* (1991) 65: 359–362. The development of a GPIIb/IIIa antagonist represents a promising new approach for antiplatelet therapy.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

Several RGD-peptidomimetic compounds have been reported which block fibrinogen binding and prevent the formation of platelet thrombi.

European Patent Application Publication Number 478363 relates to compounds having the general formula:

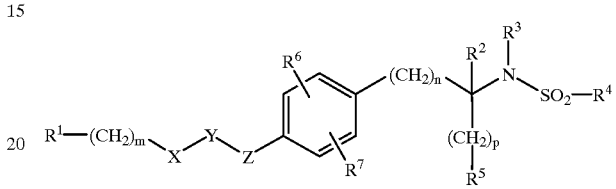

European Patent Application Publication Number 478328 relates to compounds having the general formula:

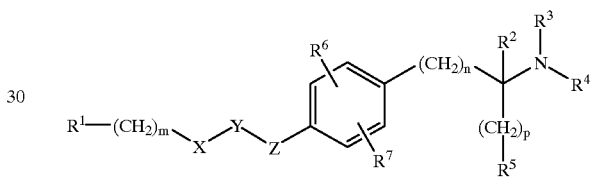

European Patent Application Publication Number 525629 (corresponds to Canadian Patent Application Publication Number 2,074,685) discloses compounds having the general formula:

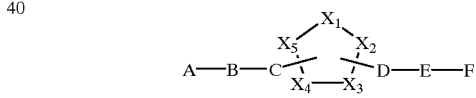

PCT Patent Application 9307867 relates to compounds having the general formula:

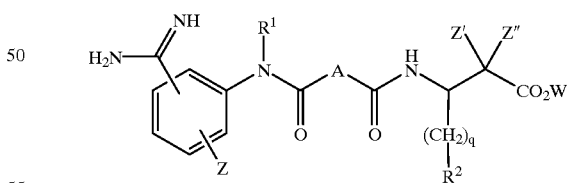

European Patent Application Publication Number 4512831 relates to compounds having the general formula:

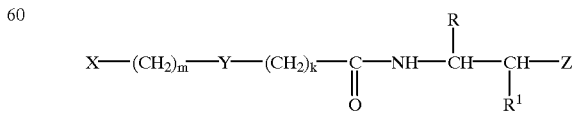

Copending commonly assigned U.S. patent application (U.S. Ser. No. 08/337,920, filed Nov. 10, 1994, Wityak et al.;

published as WO95/13155, Jun. 1, 1995) discloses compounds having the general formula:

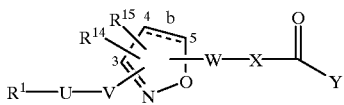

which are useful as IIB/IIIA antagonists.

Copending commonly assigned U.S. patent application (U.S. Ser. No. 08/455,768, filed May 31, 1995, Voss et al.) discloses compounds having the general formula:

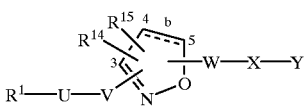

which are useful as $a_v b_3$ antagonists.

None of the above references teaches or suggests the compounds of the present invention which are described in detail below.

SUMMARY OF THE INVENTION

One aspect of this invention provides novel compounds of Formula (I) (described below) which are useful as antagonists of the platelet glycoprotein IIb/IIIa complex. The compounds of the present invention inhibit the binding of fibrinogen to platelet glycoprotein IIb/IIIa complex and inhibit the aggregation of platelets. The present invention also includes pharmaceutical compositions containing such compounds of Formula (I), and methods of using such compounds for the inhibition of platelet aggregation, as thrombolytics, and/or for the treatment of thromboembolic disorders.

The present invention also includes methods of treating cardiovascular disease, thrombosis or harmful platelet aggregation, reocclusion following thrombolysis, reperfusion injury, or restenosis by administering a compound of Formula (I) alone or in combination with one or more additional therapeutic agents selected from: anti-coagulants such as warfarin or heparin; anti-platelet agents such as aspirin, piroxicam or ticlopidine; thrombin inhibitors such as boroarginine derivatives, hirudin or argatroban; or thrombolytic agents such as tissue plasminogen activator, anistreplase, urokinase or streptokinase; or combinations thereof.

Also included in the present invention are pharmaceutical kits comprising one or more containers containing pharmaceutical dosage units comprising a compound of Formula (I), for the treatment of cell adhesion related disorders, including but not limited to thromboembolic disorders.

DETAILED DESCRIPTION OF THE INVENTION

This invention relates to novel compounds the Formula (I):

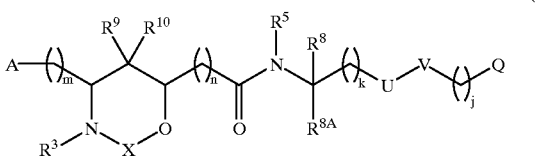

or their pharmaceutically acceptable salts thereof, wherein:

A is selected from $R^1$;
  phenyl substituted with $R^1$ and 0–2 $R^6$;
  piperidinyl substituted with 0–1 $R^1$ and 0–2 $R^6$; and
  pyridyl substituted with 0–1 $R^1$ and 0–2 $R^6$;

$R^1$ is —$NHR^2$, —$C(=NR^2)NHR^2$, —$Z(CH_2)_q NHR^2$, —$Z(CH_2)_q C(=NR^2)NHR^2$, —$N(R^2)C(=NR^2)NHR^2$, —$C(=O)NHR^2$, —$C(=NR^2)N(OR^2A)R^2$, or —$C(=NOR^{2A})NHR^2$;

q is 1, 2, or 3;

Z is a bond, O, S, S(=O), or S(=O)$_2$;

$R^2$ is, independently at each occurence, H, $C_1$–$C_4$ alkyl, $C_2$–$C_6$ alkenyl, $C_1$–$C_{10}$ alkoxycarbonyl, or aryl($C_1$–$C_{10}$ alkoxy)carbonyl;

$R^{2A}$ is H or $C_1$–$C_{10}$ alkyl substituted with 0–1 $R^4$;

$R^3$ is H,
  $C_1$–$C_6$ alkyl substituted with 0–1 $R^6$,
  $C_2$–$C_6$ alkenyl substituted with 0–1 $R^6$,
  $C_2$–$C_6$ alkynyl substituted with 0–1 $R^6$,
  $C_3$–$C_7$ cycloalkyl substituted with 0–2 $R^{6A}$,
  phenyl substituted with 0–2 $R^{6A}$, or
  pyridyl substituted with 0–2 $R^{6A}$;

X is —C(=O)— or a single bond;

$R^4$ is $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $C_1$–$C_6$ alkylcarbonyl, $C_6$–$C_{10}$ aryl, —$N(R^{12})R^{13}$; halo, $CF_3$, CN, $NO_2$, $C_1$–$C_6$ alkoxycarbonyl, carboxy, piperidinyl, morpholinyl, or pyridinyl;

$R^5$ is H or $C_1$–$C_{10}$ alkyl substituted with 0–1 $R^4$;

$R^6$ is $C_3$–$C_7$ cycloalkyl substituted with 0–2 $R^{6A}$ or 0–1 $R^1$;
  phenyl substituted with 0–2 $R^{6A}$ or 0–1 $R^1$; or
  pyridyl substituted with 0–2 $R^{6A}$ or 0–1 $R^1$;

$R^{6A}$ is $C_1$–$C_4$ alkyl, $C_1$–$C_4$ alkoxy, halo, $CF_3$, $NO_2$ or $NR^{12}R^{13}$;

U is —$C(R^7)(R^{7A})$— or —$N(R^7)$—;

$R^7$ is selected from:
  H,
  $C_1$–$C_4$ alkyl substituted with 0–2 $R^{16}$,
  $C_2$–$C_4$ alkenyl substituted with 0–2 $R^{16}$,
  $C_2$–$C_4$ alkynyl substituted with 0–2 $R^{16}$,
  $C_3$–$C_6$ cycloalkyl substituted with 0–2 $R^{16}$,
  $C_3$–$C_6$ cycloalkyl($C_1$–$C_4$ alkyl) substituted with 0–2 $R^{16}$,
  aryl substituted with 0–4 $R^{16}$,
  aryl($C_1$–$C_4$ alkyl) substituted with 0–4 $R^{16}$,
  a 5–6 membered heterocyclic ring system having 1–3 heteroatoms selected independently from O,S, and N. said heterocyclic ring being substituted with 0–4 $R^{16}$, and
  $C_1$–$C_4$ alkyl substituted with a 5–6 membered heterocyclic ring system having 1–3 heteroatoms selected independently from O,S, and N, said heterocyclic ring being substituted with 0–4 $R^{16}$;

alternatively, $R^5$ and $R^7$ are taken together to form a 5–6 membered heterocyclic ring system having 1 or 2 nitrogen atoms;

$R^{7A}$ is selected from:
  H,
  $C_1$–$C_4$ alkyl substituted with 0–2 $R^{16}$,
  $C_2$–$C_4$ alkenyl substituted with 0–2 $R^{16}$, and
  $C_2$–$C_4$ alkynyl substituted with 0–2 $R^{16}$;

$R^8$ is selected from:
  H,
  —C(=O)N($R^{20}$)$_2$,
  $C_1$–$C_6$ alkyl substituted with 0–2 $R^{16}$,
  $C_2$–$C_4$ alkenyl substituted with 0–2 $R^{16}$,
  $C_2$–$C_4$ alkynyl substituted with 0–2 $R^{16}$,
  $C_3$–$C_6$ cycloalkyl substituted with 0–2 $R^{16}$,
  aryl substituted with 0–4 $R^{16}$,
  aryl($C_1$–$C_4$ alkyl) substituted with 0–4 $R^{16}$,
  a 5–6 membered heterocyclic ring system having 1–3 heteroatoms selected independently from O,S, and N, said heterocyclic ring being substituted with 0–4 $R^{16}$, and
  $C_1$–$C_4$ alkyl substituted with a 5–10 membered heterocyclic ring system having 1–3 heteroatoms selected independently from O,S, and N, said heterocyclic ring being substituted with 0–4 $R^{16}$;

alternatively, $R^5$ and $R^8$ are taken together to form a piperidinyl or a pyrrolidinyl ring;

alternatively, $R^7$ and $R^8$ are taken together to form a 5–6 membered carbocyclic ring, wherein said carbocyclic ring is either saturated, partially unsaturated or aromatic;

$R^{8A}$ is selected from:
  H,
  $C_1$–$C_4$ alkyl substituted with 0–2 $R^{16}$,
  $C_2$–$C_4$ alkenyl substituted with 0–2 $R^{16}$, and
  $C_2$–$C_4$ alkynyl substituted with 0–2 $R^{16}$;

k is 0 or 1;
j is 0, 1, 2, or 3;
V is O, NH, or a single bond;
Q is —C(=O)Y, —SO$_3$H, or —PO$_3$H;
Y is hydroxy,
  $C_1$–$C_{10}$ alkyloxy,
  $C_3$–$C_{11}$ cycloalkyloxy,
  $C_6$–$C_{10}$ aryloxy,
  $C_7$–$C_{11}$ aralkyloxy,
  $C_3$–$C_{10}$ alkylcarbonyloxyalkyloxy,
  $C_3$–$C_{10}$ alkoxycarbonyloxyalkyloxy,
  $C_2$–$C_{10}$ alkoxycarbonylalkyloxy,
  $C_5$–$C_{10}$ cycloalkylcarbonyloxyalkyloxy,
  $C_5$–$C_{10}$ cycloalkoxycarbonyloxyalkyloxy,
  $C_5$–$C_{10}$ cycloalkoxycarbonylalkyloxy,
  $C_7$–$C_{11}$ aryloxycarbonylalkyloxy,
  $C_8$–$C_{12}$ aryloxycarbonyloxyalkyloxy,
  $C_8$–$C_{12}$ arylcarbonyloxyalkyloxy,
  $C_5$–$C_{10}$ alkoxyalkylcarbonyloxyalkyloxy,
  $C_5$–$C_{10}$ (5-alkyl-1,3-dioxa-cyclopenten-2-one-yl)methyloxy,
  $C_{10}$–$C_{14}$ (5-aryl-1,3-dioxa-cyclopenten-2-one-yl)methyloxy, or
  ($R^2$)HN—($C_1$–$C_{10}$ alkyl)oxy;

m is 0, 1, or 2;
n is 0, 1, 2, 3, or 4;
$R^9$ and $R^{10}$ are each independently H, $C_1$–$C_6$ alkyl, $C_2$–$C_6$ alkenyl, $C_2$–$C_6$ alkynyl, $C_3$–$C_7$ cycloalkyl, phenyl substituted with 0–2 $R^{6A}$, or pyridyl substituted with 0–2 $R^{6A}$;

$R^{12}$ and $R^{13}$ are each independently H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, heteroaryl($C_1$–$C_4$ alkyl)sulfonyl, aryl ($C_1$–$C_{10}$ alkyl)sulfonyl, arylsulfonyl, aryl, heteroarylcarbonyl, heteroarylsulfonyl, or heteroarylalkylcarbonyl, wherein said aryls and heteroaryls are optionally substituted with 0–3 substituents selected from the group consisting of $C_1$–$C_4$ alkyl, $C_1$–$C_4$ alkoxy, halo, CF$_3$, and NO$_2$;

$R^{16}$ is H, halogen, —CF$_3$, —CN, —NO$_2$, —NR$^{17}$R$^{18}$, methyl, ethyl, propyl, butyl, cyclopropyl, methoxy, ethoxy, propoxy, butoxy, or $C_1$–$C_4$ alkoxycarbonyl;

$R^{17}$ and $R^{18}$ are each independently H, methyl, ethyl, propyl, or butyl;

alternatively, $R^{17}$ and $R^{18}$ can be taken together to form
  —(CH$_2$)$_4$—,    —(CH$_2$)$_5$—,    or
  —CH$_2$CH$_2$NHCH$_2$CH$_2$—;

$R^{20}$ is selected from:
  H,
  $C_1$–$C_4$ alkyl substituted with 0–1 $R^{21}$,
  $C_3$–$C_6$ cycloalkyl substituted with 0–2 $R^{21}$,
  aryl substituted with 0–3 $R^{21}$, and
  aryl($C_1$–$C_4$ alkyl) substituted with 0–4 $R^{21}$; and $R^{21}$ is H, halogen, —CF$_3$, —CN, —NR$^{17}$R$^{18}$, methyl, ethyl, propyl, butyl, cyclopropyl, methoxy, ethoxy, propoxy, or butoxy;

provided that m and n are chosen such that the number of atoms connecting $R^1$ and Y is in the range of 10–18.

Preferred compounds of the present invention are compounds wherein:

A is selected from $R^1$;
  phenyl substituted with $R^1$ and 0–2 $R^6$;
  piperidinyl substituted with 0–1 $R^1$ and 0–2 $R^6$; and
  pyridyl substituted with 0–1 $R^1$ and 0–2 $R^6$;

$R^1$ is —NHR$^2$, —C(=NR$^2$)NHR$^2$, —Z(CH$_2$)$_q$NHR$^2$, —Z(CH$_2$)$_q$C(=NR$^2$)NHR$^2$, —N(R$^2$)C(=NR$^2$)NHR$^2$, —C(=NR$^2$)N(OR$^{2A}$)R$^2$, or —C(=NOR$^{2A}$)NHR$^2$;

q is 1, 2 or, 3;
Z is a bond or O;
$R^2$ is, independently at each occurence, H, $C_1$–$C_4$ alkyl, $C_2$–$C_4$ alkenyl, $C_1$–$C_6$ alkoxycarbonyl, or aryl($C_1$–$C_6$ alkoxy)carbonyl;

$R^{2A}$ is H or $C_1$–$C_6$ alkyl substituted with 0–1 $R^4$;

$R^3$ is H,
  $C_1$–$C_4$ alkyl substituted with 0–1 $R^6$,
  $C_2$–$C_4$ alkenyl substituted with 0–1 $R^6$,
  $C_2$–$C_4$ alkynyl substituted with 0–1 $R^6$,
  $C_3$–$C_6$ cycloalkyl substituted with 0–2 $R^{6A}$,
  phenyl substituted with 0–2 $R^{6A}$, or
  pyridyl substituted with 0–2 $R^{6A}$;

X is —C(=O)—;

$R^4$ is $C_1$–$C_4$ alkyl, $C_2$–$C_4$ alkenyl, $C_2$–$C_4$ alkynyl, $C_3$–$C_6$ cycloalkyl, $C_7$–$C_{12}$ bicycloalkyl, hydroxy, $C_1$–$C_4$ alkoxy, $C_1$–$C_4$ alkylthio, $C_1$–$C_4$ alkylsulfinyl, $C_1$–$C_4$ alkylsulfonyl, nitro, $C_1$–$C_4$ alkylcarbonyl, $C_6$–$C_{10}$ aryl, —N(R$^{12}$)R$^{13}$; halo, CF$_3$, CN, NO$_2$, $C_1$–$C_5$ alkoxycarbonyl, carboxy, piperidinyl, morpholinyl, or pyridinyl;

$R^5$ is H or $C_1$–$C_6$ alkyl substituted with 0–1 $R^4$;

$R^6$ is $C_3$–$C_7$ cycloalkyl substituted with 0–2 $R^{6A}$ or 0–1 $R^1$; phenyl substituted with 0–2 $R^{6A}$ or 0–1 $R^1$; or pyridyl substituted with 0–2 $R^{6A}$ or 0–1 $R^1$;

$R^{6A}$ is $C_1$–$C_4$ alkyl, $C_1$–$C_4$ alkoxy, halo, CF$_3$, NO$_2$, or NR$^{12}$R$^{13}$;

U is —C($R^7$) ($R^{7A}$)— or —N($R^7$)—;
$R^7$ is selected from:
  H,
  $C_1$–$C_4$ alkyl substituted with 0–1 $R^{16}$,
  $C_2$–$C_4$ alkenyl substituted with 0–1 $R^{16}$,
  $C_2$–$C_4$ alkynyl substituted with 0–1 $R^{16}$,
  $C_3$–$C_6$ cycloalkyl substituted with 0–2 $R^{16}$,
  $C_3$–$C_6$ cycloalkyl ($C_1$–$C_4$ alkyl) substituted with 0–1 $R^{16}$,
  aryl substituted with 0–4 $R^{16}$, and
  aryl($C_1$–$C_4$ alkyl) substituted with 0–4 $R^{16}$;
alternatively, $R^5$ and $R^7$ are taken together to form a piperidinyl, pyrrolidinyl, or piperazinyl ring;
$R^{7A}$ is H;
$R^8$ is selected from:
  H,
  —C (=O)NH$R^{20}$,
  $C_1$–$C_6$ alkyl substituted with 0–1 $R^{16}$,
  $C_2$–$C_4$ alkenyl substituted with 0–1 $R^{16}$,
  $C_2$–$C_4$ alkynyl substituted with 0–1 $R^{16}$,
  $C_3$–$C_6$ cycloalkyl substituted with 0–2 $R^{16}$,
  aryl substituted with 0–4 $R^{16}$,
  aryl($C_1$–$C_4$ alkyl) substituted with 0–4 $R^{16}$,
  a 5–6 membered heterocyclic ring system having 1–3 heteroatoms selected independently from O,S, and N, said heterocyclic ring being substituted with 0–4 $R^{16}$, and
  $C_1$–$C_4$ alkyl substituted with a 5–10 membered heterocyclic ring system having 1–3 heteroatoms selected independently from O,S, and N, said heterocyclic ring being substituted with 0–4 $R^{16}$;
alternatively, $R^5$ and $R^8$ are taken together to form a piperidinyl or a pyrrolidinyl ring;
alternatively, $R^7$ and $R^8$ are taken together to form a 5–6 membered carbocyclic ring, wherein said carbocyclic ring is selected from phenyl, cyclohexyl, cyclopentyl, cyclohexenyl, or cyclopentenyl;
$R^{8A}$ is H or $C_1$–$C_4$ alkyl substituted with 0–1 $R^{16}$;
k is 0 or 1;
j is 0, 1, or 2;
V is O or a single bond;
Q is —C(=O)Y or —$SO_3H$;
Y is hydroxy,
  $C_1$–$C_{10}$ alkyloxy,
  $C_3$–$C_{11}$ cycloalkyloxy,
  $C_6$–$C_{10}$ aryloxy,
  $C_7$–$C_{11}$ aralkyloxy,
  $C_3$–$C_{10}$ alkylcarbonyloxyalkyloxy,
  $C_3$–$C_{10}$ alkoxycarbonyloxyalkyloxy,
  $C_2$–$C_{10}$ alkoxycarbonylalkyloxy,
  $C_5$–$C_{10}$ cycloalkylcarbonyloxyalkyloxy,
  $C_5$–$C_{10}$ cycloalkoxycarbonyloxyalkyloxy,
  $C_5$–$C_{10}$ cycloalkoxycarbonylalkyloxy,
  $C_7$–$C_{11}$ aryloxycarbonylalkyloxy,
  $C_8$–$C_{12}$ aryloxycarbonyloxyalkyloxy,
  $C_8$–$C_{12}$ arylcarbonyloxyalkyloxy,
  $C_5$–$C_{10}$ alkoxyalkylcarbonyloxyalkyloxy,
  $C_5$–$C_{10}$ (5-alkyl-1,3-dioxa-cyclopenten-2-one-yl) methyloxy,
  $C_{10}$–$C_{14}$ (5-aryl-1,3-dioxa-cyclopenten-2-one-yl) methyloxy, or
  ($R^2$)HN—($C_1$–$C_{10}$ alkyl)oxy;
m is 0, 1, or 2;
n is 0, 1, 2, or 3;
$R^9$ is H, $C_1$–$C_4$ alkyl, $C_2$–$C_4$ alkenyl, $C_2$–$C_4$ alkynyl, $C_3$–$C_6$ cycloalkyl, phenyl substituted with 0–2 $R^{6A}$, or pyridyl substituted with 0–2 $R^{6A}$;
$R^{10}$ is H, methyl, ethyl, propyl, or butyl;
$R^{12}$ and $R^{13}$ are each independently H, $C_1$–$C_6$ alkyl, $C_1$–$C_6$ alkoxycarbonyl, $C_1$–$C_6$ alkylcarbonyl, $C_1$–$C_6$ alkylsulfonyl, heteroaryl($C_1$–$C_4$ alkyl)sulfonyl, aryl ($C_1$–$C_6$ alkyl)sulfonyl, arylsulfonyl, aryl, heteroarylcarbonyl, heteroarylsulfonyl, or heteroarylalkylcarbonyl, wherein said aryls and heteroaryls are optionally substituted with 0–3 substituents selected from the group consisting of $C_1$–$C_4$ alkyl, $C_1$–$C_4$ alkoxy, halo, $CF_3$, and $NO_2$;
$R^{16}$ is H, halogen, —$CF_3$, —CN, —$NO_2$, —$NR^{17}R^{18}$, methyl, ethyl, propyl, butyl, cyclopropyl, methoxy, ethoxy, propoxy, butoxy, or $C_1$–$C_4$ alkoxycarbonyl;
$R^{17}$ and $R^{18}$ are each independently H, methyl, ethyl, propyl, or butyl;
alternatively, $R^{17}$ and $R^{18}$ can be taken together to form —$(CH_2)_4$—, —$(CH_2)_5$—, or —$CH_2CH_2NHCH_2CH_2$—;
$R^{20}$ is selected from:
  H,
  $C_1$–$C_4$ alkyl substituted with 0–1 $R^{21}$,
  $C_3$–$C_6$ cycloalkyl substituted with 0–2 $R^{21}$,
  aryl substituted with 0–3 $R^{21}$, and
  aryl($C_1$–$C_4$ alkyl) substituted with 0–3 $R^{21}$; and
$R^{21}$ is H, halogen, —$CF_3$, —CN, —$NR^{17}R^{18}$, methyl, ethyl, propyl, butyl, cyclopropyl, methoxy, ethoxy, propoxy, or butoxy;
provided that m and n are chosen such that the number of atoms connecting $R^1$ and Y is in the range of 10–18.

More preferred compounds of the present invention are compounds, wherein:

A is phenyl substituted with $R^1$ and 0–1 $R^6$, or piperidinyl substituted with 0–1 $R^6$;
$R^1$ is —NH$R^2$, —C(=N$R^2$)NH$R^2$, —$(CH_2)_q$NH$R^2$, —$(CH_2)_q$C(=N$R^2$)NH$R^2$, or —N($R^2$)C(=N$R^2$)NH$R^2$;
q is 1, 2, or 3;
$R^2$ is, independently at each occurence, H, methyl, ethyl, propyl, butyl, or $C_2$–$C_4$ alkenyl;
$R^3$ is H,
  $C_1$–$C_4$ alkyl substituted with 0–1 $R^6$ or
  $C_2$–$C_4$ alkenyl substituted with 0–1 $R^6$;
X is —C(=O)—;
$R^4$ is methyl, ethyl, propyl, butyl, methoxy, ethoxy, propoxy, or butoxy, fluoro, chloro, bromo, iodo, $CF_3$, $NO_2$, $NH_2$ or $N(CH_3)_2$;
$R^5$ is H or $C_1$–$C_2$ alkyl substituted with 0–1 $R^4$;
$R^6$ is $C_3$–$C_6$ cycloalkyl substituted with 0–2 $R^{6A}$; phenyl substituted with 0–2 $R^{6A}$; or pyridyl substituted with 0–2 $R^{6A}$;
$R^{6A}$ is methyl, ethyl, propyl, butyl, methoxy, ethoxy, propoxy, or butoxy, fluoro, chloro, bromo, iodo, $CF_3$, $NO_2$, $NH_2$, $N(CH_3)_2$, or $N(CH_2CH_3)_2$;
U is —C($R^7$)($R^7A$)— or —N($R^7$)—;
$R^7$ is selected from:
  H, methyl, ethyl, propyl, and butyl;
$R^{7A}$ is H;
$R^8$ is selected from:
  H,
  —C(=O)NH$R^{20}$,
  $C_1$–$C_6$ alkyl substituted with 0–1 $R^{16}$,
  $C_2$–$C_4$ alkenyl substituted with 0–1 $R^{16}$,
  $C_2$–$C_4$ alkynyl substituted with 0–1 $R^{16}$, $C_3$–$C_6$ cycloalkyl substituted with 0–2 $R^{16}$,
aryl substituted with 0–4 $R^{16}$,
aryl($C_1$–$C_4$ alkyl) substituted with 0–2 $R^{16}$,
a 5–6 membered heterocyclic ring system having 1–3 heteroatoms selected independently from O,S, and N, said heterocyclic ring being substituted with 0–2 $R^{16}$, and
$C_1$–$C_4$ alkyl substituted with a 5–10 membered heterocyclic ring system having 1–3 heteroatoms selected independently from O,S, and N, said heterocyclic ring being substituted with 0–2 $R^{16}$;

$R^{8A}$ is H, methyl, ethyl, propyl, or butyl;

k is 0;

j is 0;

V is a single bond;

Q is —C(=O)Y;

Y is hydroxy-,
$C_1$–$C_4$ alkoxy-,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
t-butyloxycarbonyloxymethoxy-,
i-propyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-,
1-(2-(2-methoxypropyl)carbonyloxy)ethoxy-,
($R^2$)HN—($C_1$–$C_6$ alkyl)oxy-, morpholinoethoxy-, or pyrrolidinoethoxy;

m is 0 or 1;

n is 0 or 1;

$R^9$ is H, methyl, ethyl, propyl, butyl, phenyl substituted with 0–2 $R^6$, or pyridyl substituted with 0–2 $R^6$;

$R^{10}$ is H;

$R^{16}$ is H, halogen, —$CF_3$, —CN, —$NO_2$, —$NR^{17}R^{18}$, methyl, ethyl, propyl, butyl, cyclopropyl, methoxy, ethoxy, propoxy or butoxy;

$R^{17}$ and $R^{18}$ are each independently H, methyl, ethyl, propyl or butyl.

$R^{20}$ is selected from:
H,
$C_1$–$C_3$ alkyl substituted with 0–1 $R^{21}$,
$C_3$–$C_6$ cycloalkyl substituted with 0–1 $R^{21}$,
aryl substituted with 0–2 $R^{21}$, and
aryl($C_1$–$C_2$ alkyl) substituted with 0–2 $R^{21}$; and $R^{21}$ is H, F, Cl, Br, I, —$CF_3$, —CN, $NH_2$, $N(CH_3)_2$, $N(CH_2CH_3)_2$, methyl, ethyl, cyclopropyl, methoxy, or ethoxy.

Even more preferred compounds of the present invention are compounds of Formula (Ia),

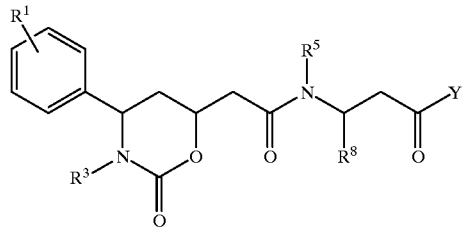

(Ia)

wherein:
$R^1$ is —C(=$NR^2$)$NHR^2$, —$(CH_2)_qC$(=$NR^2$)$NHR^2$ or —N($R^2$)C(=$NR^2$) $NHR^2$;

q is 1 or 2;

$R^2$ is, independently at each occurence, H, methyl or ethyl;

$R^3$ is H,
methyl substituted with 0–1 $R^6$, or
ethyl substituted with 0–1 $R^6$;

$R^5$ is H, methyl or ethyl;

$R^6$ is $C_3$–$C_6$ cycloalkyl substituted with 0–2 $R^{6A}$;
phenyl substituted with 0–2 $R^{6A}$; or
pyridyl substituted with 0–2 $R^{6A}$;

$R^{6A}$ is methyl, ethyl, propyl, butyl, methoxy, ethoxy, propoxy, or butoxy, fluoro, chloro, bromo, iodo, $CF_3$, $NO_2$, $NH_2$ or $N(CH_3)_2$;

$R^8$ is selected from:
H,
—C(=O) $NHCH_2R^{21}$,
—C(=O)$NH(CH_2)_2R^{21}$,
—C(=O)$NH(CH_2)_3R^{21}$,
methyl substituted with 0–1 $R^{16}$,
ethyl substituted with 0–1 $R^{16}$,
phenyl substituted with 0–2 $R^{16}$,
phenyl($CH_2$)— substituted with 0–2 $R^{16}$,
phenyl($CH_2CH_2$)— substituted with 0–2 $R^{16}$,
a 5–6 membered heterocyclic ring system selected from pyrrolyl, indolyl, 2-isobenzazolyl-, indazolyl, isoindazolyl, pyridinyl, quinolinyl, isoquinolinyl, and piperidinyl;
methyl substituted with a 5–6 membered heterocyclic ring system selected from pyrrolyl, indolyl, 2-isobenzazolyl-, indazolyl, isoindazolyl, pyridinyl, quinolinyl, isoquinolinyl, and piperidinyl; and
ethyl substituted with a 5–6 membered heterocyclic ring system selected from pyrrolyl, indolyl, 2-isobenzazolyl-, indazolyl, isoindazolyl, pyridinyl, quinolinyl, isoquinolinyl, and piperidinyl;

Y is hydroxy-, methoxy-, ethoxy-, n-butoxy-, isopropoxy-, isobutoxy-, benzyloxy-, methylcarbonyloxymethoxy-, ethylcarbonyloxymethoxy-, tert-butylcarbonyloxymethoxy-, cyclohexylcarbonyloxymethoxy-, tert-butyloxycarbonyloxymethoxy-, dimethylaminoethoxy-, diethylaminoethoxy-, morpholinoethoxy-, or pyrrolidinoethoxy-;

$R^{16}$ is H, halogen, —$CF_3$, methyl, ethyl, methoxy, ethoxy, —$NH_2$, —$N(CH_3)_2$, or —$N(CH_2CH_3)_2$;

$R^{17}$ and $R^{18}$ are each independently H, methyl, or ethyl; and $R^{21}$ is H, F, Cl, Br, I, —$CF_3$, —CN, $NH_2$, $N(CH_3)_2$, $N(CH_2CH_3)_2$, methyl, ethyl, cyclopropyl, methoxy, or ethoxy.

In a further preferred embodiment compounds of the present invention are selected from 3-[[4(S)-[4-(aminoiminomethyl)phenyl]tetrahydro-3-methyl-2-oxo-2H-1,3-oxazin-6(R)-yl]acetyl] aminopropionic acid;
3-[[4(R)-[4-(aminoiminomethyl)phenyl]tetrahydro-3-methyl-2-oxo-2H-1,3-oxazin-6(S)-yl]acetyl]amino propionic acid;
Trans-3-[[4-[4-(aminoiminomethyl)phenyl]tetrahydro-3-methyl-2-oxo-2H-1,3-oxazin-6-yl]acetyl]amino propionic acid;
3(R)-[[4(S)-[4-(aminoiminomethyl)phenyl]tetrahydro-3-methyl-2-oxo-2H-1,3-oxazin-6(R)-yl]acetyl] aminobutyric acid;
3(R)-[[4(S)-[4-(aminoiminomethyl)phenyl]tetrahydro-3-methyl-2-oxo-2H-1,3-oxazin-6(R)-yl]acetyl]amino-5-phenylvaleric acid;
3(S)-[[4(S)-[4-(aminoiminomethyl)phenyl]tetrahydro-3-methyl-2-oxo-2H-1,3-oxazin-6(R)-yl]acetyl]amino-3-(pyridin-3-yl)propionic acid;
3(R)-[[4(S)-[4-(aminoiminomethyl)phenyl]tetrahydro-3-methyl-2-oxo-2H-1,3-oxazin-6(R)-yl]acetyl]amino-3-(pyridin-3-yl)propionic acid;
3(S)-[[4(S)-[4-(aminoiminomethyl)phenyl]tetrahydro-3-methyl-2-oxo-2H-1,3-oxazin-6(R)-yl]acetyl]amino-3-phenylpropionic acid;
3(R)-[[4(S)-[4-(aminoiminomethyl)phenyl]tetrahydro-3-methyl-2-oxo-2H-1,3-oxazin-6(R)-yl]acetyl]amino-3-phenylpropionic acid;
3(R)-[[4(S)-[4-(aminoiminomethyl)phenyl]tetrahydro-3-methyl-2-oxo-2H-1,3-oxazin-6(R)-yl]acetyl]amino-4-[(3-dimethylamino)propyl]amino-4-oxobutanoic acid;
3(R)-[[4(S)-[4-(aminoiminomethyl)phenyl]tetrahydro-3-methyl-2-oxo-2H-1,3-oxazin-6(R)-yl]acetyl]amino-5-indole-3-valeric acid;
3-[[4(S)-[4-(aminoiminomethyl)phenyl]tetrahydro-3-benzyl-2-oxo-2H-1,3-oxazin-6(R)-yl]acetyl] aminopropionic acid;
3-[[4(R)-[4-(aminoiminomethyl)phenyl]tetrahydro-3-benzyl-2-oxo-2H-1,3-oxazin-6(S)-yl]acetyl] aminopropionic acid;
3(R)-[[4(S)-[4-(aminoiminomethyl)phenyl]tetrahydro-3-benzyl-2-oxo-2H-1,3-oxazin-6(R)-yl]acetyl] aminobutyric acid;
[N-[[4(S)-[4-(N-butylaminoiminomethyl)phenyl]tetrahydro-3-benzyl-2-oxo-2H-1,3-oxazin-6(R)-yl]acetyl]piperidin-4-yl]acetic acid;
3(R)-[[4(S)-[4-(N-butylaminoiminomethyl)phenyl]tetrahydro-3-methyl-2-oxo-2H-1,3-oxazin-6(R)-yl]acetyl]amino-5-phenylvaleric acid;
3-[[2-methyl-3(S)-[4-(aminoiminomethyl)phenyl]-isoxazolidin-5(R)-yl]acetyl]aminopropionic acid;
3-[[2-methyl-3(R)-[4-(aminoiminomethyl)phenyl]-isoxazolidin-5(S)-yl]acetyl]aminopropionic acid;
3(R)-[[2-methyl-3(R)-[4-(aminoiminomethyl)phenyl]-isoxazolidin-5(S)-yl]acetyl]aminobutyric acid; and
[N-[[4(S)-[4-(N-butylaminoiminomethyl)phenyl]tetrahydro-3-methyl-2-oxo-2H-1,3-oxazin-6(R)-yl]acetyl]piperidin-4-yl]acetic acid.

A second embodiment of the present invention relates to novel compounds of the Formula (II):

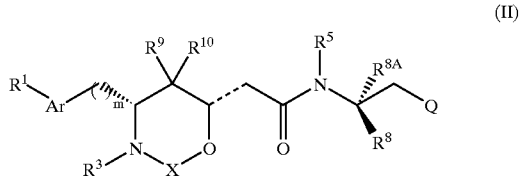

(II)

or their pharmaceutically acceptable salts thereof.

Prefered compounds of the present invention are compounds of Formula (IIa):

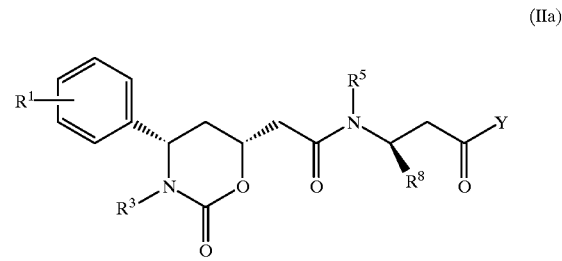

(IIa)

or their pharmaceutically acceptable salts thereof.

A third embodiment of the present invention relates to novel compounds of the Formula (III):

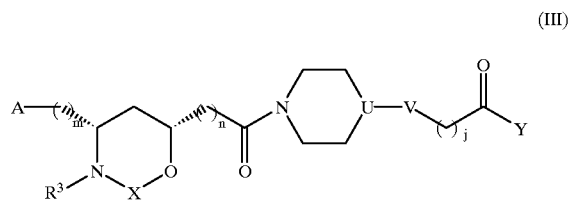

(III)

or their pharmaceutically acceptable salts thereof.

A fourth embodiment of the present invention relates to a pharmaceutical composition comprising a pharmaceutical carrier and a therapeutically effective amount of a compound of the present invention.

A fifth embodiment of the present invention relates to a method in inhibiting the aggregation of blood platelets which comprises administering to a host in need of such inhibition a therapeutically effective amount of a compound of the present invention.

A sixth embodiment of the present invention relates to a method of treating thromboembolic disorders selected from thrombus or embolus formation, harmful platelet aggregaion, reocclusion following thrombolysis, reperfusion injury, restenosis, atherosclerosis, stroke myocardial infarction, and unstable angina, which comprises administering to a host in need of such treatment a therapeutically effective amount of a compound of the present invention.

A seventh embodiment of the present invention relates to a method of treating metastatic cancer which comprises administering to a host in need of such treatment a therapeutically effective amount of a compound of the present invention.

The compounds of Formula (I) of the present invention are useful for the treatment (including prevention) of thromboembolic disorders. The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of the invention described above.

The compounds of Formula (I) of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption, and where the aggregated platelets may form thrombi and thromboemboli. The compounds of the present invention may be administered to these surgical patients to prevent the formation of thrombi and thromboemboli.

Extracorporeal circulation is routinely used during cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the extracorporeal circuit. Platelets released from artificial surfaces show impaired homeostatic function. The compounds of the invention may be administered to prevent such ex vivo adhesion.

The compounds of the present invention may be used for other ex vivo applications to prevent cellular adhesion in biological samples.

Other applications of these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures The compounds of the present invention may also be used to prevent myocardial infarction. The compounds of the present invention are useful as thrombolytics for the treatment of thromboembolic disorders.

The compounds of the present invention can also be administered in combination with one or more additional therapeutic agents select from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula (I) of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of the invention that when administered alone or in combination with an additional therapeutic agent to a cell or mammal is effective to prevent or ameliorate the thromboembolic disease condition or the progression of the disease.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as Coumadin™) and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer Inc. (New York, N.Y.), as Feldane™. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin and other inhibitors of thrombin synthesis such as Factor XA. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication No. 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as Eminase™. The term urokinase, as used herein, is intended to denote both dual and single chain urokinase, the latter also being referred to herein as prourokinase.

Administration of the compounds of Formula (I) in combination with such additional therapeutic agent, may afford an efficacy advantage over the compounds and agents alone, and may do so while permitting the use of lower doses of each. A lower dosage minimizes the potential of side effects, thereby providing an increased margin of safety.

GPIIb/IIIa is known to be overexpressed in metastatic tumor cells. The compounds or combination products of the present invention may also be useful for the treatment, including prevention, of metastatic cancer.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^4$, $R^{6A}$, $R^{12}$, $R^{13}$, etc.) occurs more than one time in any constituent or in any formula, its definition on each occurrence is independent of its definition at every other occurrence. Thus, for example, if a group is shown to be substituted with 0–2 $R^6$, then said group may optionally be substituted with up to two $R^6$ and $R^6$ at each occurrence is selected independently from the defined list of possible $R^6$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula (I), then such substituent may be bonded via any atom in such substituent. For example, when the substituent is piperidinyl, or morpholinyl, unless specified otherwise, said piperidinyl or morpholinyl, tetrazolyl group may be bonded to the rest of the compound of Formula (I) via any atom in such piperidinyl or morpholinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$–$C_{10}$" denotes alkyl having 1 to 10 carbon atoms); "alkoxy" represents an alkyl group of indicated number of carbon atoms attached through an oxygen bridge; "cycloalkyl" is intended to include saturated ring groups, including mono-, bi-, or poly-cyclic ring systems, such as cyclopropyl, cyclobutyl, cyclopentyl, cyclohexyl, cycloheptyl, cyclooctyl, and adamantyl and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula (I). Such "alkylene", "alkenylene", "phenylene", and the like, may alternatively and equivalently be denoted herein as "-(alkyl)-", "-(alkenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl optionally substituted with 0–3 groups independently selected from methyl, methoxy, amino, hydroxy, halogen, $C_1$–$C_6$ alkoxy, $C_1$–$C_6$ alkyl, $CF_3$, $SCH_3$, $S(O)CH_3$, $SO_2CH_3$, —$N(CH_3)_2$, $C_1$–$C_4$ haloalkyl, methylenedioxydiyl, ethylenedioxydiyl; the term "aralkyl" represents an aryl group attached through an alkyl bridge.

As used herein, the terms "heterocycle", "heterocyclic ring" or "heterocyclic ring system" are intended to mean a stable 5–6 membered monocyclic heterocyclic ring which is saturated, partially unsaturated or unsaturated (aromatic or "heteroaryl") and which consists of carbon atoms and from 1 to 3 heteroatoms independently selected from the group consisting of N, O and S. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one.

As used herein, the term "heteroaryl" refers to aromatic heterocyclic groups. Such heteroaryl groups are preferably 5–6 membered monocylic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl.

As used herein, "pharmaceutically acceptable salts" refer to derivatives of the disclosed compounds wherein the parent compound of Formula (I) is modified by making acid or base salts of the compound of Formula (I). Examples of pharmaceutically acceptable salts include, but are not limited to, mineral or organic acid salts of basic residues such as amines; alkali or organic salts of acidic residues such as carboxylic acids; and the like. "Prodrugs" are considered to be any covalently bonded carriers which release the active parent drug according to Formula (I) in vivo when such prodrug is administered to a mammalian subject. Prodrugs of the compounds of Formula (I) are prepared by modifying functional groups present in the compounds in such a way that the modifications are cleaved, either in routine manipulation or in vivo, to the parent compounds. Prodrugs include compounds of Formula (I) wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula (I), and the like. Examples of the prodrug forms of the compounds of the present invention include the following esters: methyl; ethyl; isopropyl; n-butyl; i-butyl; methylcarbonyloxymethyl-; ethylcarbonyloxymethyl-; t-butylcarbonyloxymethyl-; cyclohexylcarbonyloxymethyl-; 1-(methylcarbonyloxy) ethyl-; 1-(ethylcarbonyloxy)ethyl-; 1-(t-butylcarbonyloxy) ethyl-; 1-(cyclohexylcarbonyloxy)ethyl-; i-propyloxycarbonyloxymethyl-; cyclohexylcarbonyloxymethyl-; t-butyloxycarbonyloxymethyl-; 1-(i-propyloxycarbonyloxy) ethyl-; 1-(cyclohexyloxycarbonyloxy)ethyl-; 1-(t-butyloxycarbonyloxy)-ethyl-; dimethylaminoethyl-; diethylaminoethyl-; (5-methyl-1,3-dioxacyclopenten-2-on-4-yl)methyl-; (5-(t-butyl)-1,3-dioxacyclopenten-2-on-4-yl) methyl-; (1,3-dioxa-5-phenyl-cyclopenten-2-on-4-yl) methyl-; 1-(2-(2-methoxypropyl)-carbonyloxy)ethyl-.

The pharmaceutically acceptable salts of the compounds of Formula (I) include the conventional non-toxic salts or the quaternary ammonium salts of the compounds of Formula (I) formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula (I) can be formed with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The following abbreviations are used herein:

| | |
|---|---|
| Boc | tert-butyloxycarbonyl |
| Boc$_2$O | di-tert-butyl dicarbonate |
| CDI | 1,1'-carbonyldiimidazole |
| DCE | dichloroethane |
| DDQ | 2,3-dichloro-5,6-dicyano-1,4-benzoquinone |
| DIBAL-H | diisobutylaluminum hydride |
| DIEA | diisopropylethylamine |
| DMAP | 4-dimethylaminopyridine |
| DMF | N,N-dimethylformamide |
| EtOAc | ethyl acetate |
| EtOH | ethyl alcohol |
| IBCF | isobutylchloroformate |
| NMM | N-methylmorpholine |
| pyr | pyridine |
| PyBOP | benzotriazole-1-yl-oxy-tris-pyrrolidino-phosphoniumhexafluorophosphate |
| TEA | triethyl amine |
| TFA | trifluoroacetic acid |
| THF | tetrahydrofuran |

In general, the compounds of this invention can be prepared by a coupling of one of the following key acid intermediates of type 1, 2 or 3 with an amino acid such as a β-aminoacid or an aminoacid of type 4 followed by suitable chemical transformations.

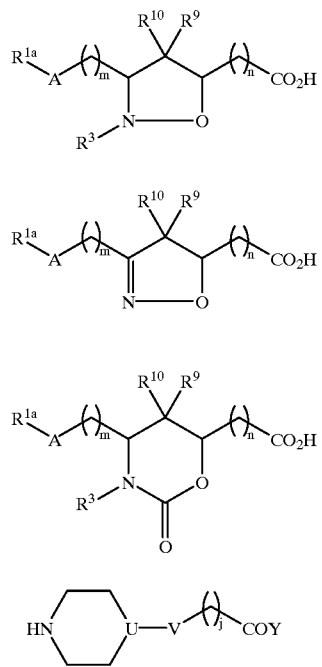

($R^{1a}$ represents a precusor of $R^1$; could be a protected $R^1$, cyano, etc)

The acid intermediate of type 1 can be prepared via a dipolar cycloaddition of a nitrone with an appropriate dipolarophile as we disclosed in the application WO98/06707. Scheme I represents a general example.

Scheme I

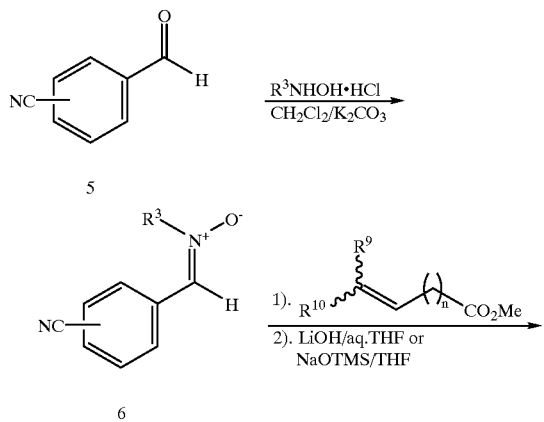

-continued

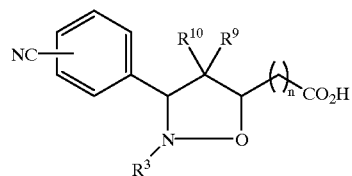

Cycloaddition of a nitrile oxide, which is prepared from hydroxylamines by treatment with NCS in DMF (Liu, et al. J. Org. Chem. 1980, 45, 3916) followed by in situ dehydration in the presence of TEA, with a suitably substituted alkene affords an isoxazoline. Hydrolysis of the isoxazoline gives an acid of type 2 (Scheme II).

Scheme II

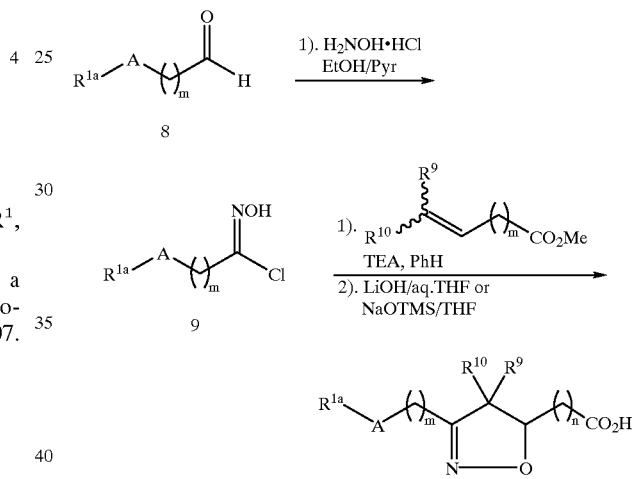

Scheme III

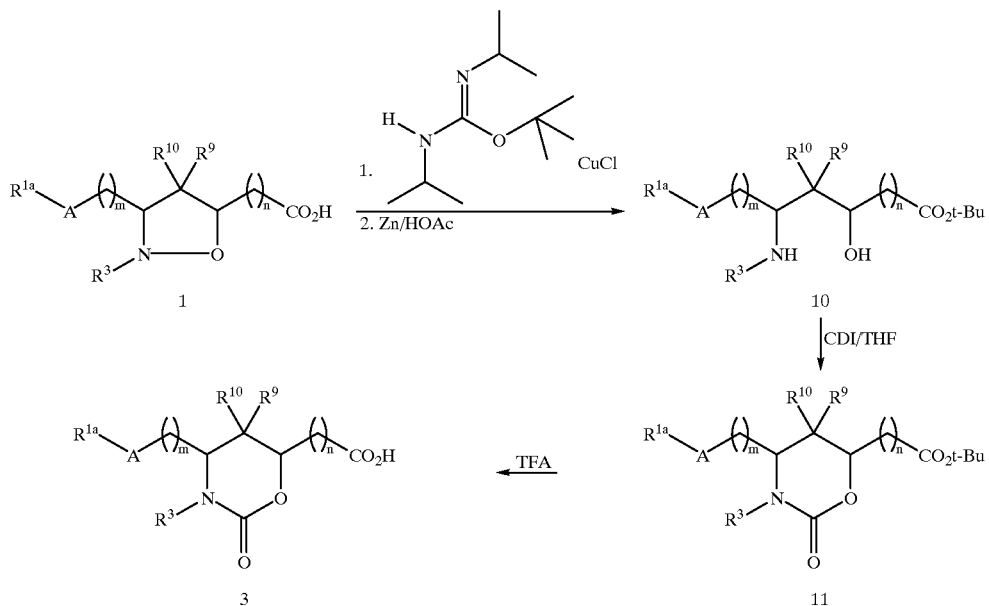

The acid intermediate of type 3 can be prepared either from the acid of type 1 or type 2. tert-Butyl esterification of 1 using the method developed by Deccico, et al (*J. Org. Chem.* 1995, 60, 4782) followed by treatment with Zn/HOAc affords 1,3-aminoalcohol 10. Ring closure of 10 on treatment with CDI or phosgene gives cyclic carbamate 12, which is saponificated in the presence of TFA to form 3 (Scheme III).

Scheme IV outlines a syntheis of type 3 acid from 2. Similarly, 2 is first converted to the corresponding tert-butyl ester which forms 1,3-aminoalcohol 12 on treatment with Zn/HOAc. Reductive amination of 12 with an aldehyde or ketone in the presence of a reducing reagent such as NaB(AcO)$_3$H, NaBCNH$_3$ or NaBH$_4$ gives 10, which is then transformed to 3.

Scheme IV

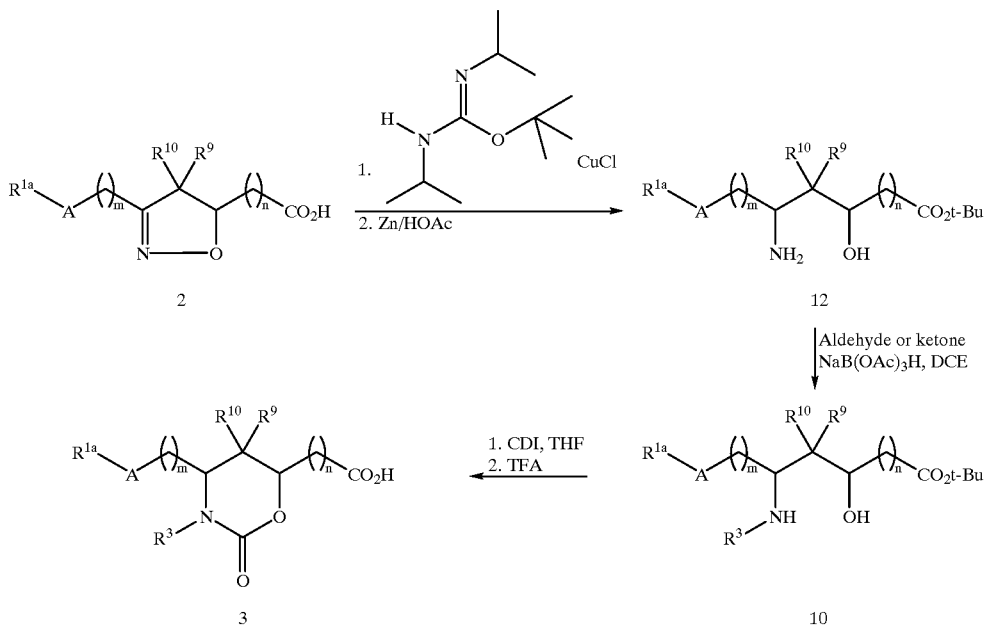

Alternatively, the type 1 acid may also be prepared from 2. Thus, 2 is fisrt converted to an ester, for example, methyl ester. On treatment with an alkylating reagent, this ester forms a salt 13, which affords an isoxazolidine 14 on reaction with a varity of reducing reagents such as NaBH$_4$. Basic hydrolysis of 14 furnishes the transformation (Scheme V).

Scheme V

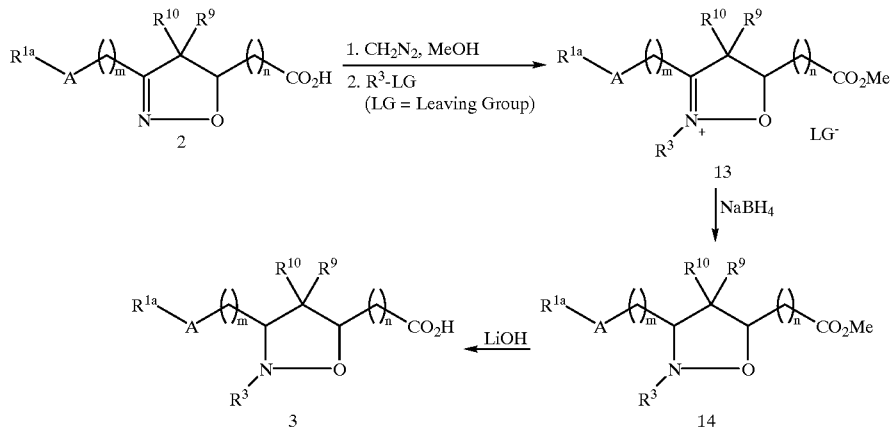

The geometrically pure version of the acids of type 1 or type 3 can be obtained by chromatography or by controlling reaction conditions or by choosing suitable reagents at some stage in the synthesis of these two types of acids.

A varity of methods are applied to the synthesis of enantiomerically pure acids of type 1,2 or 3, including chiral chromatography separation, chemical resolution and enzymatic resolution. Scheme VI shows two examples of enzymatic resolution.

Scheme VI

Method 1 (See, Zhang, et al Tetrahedron Lett. 1966, 37, 4455.)

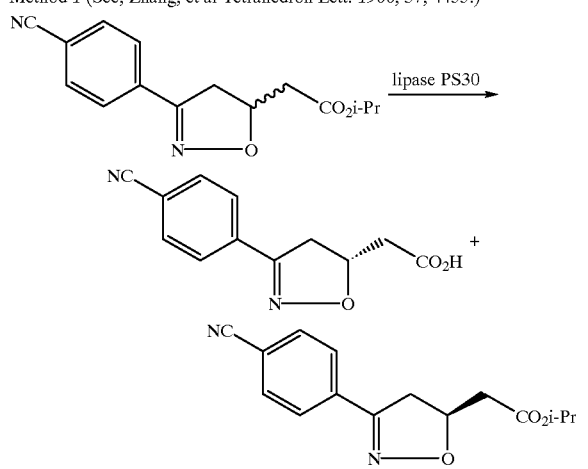

Method 2

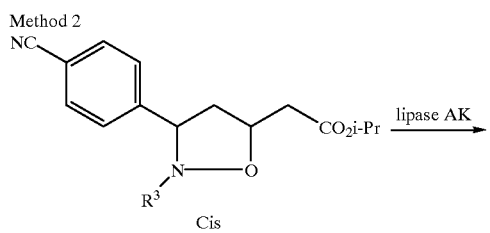

-continued

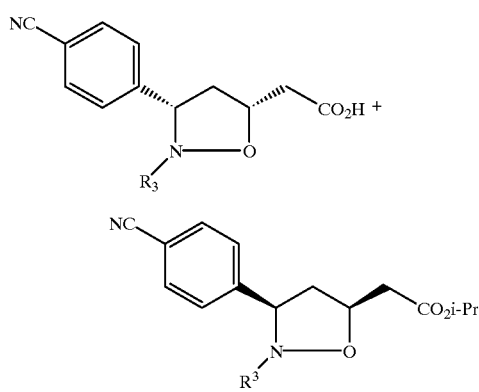

Depending on the availability of the starting materials, the compatibility of the functional groups in the molecule and other factors, compounds of this invention can be prepared by a coulping reaction of an acid of either type 1, 2 or 3 with an aminoacid. Scheme VII illustrates a general synthetic sequence starting with the type 1 acid. Coupling of an acid of type 1 with an amino ester of type 4 using standard coupling reagents, such as DCC/HOBt or PyBOP, affords a nitrile-amide 15. The isoxazolidine ring is expanded to a cyclic carbamate ring by a sequential treatment with Zn/HOAc and CDI to yield 16. The transformation of the cyano group to an amidine is effected via the corresponding imidate, or thioimidate, or amidoxime. Saponification of the resulting amidine gives the final compound 17.

Scheme VII

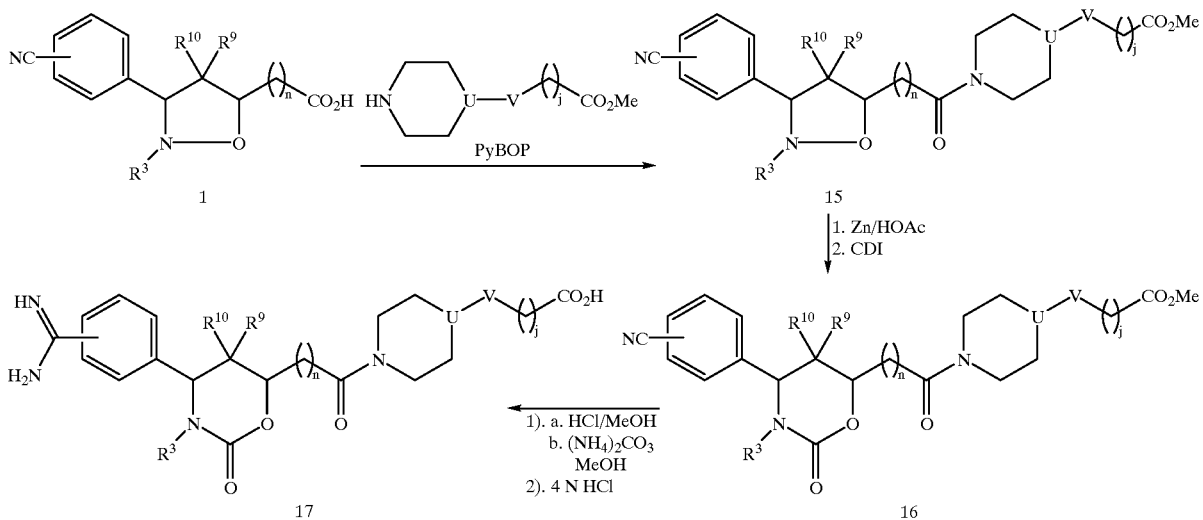

Scheme VIII describes a synthetic sequence for the compounds of this invention starting with an acid of type 2. Coupling of 2 with a β-amino ester followed by a Zn-promoted reductive ring cleavage affords 1,3-aminoalcohol 18. This 1,3-aminoalcohol is transformed to 19 through a reductive amination and ring closure. Compound 19 is then converted to the final product 20 the same way as 16 to 17.

Compounds of Formula (I) wherein X is a single bond may be prepared from intermediates such as 15 by conversion of the cyano group to an amidine followed by saponification.

Compounds of Formula (I) wherein $R^1$ is $R^2HN(R^2N=)$ $CN(R^2)$— may be prepared by a transformation of the amine to the guanidine, which is brought about by using the method described by Kim, et al (Tetrahedron Lett. 1993, 48, 7677).

Compounds of Formula (I) wherein $R^1$ is $R^2HNC(O)$— may be prepared by reaction of the corresponding nitrile with an appropriate alcohol under acidic conditions (J. Med. Chem. 1991, 34, 851) or with hydrogen peroxide under basic conditions (J. Am. Chem. Soc. 1958. 80, 2257).

Compounds of Formula (I) wherein $R^1$ is $R^2(R^5O)N$ $(R^2N=)C$— or $R^2HN$ $(R^5ON=)C$— may be prepared by reaction of the corresponding nitrile with an appropriately substituted hydroxyamine.

Scheme VIII

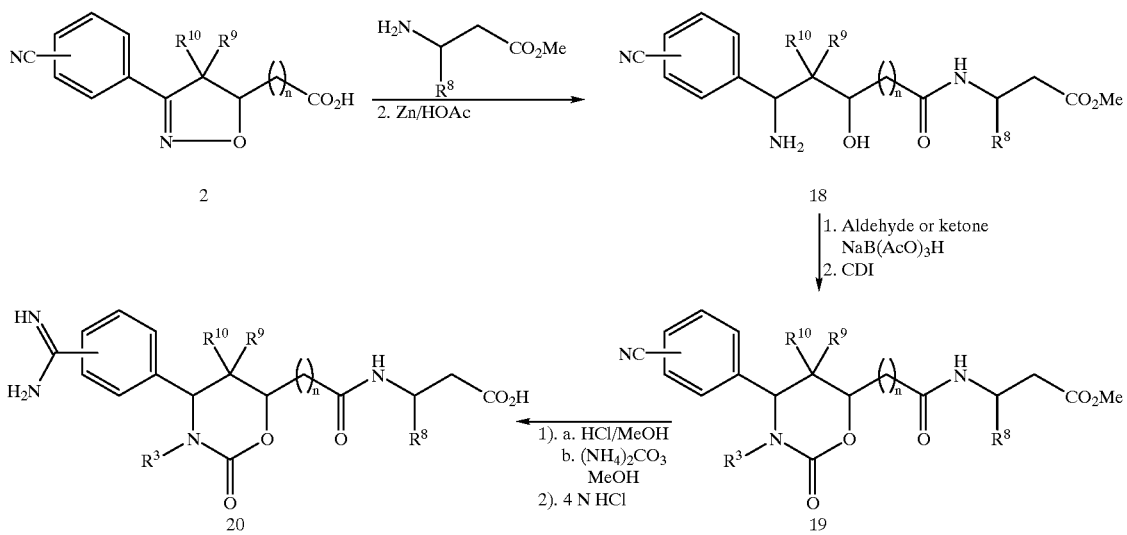

The appropriately substituted racemic b-amino acids may be purchased commercially or, as is shown in Scheme IX, Method 1, prepared from the appropriate aldehyde, malonic acid and ammonium acetate according to the procedure of Johnson and Livak (*J. Am. Chem. Soc.* 1936, 58, 299). Racemic b-substituted-b-amino esters may be prepared through the reaction of dialkylcuprates or alkyllithiums with 4-benzoyloxy-2-azetidinone followed by treatment with anhydrous ethanol (Scheme IX, Method 2) or by reductive amination of b-keto esters as is described in W09316038. (Also see Rico et al., J. Org. Chem. 1993, 58, 7948–51.) Enantiomerically pure b-substituted-b-amino acids can be obtained through the optical resolution of the racemic mixture or can be prepared using numerous methods, including: Arndt-Eistert homologation of the corresponding a-amino acids as shown in Scheme IX, Method 3 (see Meier, and Zeller, *Angew. Chem. Int. Ed. Engl.* 1975, 14, 32; Rodriguez, et al. *Tetrahedron Lett.* 1990, 31, 5153; Greenlee, *J. Med. Chem.* 1985, 28, 434 and references cited within); and through an enantioselective hydrogenation of a dehydroamino acid as is shown in Scheme VI, Method 4 (see Asymmetric Synthesis, Vol. 5, (Morrison, ed.) Academic Press, New York, 1985). A comprehensive treatise on the preparation of b-amino acid derivatives may be found in patent application WO 9307867, the disclosure of which is hereby incorporated by reference.

Scheme IX

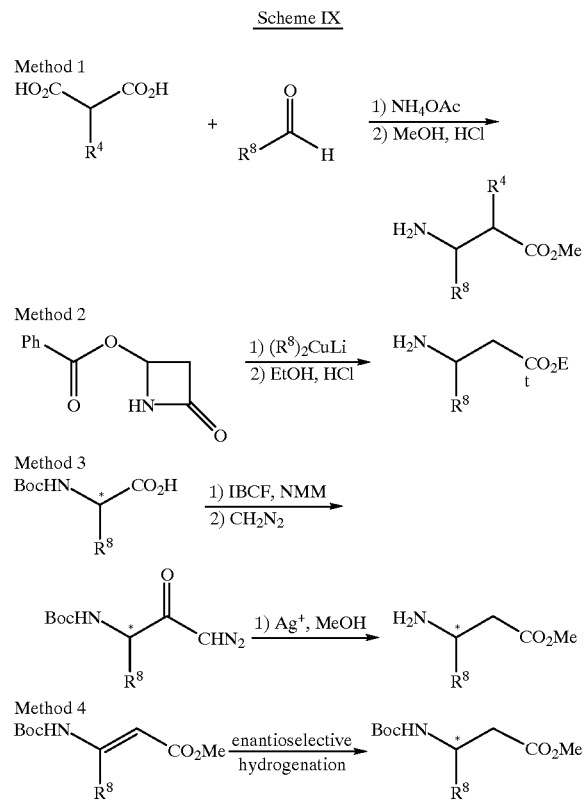

The compounds of this invention and their preparation can be further understood by the following procedures and examples, which exemplify but do not constitute a limit of their invention.

EXAMPLE 1

3-[[4(S)-[4-(aminoiminomethyl)phenyl]tetrahydro-3-methyl-2-oxo-2H-1,3-oxazin-6(R)-yl]acetyl] aminopropionic acid HCl salt Part A. C-(4-Cyanophenyl)-N-methylnitrone A mixture of 4-cyanobenzaldehyde (3.3 g, 25.2 mmol), N-methylhydroxyamine hydrogen chloride and sodium bicarbonate (4.23 g, 50.4 mmol) in dry methylene chloride (80 ml) was stirred at rt for 5 hrs. The solid portion was filtered off and the filtrate was concentrated to give the product as white solid (98% yield). $^1$H NMR (300 MHz, CDCl$_3$) δ3.94(s, 3H), 7.46(s, 1H), 7.72(d, J=8 Hz, 2H), 8.32(d, J=8 Hz, 2H). MS (NH$_3$-CI) Calc. for (M+1)$^+$: 161. Found: 161.

Part B. Isobutyl cis-[2-methyl-3-(4-cyanophenyl) isoxazolidin-5-yl]acetate

A solution of C-(4-cyanophenyl)-N-methylnitrone (1 g, 6.3 mmol) in vinyl acetate isobutyl ester (10 ml) was heated at 100° C. for 20 hrs, and then concentrated. The residue was chromatographed with CH$_2$Cl$_2$/MeOH as eluent to give the cis isomer (880 mg, 46% yield) and the trans (50 mg, 2.6%), along with a cis and trans mixture (630 mg, 33%). $^1$H NMR (300 MHz, CDCl$_3$) δ0.90 (d, J=6, 6H), 1.98(m, 2H), 2.60(m, 1H), 2. 62(s, 3H), 2.90(m, 2H), 3.68(t, J=5, 1H), 3.90(m, 2H), 4.68(m, 1H); MS (NH$_3$-CI) Calc. for (M+1)$^+$: 303. Found: 303.

Part C. [2-methyl-3(S)-(4-cyanophenyl) isoxazolidin-5(R)-yl]acetic acid

The above cis racemic ester (5.0 g) was slurred in 360 ml of phosphate buffer (PH=7.2) at 50° C. with 2.5 g of Lipase AK. After 24 hrs, additional 3.0 g of Lipase AK was added. After stirring at 50° C. for additional 24 hrs, the mixture was acidified to a PH of 2.0, and then filtered. The aqueous solution was extracted with EtOAc. The combined EtOAc solution was extracted with saturated NaHCO3, washed with brine, then dried over Na2SO4. After concentration, 2.50 g of isobutyl 2-[2-methyl-3(R)-(4-cyanophenyl) isoxazolidin-5(S)-yl]acetate with an e.e. of >85% was obtained as a thick oil. The aqueous NaHCO3 solution was acidified to a PH of 3.0 and then extracted with EtOAc. The organic phase was dried over Na2SO4. After concentration, 1.4 g of 2-[2-methyl-3((S)-(4-cyanophenyl)-isoxazolidin-5 (R)-yl]acetic acid with an e.e. of 95% was obtained as an solid. $^1$H NMR (300 MHz, CDCl$_3$) δ0.90 (d, J=6, 6H), 1.98(m, 2H), 2.60(m, 1H), 2.62(s, 3H), 2.90(m, 2H), 3.68(t, J=5, 1H), 3.90(m, 2H), 4.68(m, 1H); MS (NH$_3$—CI) Calc. for (M+1)$^+$: 303. Found: 303.

Part D: 3-[2-[2-methyl-3(S)-(4-cyanophenyl)-isoxazolidin-5(R)-yl]acetyl]aminopropionic acid methyl ester To a mixture of 2-[2-methyl-3(S)-(4-cyanophenyl)-isoxazolidin-5(R)-yl]acetic acid (500 mg, 2.0 mmol), b-alanine methyl ester HCl salt (314 mg, 2.4 mmol) and triethylamine (1.7 ml, 12 mmol) in DMF (7 ml), cooled with ice-water, was added PyBOP (1,18 g, 2.0 mmol). After stirring for 12 hrs, the reaction mixture was diluted with ethyl acetate and washed with dilute NaHCO$_3$ and brine, then dried. Concentration followed by chromatography with a mixture of EtOAc and hexane as the eluent gave the product as an amorphous solid (660 mg, 98% yield).$^1$H NMR (300 MHz, CDCl$_3$) δ2.00 (m, 1H), 2.40(dd, 1H), 2.56(t, 2H), 2.60(s, 3H), 2.68(dd, 1H), 2.94(m, 1H), 3.54(qt, 2H), 3.68(t, 1H), 3.70(s, 3H), 4.60(m, 1H), 6.60(s, 1H), 7.46(d, 2H), 7.64(d, 2H); MS (ESI) Calc. for (M+1)$^+$: 332. Found: 332.

Part E. 3-[[4(S)-(4-cyanophenyl)tetrahydro-3-methyl-2-oxo-2H-1,3-oxazin-6(R)-yl]acetyl] aminopropionic acid methyl ester 3-[2-[2-methyl-3(S)-(4-cyanophenyl)-isoxazolidin-5(R)-yl]acetyl]aminopropionic acid methyl ester (650 mg, 1.87 mmol) was dissolved in acetic acid (15 ml) and zinc (1.8 g, 27.7 mmol) was added. The resulting suspension was stirred vigorously at rt for 8 hrs, then was filtered. The filtration was evaporated to dryness. The residue was dissolved in aqueous NaHCO3(10 ml) and the cloudy solution was evaporated to dyness again. The remaining solid was extracted with ethyl acetate. Removal of ethyl acetate gave the 1,3-aminoalcohol as an oil, which was directly used in the next reaction.

The above 1,3-aminoalcohol was dissolved in anhydrous THF(15 ml) and CDI(370 mg, 2.2 mmol) was added. The solution was stirred overnigt at rt. After evaportation, the residue was taken up in ethyl acetate (100 ml). The ethyl acetate solution was washed successively with 1N HCl, dilute NaHCO3 and brine, and the dried over Na2SO4. Evaporation followed by chromatography using a mixture of merthylene chloride and methanol gave the product as an amorphous solid (450 mg, 63% yield after two steps). $^1$H NMR (300 MHz, CDCl$_3$) δ1.84(qt, 1H), 2.46(m, 2H), 2.54 (t, 2H), 2.64(dd, 1H), 2.72(s, 3H), 3.50(qt, 2H), 3.70(s, 3H), 4.58(dd, 1H), 4.80(m, 1H), 6.38(t, 1H), 7.28(d, 2H), 7.70(d, 2H); MS (ESI) Calc. for (M+1)$^+$: 360. Found: 360.

Part F. 3-[[4(S)-[4-(aminoiminomethyl)phenyl] tetrahydro-3-methyl-2-oxo-2H-1,3-oxazin-6(R)-yl] acetyl]aminopropionic acid methyl ester Dry HCl gas was bubled through a solution of 3-[[4(S)-(4-cyanophenyl)tetrahydro-3-methyl-2-oxo-2H-1,3-oxazin-6(R)-yl]acetyl]aminopropionic acid methyl ester (125 mg 0.35 mmol) in dry CHCl$_3$ containing anhydrous methanol (23 mg, 0.70 mmol), cooled with salt ice-water bath, at 0° C. for 5 hrs. The resulting solution was then kept at 0° C. for 6 hrs and at 15° C. for 12 hrs. The flammable portion was removed and the residue was dissolved in anhydrous methanol (3 ml) followed by addition of ammonium bicarbonate (84 mg, 0.88 mmol). After stirring at rt for 4 hrs, the mixture was concentrated and purified by flush chromatography over silica gel using a mixture of methylene chloride and methanol as the eluent to give a white amorphous solid (85 mg, 64% yield).$^1$H NMR (300 MHz, CD$_3$OD) δ1.90 (m, 1H), 1.22(m, 2H), 2.50(t, 2H), 2.60(dd, 1H), 2.66(s, 3H), 3.40(m, 2H), 3.60(s, 3H), 4.80(m, 2H), 7.54(d, 2H), 7.84(d, 2H); MS (ESI) Calc. for (M+1)$^+$: 377. Found: 377.

Part G. 3-[[4(S)-[4-(aminoiminomethyl)phenyl] tetrahydro-3-methyl-2-oxo-2H-1,3-oxazin-6(R)-yl] acetyl]aminopropionic acid HCl salt 3-[[4(S)-[4-(aminoiminomethyl)phenyl]tetrahydro-3-methyl-2-oxo-2H-1,3-oxazin-6(R)-yl]acetyl] aminopropionic acid methyl ester (70 mg, 0.19 mmol) was dissolved in 4N Hcl (3 ml). The resulting solution was stirred at rt for 36 hrs and then concentrated to yield the acid as an amorphous solid (60 mg, 90% yield). The acid was further purified by reverse HPLC using water and 0.1% TFA in acetonitrile as eluent. $^1$H NMR (300 MHz, CD$_3$OD) δ1.94 (m, 1H), 1.24(m, 2H), 2.60(t, 2H), 2.66(dd, 1H), 2.70(s, 3H), 3.40(m, 2H), 4.85(m, 2H), 7.54(d, 2H), 7.84(d, 2H);MS (ESI) Calc. for (M+1)$^+$: 363. Found: 363.

EXAMPLE 3

3-[[4(R)-[4-(aminoiminomethyl)phenyl]tetrahydro-3-methyl-2-oxo-2H-1,3-oxazin-6(S)-yl]acetyl]amino propionic acid HCl salt This compound was prepared from isobutyl 2-[2-methyl-3(R)-(4-cyanophenyl)isoxazolidin-5(S)-yl]acetate. Its synthesis is similar to that of Example 1. $^1$H NMR (300 MHz, CD$_3$OD) δ1.96 (m, 1H), 1.20(m, 2H), 2.62(t, 2H), 2.68(dd, 1H), 2.76(s, 3H), 3.50(m, 2H), 4.80(m, 2H), 7.48(d, 2H), 7.86(d, 2H); MS (ESI) Calc. for (M+1)$^+$: 363. Found: 363.

EXAMPLE 4

Trans-3-[[4-[4-(aminoiminomethyl)phenyl] tetrahydro-3-methyl-2-oxo-2H-1,3-oxazin-6-yl] acetyl]amino propionic acid HCl salt This compound was prepared from isobutyl trans-2-[2-methyl-3-(4-cyanophenyl)isoxazolidin-5-yl]acetate. Its synthesis is similar to that of Example 1. $^1$H NMR (300 MHz, CD$_3$OD) δ2.26 (m, 6H), 2.90(s, 3H), 3.40(m, 2H), 4.56(m, 1H), 4.80(m, 1H), 7.50(d, 2H), 7.86(d, 2H); MS (ESI) Calc. for (M+1)$^+$: 363. Found: 363.

EXAMPLE 5

3(R)-[[4(S)-[4-(aminoiminomethyl)phenyl] tetrahydro-3-methyl-2-oxo-2H-1,3-oxazin-6(R)-yl] acetyl]aminobutyric acid HCl salt This compound was prepared analogously to Example 1. $^1$H NMR (300 MHz, DMSO-d$_6$) δ1.04 (d, 3H),1.76, dd, 1H), 2.20–2.50(m, 5H), 2.70(s, 3H), 4.20(m, 1), 4.70(m, 2H), 7.50(d, 2H), 7.80(d, 2H), 8.00(d, 1H). MS(ESI) Calc. for (M+1)+: 377. Found: 377.

EXAMPLE 18

3(R)-[[4(S)-[4-(aminoiminomethyl)phenyl] tetrahydro-3-methyl-2-oxo-2H-1,3-oxazin-6(R)-yl] acetyl]amino-5-phenylvaleric acid HCl salt This compound was prepared analogously to Example 1. $^1$H NMR (300 MHz, DMSO-d$_6$) δ1.78 (m, 3H), 2.30–2.58 (m, 5H), 2.60(s, 3H), 4.02(m, 1H), 4.70(m, 2H), 7.14(m, 3H), 7.24(m, 2H), 7.50(d, 2H), 7.84(d, 2H), 8.00(d, 1H). MS(ESI) Calc. for (M+1)$^+$: 467. Found: 467.

EXAMPLE 20

3(S)-[[4(S)-[4-(aminoiminomethyl)phenyl] tetrahydro-3-methyl-2-oxo-2H-1,3-oxazin-6(R)-yl] acetyl]amino-3-(pyridin-3-yl)propionic acid HCl salt This compound was prepared analogously to Example 1. $^1$H NMR (300 MHz, CD$_3$OD) δ2.50(qt, 1H), 3.00(dd, lH), 3.30((m, 3H), 3.36(s, 3H), 3.60(d, 2H), 5.48(m, 1H), 6.00 (m, 1H), 8.24(d, 2H), 8.36(m, 1H), 8.60(d, 2H), 8.80(d, 1H), 9.38(d, 1H), 9.40(s, 1H), 9.50(d, 2H); MS(ESI) Calc. for (M+1)hu +: 440. Found: 440.

EXAMPLE 21

3(R)-[[4(S)-[4-(aminoiminomethyl)phenyl] tetrahydro-3-methyl-2-oxo-2H-1,3-oxazin-6(R)-yl] acetyl]amino-3-(pyridin-3-yl)propionic acid HCl salt This compound was prepared analogously to Example 1. $^1$H NMR (300 MHz, CD$_3$OD) δ6 2.00(m, 1H), 2.40(m, 1H), 2.60(m, 2H), 2.64(s, 3H), 2.90(m, 2H), 3.24((m, 1H), 4.80 (m, 1H), 5.40(m, 1H), 7.50(d, 2H), 7.82(d, 2H), 8.00(m, 1H), 8.60(m, 1H), 8.70(m, 1H), 8.88(m, 1H); MS(ESI) Calc. for (M+1)$^+$: 440. Found: 440.

EXAMPLE 24

3(S)-[[4(S)-[4-(aminoiminomethyl)phenyl] tetrahydro-3-methyl-2-oxo-2H-1,3-oxazin-6(R)-yl] acetyl]amino-3-phenylpropionic acid HCl salt This compound was prepared analogously to Example 1. $^1$H NMR (300 MHz, CD$_3$OD) δ1.80(qt, 1H), 2.30(m, 1H), 2.60(m, 2H), 2.66(s, 3H), 2.80(m, 2H), 4.80(m, 2H), 5.30(m, 1H), 7.30(m, 5H), 7.50(d, 2H), 7.80(d, 2H); MS(ESI) Calc. for (M+1)$^+$: 439. Found: 439.

EXAMPLE 25

3(R)-[[4(S)-[4-(aminoiminomethyl)phenyl] tetrahydro-3-methyl-2-oxo-2H-1,3-oxazin-6(R)-yl] acetyl]amino-3-phenylpropionic acid HCl salt This compound was prepared analogously to Example 1. $^1$H NMR (300 MHz, CD$_3$OD) δ1.90(qt, 1H), 2.40–2.70(m, 5H), 2.72(s, 3H), 4.78(m, 2H), 5.38(t, 1H), 7.20–7.40(m, 5H), 7.50(d, 2H), 7.80(d, 2H); MS(ESI) Calc. for (M+1)$^+$: 439. Found: 439.

EXAMPLE 40

3(R)-[[4(S)-[4-(aminoiminomethyl)phenyl] tetrahydro-3-methyl-2-oxo-2H-1,3-oxazin-6(R)-yl] acetyl]amino-4-[(3-dimethylamino)-propyl]amino-4-oxobutanoic acid bis(trifluoroacetate)

This compound was prepared analogously to Example 1. $^1$H NMR (300 MHz, CD$_3$OD) δ5 1.70(m, 2H), 1.90(qt, 1H), 2.38(s, 6H), 2.40–2.70(m, 6H), 2.74(s, 3H), 2.86(dd, 1H), 3.38(m, 2H), 4.60(m, 2H), 4.84(m, 1H), 7.00(d, 1H), 7.50(d, 2H), 7.80(d, 2H); MS(ESI) Calc. for (M+1)$^+$: 491. Found: 491.

EXAMPLE 317

3(R)-[[4(S)-[4-(aminoiminomethyl)phenyl] tetrahydro-3-methyl-2-oxo-2H-1,3-oxazin-6(R)-yl] acetyl]amino-5-indole-3-valeric acid bis (trifluoroacetate)

Part A. t-Butyl [2-methyl-3(S)-(4-cyanophenyl) isoxazolidin-5(R)-yl]acetate

To a solution of [2-methyl-3(S)-(4-cyanophenyl)-isoxazolidin-5(R)-yl]acetic acid (480 mg, 1.95 mmol) in CH$_2$Cl$_2$ (30 ml) cooled in an ice-water bath was added a 1.6M solution of O-tert-butyl-N, N-diisopropylisourea, cat. CuCl (3.7 ml). The resulting mixture was stirred at rt for 48 hrs. After filtration, the fitrate was concentrated in EtOAc and the residue dissolved in EtOAc. The EtOAc solution was washed with brine and then dried over Na$_2$SO$_4$. After contration, the residue was chromatographed with a mixture of EtOAc and hexane to afford 550 mg of the product as a white solid (93%). $^1$H NMR (300 MHz, CDCl$_3$) δ1.44(s, 9H), 1.98(m, 1H), 2.50(dd, 1H), 2.60(s, 3H), 2.80(dd, 1H), 2.98(dt, 1H), 3.70(t, 1H), 4.64(m, 1H), 7.50(d, 2H0, 7.66(d, 2H); MS(ESI) Calc. for (M+1)$^+$: 303. Found: 303.
Part B.

tert-Butyl [4(S)-(4-cyanophenyl)tetrahydro-3-methyl-2-oxo-2H-1,3-oxazin-6(R)-yl]acetate The procedure is similar to Part E of Example 1. $^1$H NMR(300 MHz, CDCl$_3$) δ1.46(s, 9H), 1.84(m, 1H), 2.50(m, 2H), 2.76(s, 3H), 2.80(dd, 1H), 4.60(dd, 1H, 4.70(m, 1H), 7.40(d, 2H), 7.70(d, 2H); MS(ESI) Calc. for (M+1)$^+$: 331. Found: 331.
Part C.

[4(S)-(4-cyanophenyl)tetrahydro-3-methyl-2-oxo-2H-1,3-oxazin-6(R)-yl]acetic acid The above tert-butyl ester(200 mg, 0.61 mmol) was dissolved in CH$_2$Cl$_2$(5 ml) containing 0.25 ml of TFA. The resulting solution was stirred at rt for 24 hrs and then concentrated. The residue was titrated with hexane and pumped to dryness to give 160 mg of the product as a white solid. $^1$H NMR(300 MHz, CDCl$_3$) δ1.90(m, 1H), 2.40(ddd, 1H), 2.66(m, 2H), 2.70(s, 3H), 4.80(m, 2H), 7.48(d, 2H), 7.80(d, 2H); MS(ESI) Calc. for (M+1)$^+$: 275. Found: 275.

Part D. Methyl 1-Boc-indole-3-propionate

To a solution of methyl indole-3-propionate(5.5 g, 27.1 mmol) and Boc$_2$O(9.34 ml, 40.6 mmol) in dry CH$_2$Cl$_2$(50 ml) in an ice-water bath was added TEA(5.2 ml, 40.6 mmol) and DMAP(330 mg, 10 mol %). The mixture was then stirred overnight at rt. After removal of CH$_2$Cl$_2$, the oily residue was dissolved in EtOAc and washed with aqueous citric acid, NaHCO$_3$ and brine, then dried over Na$_2$SO$_4$. After concentration and flush chromatography, 7.6 g of oily product was obtained(93%). $^1$H NMR(300 MHz, CDCl$_3$) δ1.68(s, 9H), 2.72(t, 2H), 3.04(t, 2H), 3.70(s, 3H), 7.20–7.40 (m, 3H), 7.54(d, 1H), 8.10(d, 1H); MS(ESI) Calc. for (M+1)$^+$: 304. Found: 304.

Part E. 1-Boc-indole-3-propionaldehyde

To a solution of methyl 1-Boc-indole-3-propionate(2.0 g, 6.6 mmol) in toluene(20 ml) cooled at −78° C. was added a 1.5M toluene solution of DIBAL-H slowly so that the internal temperature was kept below −65° C. After addition, stirring was continued at −78° C. for additional 2 hrs. After quenched with 3 ml of MeOH, the mixture was poured into a NaCl solution and extrated with EtOAc. The combined organic solution was washed with a queous acid , NaHCO3 and bine, then dried over Na$_2$SO$_4$. Flush chromatography gave 1.4 g of oily product. $^1$H NMR(300 MHz, CDCl$_3$) δ1.68(s, 9H), 2.84(t, 2H), 3.04(t, 2H), 7.20–7.40(m, 3H), 7.52(d, 1H), 8.14(d, 1H), 9.90(s, 1H); MS(ESI) Calc. for (M+1)$^+$: 274. Found: 274.

Part F. t-Butyl E-5-(1-Boc-indole-3-)pent-2-enoate

A mixture of 1-Boc-indole-3-propionaldehyde(530 mg, 1.94 mmol) and (tert-butoxycarbonylmethene) triphenylphosphorane(880 mg, 2.33 mmol) in toluene(10 ml) was stirred at rt for 24 hrs. The reaction was then worked up as usual. Chromatography with hexane and ethyl acetate (19:1) gave 610 mg of the desired product as an oil(85%). $^1$H NMR(300 MHz, CDCl$_3$) δ1.50(s, 9H), 1.70(s, 9H), 2.60(qt, 2H), 2.84(t, 2H), 5.82(d, 1H), 6.96(dt, 1H), 7.20–7.40(m, 3H), 7.50(d, 1H), 8.10(d, 1H); MS(ESI) Calc. for (M+1)$^+$: 372. Found: 372.

Part G. 3(R)-3-Amino-5-(1-Boc-2,3-dihydroindole-3-)valeric acid tert-butyl ester This b-aminoester was similarly prepared according the method of Davis(*J. Chem. Soc. Perkin Trans I* 1994, 836), obtained as a 1:1 mixture of the two diastereomers. MS(ESI) Calc. for (M+1)$^+$: 389. Found: 389.

Part H. 3(R)-[[4(S)-(4-cyanophenyl)tetrahydro-3-methyl-2-oxo-2H-1,3-oxazin-6(R)-yl]acetyl]amino-5-(1-Boc-2,3-dihydroindole-3-)valeric acid tert-butyl ester To a mixture of [4(S)-(4-cyanophenyl)tetrahydro-3-methyl-2-oxo-2H-1,3-oxazin-6(R)-yl]acetic acid(164 mg, 0.60 mmol), 3(R)-3-Amino-5-(1-Boc-2,3-dihydroindole-3-) valeric acid tert-butyl ester(240 mg, 0.60 mmol) and triethylamine(0.42 ml, 3.0 mmol) in DMF(5 ml), cooled in an ice-water bath, was added PyBOP(380 mg, 0.66 mmol).

After stirring for 12 hrs, the reaction mixture was diluted with ethyl acetate and washed with dilute NaHCO$_3$ and brine, then dried. Concentration followed by chromatography with a mixture of EtOAc and hexane as the eluent gave the product as an amorphous solid(270 mg, 270% yield). It was a 1:1 mixture of the two diasteromers. MS(ESI) Calc. for (M+1)$^+$: 647. Found: 647.

Part H-2. 3(R)-[[4(S)-(4-cyanophenyl)tetrahydro-3-methyl-2-oxo-2H-1,3-oxazin-6(R)-yl]acetyl]amino-5-(1-Boc-indole-3-)valeric acid tert-butyl ester A solution of 3(R)-[[4(S)-(4-cyanophenyl)tetrahydro-3-methyl-2-oxo-2H-1,3-oxazin-6(R)-yl]acetyl]amino-5-(1-Boc-2,3-dihydroindole-3-)valeric acid tert-butyl ester(102 mg, 0.16 mmol), DDQ(43 mg, 0.19 mmol) in toluene(5 ml) was stirred at rt for 24 hrs. The reaction was worked up as usual. Chromatography with CH$_2$Cl$_2$ and MeOH(50:1) gave the product(85 mg, 84%). $^1$H NMR(300 MHz, CDCl$_3$) d 1.46(s, 9H), 1.68(s, 9H), 1.80(qt, 1H), 1.96(m, 2H), 2.40–2.56(m, 4H), 2.68(m, 3H), 1.70(s, 3H), 4.34(m, 1H), 4.56(dd, 1H), 4.78(m, 1H), 6.56(d, 1H), 7.16–7.48(m, 5H), 7.60(d, 2H), 8.10(d, 1H); MS(ESI) Calc. for (M+1)$^+$: 645. Found: 645.

Part I. 3(R)-[[4(S)-[4-(aminoiminomethyl)phenyl]tetrahydro-3-methyl-2-oxo-2H-1,3-oxazin-6(R)-yl]acetyl]amino-5-indole-3-valeric acid tert-butyl ester H$_2$S(g) was bubbled into a solution of 3(R)-[[4(S)-(4-cyanophenyl)tetrahydro-3-methyl-2-oxo-2H-1,3-oxazin-6(R)-yl]acetyl]amino-5-(1-Boc-indole-3-)valeric acid tert-butyl ester(80 mg, 0.12 mmol) in Pyr/TEA(4.8 ml, 5:1) until saturation. The solution was then sealed and stirred at rt overnight. After evaporation, the yellow solid was pumped to dryness to give the corresponding thioamide. MS(ESI) Calc. for (M+23)$^+$: 701. Found: 701.

The above thioamide was dissolved in acetone(5 ml) containing 0.1 ml of iodomethane. The resulting solution was heated at 50° C. for 1.5 hrs. Evaporation gave the corresponding thioimidate as an amorphous solid which was dissolved in dry MeOH(3 ml) followed by addition of ammonium acetate(14 mg). The resulting mixture was stirred at 70° C. for 4 hrs, and then worked up as usual. Chromatography with a mixture of CH$_2$Cl$_2$ and MeOH gave the amidine as a yellow powder(60 mg, 74%). $^1$H NMR(300 MHz, CD$_3$OD) δ1.48(s, 9H), 1.64(s, 9H), 1.80–2.00(m, 2H), 2.40–2.60(m, 3H), 2.64(s, 3H), 2.70(m, 3H), 4.50(m, 1H), 4.80(m, 2H), 7.18(t, 1H), 7.24(t, 1H), 7.40–7.50(m, 4H), 7.80(d, 2H), 8.08(d, d); MS(ESI) Calc. for (M+1)$^+$: 660. Found: 660.

Part J. 3(R)-[[4(S)-[4-(aminoiminomethyl)phenyl]tetrahydro-3-methyl-2-oxo-2H-1.3-oxazin-6(R)-yl]acetyl]amino-5-indole-3-valeric acid bis (trifluoroacetate)

3(R)-[[4(S)-[4-(aminoiminomethyl)phenyl]tetrahydro-3-methyl-2-oxo-2H-1,3-oxazin-6(R)-yl]acetyl]amino-5-indole-3-valeric acid tert-butyl ester(50 mg, 0.076 mmol) was mixed with TFA(0.25 ml) in dry CH$_2$Cl$_2$ (5 ml). The mixture was stirred overnight at rt, and then evaporated to dryness. The residue was purified by reverse HPLC using water and 0.1% TFA fin acetonitrile as eluent. MS(ESI) Calc. for (M+1)$^+$: 506. Found: 506.

EXAMPLE 318

3-[[4(S)-[4-(aminoiminomethyl)phenyl]tetrahydro-3-benzyl-2-oxo-2H-1 3-oxazin-6(R)-yl]acetyl] aminopropionic acid HCl salt This compound was prepared analogously to Example 1. $^1$H NMR(300 MHz, CD$_3$OD) δ2.00(qt, 1H), 2.40(dd, 1H), 2.50(m, 3H), 2.60(dd, 1H), 3.40(m, 2H), 3.60(d, 1H), 4.62 (dd, 1H), 4.74(m, 1H), 5.04(d, 1H), 7.04(m, 2H), 7.289m, 3H), 7.44(d, 2H), 7.809d, 2H); MS(ESI) Calc. for (M+1)$^+$: 439. Found: 439.

EXAMPLE 319

3-[[4(R)-[4-(aminoiminomethyl)phenyl]tetrahydro-3-benzyl-2-oxo-2H-1,3-oxazin-6(S)-yl]acetyl] aminopropionic acid HCl salt This compound was prepared analogously to Example 1. $^1$H NMR(300 MHz, CD$_3$OD) δ1.98(qt, 1H), 2.40(dd, 1H), 2.50(m, 3H), 2.60(dd, 1H), 3.40(m, 2H), 3.60(d, 1H), 4.62 (dd, 1H), 4.74(m, 1H), 5.04(d, 1H), 7.04(m, 2H), 7.289m, 3H), 7.44(d, 2H), 7.809d, 2H); MS(ESI) Calc. for (M+1)$^+$: 439. Found: 439.

EXAMPLE 320

3(R)-[[4(S)-[4-(aminoiminomethyl)phenyl] tetrahydro-3-benzyl-2-oxo-2H-1,3-oxazin-6(R)-yl] acetyl]aminobutyric acid HCl salt Part A. [3-(4-cyanophenyl)isoxazolin-5(R)-yl]acetic acid This acid was prepared according to the method of Zhang(Tetrahedron Lett. 1996. 37, 4455.).

Part B. tert-Butyl [3-(4-cyanophenyl)isoxazolin-5(R)-yl]acetate

To a suspension of [3-(4-cyanophenyl)isoxazolin-5(R)-yl] acetic acid(500 mg, 2.17 mmol) in CH$_2$Cl$_2$ (20 ml) cooled in an ice-water bath was added a 1.6M solution of O-tert-butyl-N, N-diisopropylisourea, cat. CuCl(4 ml). The resulting mixture was stirred at rt for 48 hrs and then filted. The fitrate was concentrated and the residue dissolved in EtOAc. The EtOAc solution was washed with brine and then dried over Na2SO4. After concentration, the residue was chromatographed with a mixture of EtOAc and hexane to afford 600 mg of the product as a white solid(96%). $^1$H NMR(300 MHz, CDCl$_3$) δ1.48(s, 9H), 2.60(dd, 1H), 2.60(dd, 1H), 3.16(dd, 1H), 3.52(dd, 1H), 5.169m, 1H0, 7.70(d, 2H), 7.78(d, 2H); MS(ESI) Calc. for (M−1)$^+$: 285. Found: 285.

Part C. tert-Butyl [4(S)-(4-cyanophenyl)tetrahydro-3-benzyl-2-oxo-2H-1,3-oxazin-6(R)-yl]acetate A mixture of tert-Butyl [3-(4-cyanophenyl)isoxazolin-5 (R)-yl]acetate(600 mg, 2.1 mmol), Zn(2.02 g, 31.5 mmol) in HOAc(10 ml) was vigorously stirred overnight at rt. After removal of excess Zn by filtration, the solution was concentrated and pumped to dryness to give the corresponding 1,3-aminoalcohol. MS(ESI) Calc. for (M+1)$^+$: 291. Found: 291.

The above 1.3-aminoalcohol was dissolved in DCE(8 ml). Benzaldehyde(0.37 ml, 3.6 mmol), HOAc(0.2 ml, 3.6 mmol) and NaB(AcO)$_3$H(770 mg, 3.6 mmol) were added successively. The resulting mixture was stirred at rt for 2 hrs. After removal of DCE, the residue was dissolved on EtOAc and washed with NaHCO3, brine, then dried over Na$_2$SO$_4$. After concentration, the oily residue was filtered through a short pad of Silica gel using a mixture of hexane and EtOAc as the eluent to afford the desired N-benzyl-1,3-aminoalcohol as an oil. MS(ESI) Calc. for (M+1)$^+$: 381. Found: 381.

The N-benzyl-1,3-aminoalcohol obtained above was mixed with CDI(340 mg, 2.1 mmol) in dry THF(12 mmol).

The solution was stirred at rt for 12 hrs and then at refluxing for 24 hrs. After removal of THF, the residue was worked up as usual. Chromatography with a mixture of EtOAC and hexane(1:1) gave 300 mg of the desired product(35%). $^1$H NMR(300 MHz, CDCl$_3$) δ1.44(s, 9H), 1.86(qt, 1H), 1.42(m, 2H), 2.80(d, 1H), 3.50(d, d, 1H), 4.40(dd, 1H), 4.60(m, 1H), 5.26(d, 1H), 7.02(m, 2H), 7.28(m, 5H), 7.68(d, 2H); MS(ESI) Calc. for (M+1)$^+$: 407. Found: 407.

Part D. [4(S)-(4-cyanophenyl)tetrahydro-3-benzyl-2-oxo-2H-1,3-oxazin-6(R)-yl]acetic acid The above tert-butyl ester(240 mg, 0.59 mmol) was dissolved in CH$_2$Cl$_2$(5 ml) containing 0.25 ml of TFA. The resulting solution was stirred at rt for 24 hrs and then concentrated. The residue was titrated with hexane and pumped to dryness to give 200 mg of the product as a amorphous solid. $^1$H NMR(300 MHz, CDCl$_3$) d 1.98(qt, 1H), 2.40(m, 1H), 2.64(dd, 1H), 2.90(dd, 1H), 3.58(d, 1H), 4.44(dd, 1H), 4.76(m, 1H), 5.20(d, 1H), 7.00(m, 2H), 7.30 (m, 5H), 7.70(d, 2H); MS(ESI) Calc. for (M+1)$^+$: 351. Found: 351.

Part E. 3(R)-[[4(S)-(4-cyanophenyl tetrahydro-3-benzyl-2-oxo-2H-1,3-oxazin-6(R)-yl]acetyl]aminobutyric acid benzyl ester The procedure was similar to Part D of Example 1. $^1$H NMR (300 MHz, CDCl$_3$) δ1.24(d, 3H), 1.90(qt, 1H), 2.40 (m, 2H), 2.56(d, 2H), 2.60(dd, 1H), 3.50(d, 1H), 4.40(m, 2H0, 4.66(m, 1H), 5.10(s, 2H), 5.20(d, 1H), 6.30(d, 1H), 7.00(m, 2H), 7.20–7.40(m, 10H), 7.649d, 2H); MS(ESI) Calc. for (M+1)$^+$: 526. Found: 526.

Part F. 3(R)-[[4(S)-[4-(aminoiminomethyl)phenyl]tetrahydro-3-benzyl-2-oxo-2H-1,3-oxazin-6(R)-yl]acetyl]aminobutyric acid methyl ester The procedure is similar to Part F of Example 1. $^1$H NMR (300 MHz, CD$_3$OD) δ1.26(d, 3H), 1.90(m, 1H), 2.20–2.60 (m, 5H), 3.40(s, 3H), 3.50(d, 1H), 4.40(m, 2H), 4.60(m, 1H), 5.20(d, 1H), 7.05(m, 2H), 7.30–7.50(m, 5H), 7.80(d, 2H); MS(ESI) Calc. for (M+1)$^+$: 543. Found: 543.

Part G. 3(R)-[[4(S)-[4-(aminoiminomethyl)phenyl]tetrahydro-3-benzyl-2-oxo-2H-1.3-oxazin-6(R)-yl]acetyl]aminobutyric acid The procedure was similar to Part G of Example 1. $^1$H NMR (300 MHz, CD$_3$OD) δ1.26(d, 3H), 1.90(m, 1H), 2.40(m, 2H), 2.60(m, 3H), 3.50(d, 1H), 4.50(m, 2H), 4.70 (m, 1H), 5.20(d, 1H), 7.04(m, 2H), 7.40(m, 5H), 7.80(d, 2H); MS(ESI) Calc. for (M+1)$^+$: 453. Found: 453.

EXAMPLE 340

[N-[[4(S)-[4-(N-butylaminoiminomethyl)phenyl]tetrahydro-3-benzyl-2-oxo-2H-1,3-oxazin-6(R)-yl]acetyl]piperidin-4-yl]acetic acid HCl salt This compound was prepared analogously to Example 320. $^1$H NMR(300 MHz, CD$_3$OD) δ1.10–1.30(m, 2H), 1.80(m, 3H), 2.04(m, 1H), 2.24(m, 2H), 2.60(m, 3H), 2.90 (dd, 1H), 3.04(m, 1H), 3.50(d, 1H), 3.80(m, 1H), 4.50(m, 2H), 4.70(m, 1H), 5.26(d, 1H), 7.02(m, 2H), 7.40(m, 5H), 7.80(d, 2H); MS(ESI) Calc. for (M+1)$^+$: 493. Found: 493.

EXAMPLE 411

3(R)-[[4(S)-[4-(N-butylaminoiminomethyl)phenyl]tetrahydro-3-methyl-2-oxo-2H-1,3-oxazin-6(R)-yl]acetyl]amino-5-phenylvaleric acid HCl salt T his compound was prepared analogously to Example 1. $^1$H NMR(300 MHz, CD$_3$OD) δ1.00(t, 3H), 1.46(m, 2H), 1.66–2.00(m, 5H), 2.40–2.60(m, 7H), 2.65(s, 3H), 3.40(t, 2H), 4.20(m, 1H), 4.80(m, 2H), 7.10–7.26(m, 5H), 7.50(d, 2H), 7.70(d, 2H), 8.08(m, 1H). MS(ESI) Calc. for (M+1)$^+$: 523. Found: 523.

EXAMPLE 511

3-[[2-methyl-3(S)-[4-(aminoiminomethyl)phenyl]-isoxazolidin-5(R)-yl]acetyl]aminopropionic acid HCl salt This compound was prepared from 3-[[2-methyl-3(S)-(4-cyanophenyl)-isoxazolidin-5(R)-yl]acetyl]aminopropionic acid methyl ester through a standard Pinner reaction and a hydrolesis. $^1$H NMR(300 MHz, CD30D) δ2.02(m, 1H), 2.44(dd, 1H), 2.50(t, 2H), 2.56(s, 3H), 2.64(dd, 1H), 2.96(m, 1H), 3.40(t, 2H), 3.90(t, 1H), 4.60(m, 1H), 7.60(d, 2H), 7.8(d, 2H); MS(ESI) Calc. for (M+1)$^+$: 335. Found:335.

EXAMPLE 512

3-[[2-methyl-3(R)-[4-(aminoiminomethyl)phenyl]-isoxazolidin-5(S)-yl]acetyl]aminopropionic acid HCl salt This compound was prepared analogously to Example 511. $^1$H NMR(300 MHz, CD$_3$OD) δ2.12(m, 1H), 2.42(dd, 1H), 2.50(t, 2H), 2.58(s, 3H), 2.66(dd, 1H), 2.94(m, 1H), 3.40(t, 2H), 3.90(t, 1H), 4.60(m, 1H), 7.60(d, 2H), 7.8(d, 2H); MS(ESI) Calc. for (M+1)$^+$: 335. Found:335.

EXAMPLE 513

3(R)-[[2-methyl-3(R)-[4-(aminoiminomethyl)phenyl]-isoxazolidin-5(S)-yl]acetyl]aminobutyric acid HCl salt This compound was prepared analogously to Example 511. $^1$H NMR(300 MHz, CD$_3$OD) δ1.22(d, 3H), 2.00(m, 1H), 2.40(dd, 1H), 2.50(d, 2H), 2.62(s, 3H), 2.70(m, 1H), 2.90(m, 1H), 3.70(m, 1H), 4.40(m, 1H), 4.60(m, 1H), 7.64 (d, 2H), 7.88(d, 2H); MS(ESI) Calc. for (M+1)$^+$: 349. Found:349.

EXAMPLE 774

[N-[[4(S)-[4-(N-butylaminoiminomethyl)phenyl]tetrahydro-3-methyl-2-oxo-2H-1,3-oxazin-6(R)-yl]acetyl]piperidin-4-yl]acetic acid HCl salt This compound was prepared analogously to Example 1. $^1$H NMR(300 MHz, CD$_3$OD) δ1.04–1.40(m, 4H), 1.72–2.10 (m, 4H), 2.24(m, 2H), 2,50(m, 1H), 2.70(s, 3H), 2.90(m, 1H), 3.10(m, 1H), 3.96(m, 1H), 4.50(m, 1H), 4.80(m, 2H), 7.54(d, 2H), 7.86(d, 2H); MS(ESI) Calc. for (M+1)$^+$: 417. Found: 417.

TABLE 1

$R^1-A-(CH_2)_m$—[ring with $R^3$, $N$, $X$, $O$]—$(CH_2)_n$—C(O)—N($R^5$)—CH($R^8$)—C(O)Y

| Ex No. | R¹—A | m | R³ | X | n | R⁵ | R⁸ | Y | MS [(M + 1)⁺] |
|---|---|---|---|---|---|---|---|---|---|
| 1 | 4-amidinophenyl | 0 | Me | C(O) | 1 | H | H | OH | 363 |
| 2 | 4-amidinophenyl | 0 | Me | C(O) | 1 | H | H | OMe | |
| 3 | 4-amidinophenyl 4-R, 6-S | 0 | Me | C(O) | 1 | H | H | OH | 363 |
| 4 | 4-amidinophenyl trans, racemate | 0 | Me | C(O) | 1 | H | H | OH | 363 |
| 5 | 4-amidinophenyl | 0 | Me | C(O) | 1 | H | Me | OH | 377 |
| 6 | 4-amidinophenyl | 0 | Me | C(O) | 1 | H | Et | OH | |
| 7 | 4-amidinophenyl | 0 | Me | C(O) | 1 | H | Propyl | OH | |
| 8 | 4-amidinophenyl | 0 | Me | C(O) | 1 | H | butyl | OH | |
| 9 | 4-amidinophenyl | 0 | Me | C(O) | 1 | H | hexyl | OH | |
| 10 | 4-amidinophenyl | 0 | Me | C(O) | 1 | H | cyclopropyl | OH | |
| 11 | 4-amidinophenyl | 0 | Me | C(O) | 1 | H | cyclohexyl | OH | |
| 12 | 4-amidinophenyl | 0 | Me | C(O) | 1 | H | acetynyl | OH | |
| 13 | 4-amidinophenyl | 0 | Me | C(O) | 1 | H | methylacetynyl | OH | |
| 14 | 4-amidinophenyl | 0 | Me | C(O) | 1 | H | cyclopropylacetynyl | OH | |
| 15 | 4-amidinophenyl | 0 | Me | C(O) | 1 | H | ethylacetynyl | OH | |
| 16 | 4-amidinophenyl | 0 | Me | C(O) | 1 | H | butylacetynyl | OH | |
| 17 | 4-amidinophenyl | 0 | Me | C(O) | 1 | H | vinyl | OH | |
| 18 | 4-amidinophenyl | 0 | Me | C(O) | 1 | H | phenethyl | OH | 467 |
| 19 | 4-amidinophenyl | 0 | Me | C(O) | 1 | H | phenylmethyl | OH | |
| 20 | 4-amidinophenyl | 0 | Me | C(O) | 1 | H | 3-pyridinyl | OH | 440 |
| 21 | 4-amidinophenyl 4-S, 6-R, 3'-R | 0 | Me | C(O) | 1 | H | 3-pyridinyl | OH | 440 |
| 22 | 4-amidinophenyl | 0 | Me | C(O) | 1 | H | 2-pyridinyl | OH | |
| 23 | 4-amidinophenyl | 0 | Me | C(O) | 1 | H | 4-pyridinyl | OH | |
| 24 | 4-amidinophenyl | 0 | Me | C(O) | 1 | H | phenyl | OH | 439 |
| 25 | 4-amidinophenyl 4-S, 6-R, 3'-R | 0 | Me | C(O) | 1 | H | phenyl | OH | 439 |
| 26 | 4-amidinophenyl | 0 | Me | C(O) | 1 | H | 2-fluorophenyl | OH | |
| 27 | 4-amidinophenyl | 0 | Me | C(O) | 1 | H | 3-fluorophenyl | OH | |
| 28 | 4-amidinophenyl | 0 | Me | C(O) | 1 | H | 4-fluorophenyl | OH | |
| 29 | 4-amidinophenyl | 0 | Me | C(O) | 1 | H | 2-methylphenyl | OH | |
| 30 | 4-amidinophenyl | 0 | Me | C(O) | 1 | H | 3-methylphenyl | OH | |
| 31 | 4-amidinophenyl | 0 | Me | C(O) | 1 | H | 4-methylphenyl | OH | |
| 32 | 4-amidinophenyl | 0 | Me | C(O) | 1 | H | 2-methoxyphenyl | OH | |
| 33 | 4-amidinophenyl | 0 | Me | C(O) | 1 | H | 3-methoxyphenyl | OH | |
| 34 | 4-amidinophenyl | 0 | Me | C(O) | 1 | H | 4-methoxyphenyl | OH | |
| 35 | 4-amidinophenyl | 0 | Me | C(O) | 1 | H | 2-bromophenyl | OH | |
| 36 | 4-amidinophenyl | 0 | Me | C(O) | 1 | H | CH₃NHC(O) | OH | |
| 37 | 4-amidinophenyl | 0 | Me | C(O) | 1 | H | CH₃CH₂NHC(O) | OH | |
| 38 | 4-amidinophenyl | 0 | Me | C(O) | 1 | H | cyclopropyl-NHC(O) | OH | |
| 39 | 4-amidinophenyl | 0 | Me | C(O) | 1 | H | CH₃OCH₂CH₂NHC(O) | OH | |
| 40 | 4-amidinophenyl | 0 | Me | C(O) | 1 | H | Me₂N(CH₂)₃NHC(O) | OH | 491 |
| 41 | 4-amidinophenyl | 0 | Me | C(O) | 1 | H | PhNHC(O) | OH | |
| 42 | 4-amidinophenyl | 0 | Me | C(O) | 1 | H | 2-MeOPhNH(CO) | OH | |
| 43 | 4-amidinophenyl | 0 | Me | C(O) | 1 | H | Me₂NC(O) | OH | |
| 44 | 4-amidinophenyl | 0 | Et | C(O) | 1 | H | H | OH | |
| 45 | 4-amidinophenyl | 0 | Et | C(O) | 1 | H | H | OMe | |
| 46 | 4-amidinophenyl | 0 | Et | C(O) | 1 | H | Me | OH | |
| 47 | 4-amidinophenyl | 0 | Et | C(O) | 1 | H | Et | OH | |
| 48 | 4-amidinophenyl | 0 | Et | C(O) | 1 | H | Propyl | OH | |
| 49 | 4-amidinophenyl | 0 | Et | C(O) | 1 | H | butyl | OH | |
| 50 | 4-amidinophenyl | 0 | Et | C(O) | 1 | H | hexyl | OH | |
| 51 | 4-amidinophenyl | 0 | Et | C(O) | 1 | H | cyclopropyl | OH | |
| 52 | 4-amidinophenyl | 0 | Et | C(O) | 1 | H | cyclohexyl | OH | |
| 53 | 4-amidinophenyl | 0 | Et | C(O) | 1 | H | acetynyl | OH | |
| 54 | 4-amidinophenyl | 0 | Et | C(O) | 1 | H | methylacetynyl | OH | |
| 55 | 4-amidinophenyl | 0 | Et | C(O) | 1 | H | cyclopropylacetynyl | OH | |
| 56 | 4-amidinophenyl | 0 | Et | C(O) | 1 | H | ethylacetynyl | OH | |
| 57 | 4-amidinophenyl | 0 | Et | C(O) | 1 | H | butylacetynyl | OH | |
| 58 | 4-amidinophenyl | 0 | Et | C(O) | 1 | H | vinyl | OH | |
| 59 | 4-amidinophenyl | 0 | Et | C(O) | 1 | H | phenethyl | OH | |
| 60 | 4-amidinophenyl | 0 | Et | C(O) | 1 | H | phenylmethyl | OH | |
| 61 | 4-amidinophenyl | 0 | Et | C(O) | 1 | H | 3-pyridinyl | OH | |
| 62 | 4-amidinophenyl | 0 | Et | C(O) | 1 | H | 2-pyridinyl | OH | |
| 63 | 4-amidinophenyl | 0 | Et | C(O) | 1 | H | 4-pyridinyl | OH | |
| 64 | 4-amidinophenyl | 0 | Et | C(O) | 1 | H | phenyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 65 | 4-amidinophenyl | 0 | Et | C(O) | 1 | H | 2-fluorophenyl | OH | |
| 66 | 4-amidinophenyl | 0 | Et | C(O) | 1 | H | 3-fluorophenyl | OH | |
| 67 | 4-amidinophenyl | 0 | Et | C(O) | 1 | H | 4-fluorophenyl | OH | |
| 68 | 4-amidinophenyl | 0 | Et | C(O) | 1 | H | 2-methylphenyl | OH | |
| 69 | 4-amidinophenyl | 0 | Et | C(O) | 1 | H | 3-methylphenyl | OH | |
| 70 | 4-amidinophenyl | 0 | Et | C(O) | 1 | H | 4-methylphenyl | OH | |
| 71 | 4-amidinophenyl | 0 | Et | C(O) | 1 | H | 2-methoxyphenyl | OH | |
| 72 | 4-amidinophenyl | 0 | Et | C(O) | 1 | H | 3-methoxyphenyl | OH | |
| 73 | 4-amidinophenyl | 0 | Et | C(O) | 1 | H | 4-methoxyphenyl | OH | |
| 74 | 4-amidinophenyl | 0 | Et | C(O) | 1 | H | 2-bromophenyl | OH | |
| 75 | 4-amidinophenyl | 0 | Et | C(O) | 1 | H | CH₃NHC(O) | OH | |
| 76 | 4-amidinophenyl | 0 | Et | C(O) | 1 | H | CH₃CH₂NHC(O) | OH | |
| 77 | 4-amidinophenyl | 0 | Et | C(O) | 1 | H | cyclopropyl-NHC(O) | OH | |
| 78 | 4-amidinophenyl | 0 | Et | C(O) | 1 | H | CH₃OCH₂CH₂NHC(O) | OH | |
| 79 | 4-amidinophenyl | 0 | Et | C(O) | 1 | H | Me₂N(CH₂)₃NHC(O) | OH | |
| 80 | 4-amidinophenyl | 0 | Et | C(O) | 1 | H | PhNHC(O) | OH | |
| 81 | 4-amidinophenyl | 0 | Et | C(O) | 1 | H | 2-MeOPhNH(CO) | OH | |
| 82 | 4-amidinophenyl | 0 | Et | C(O) | 1 | H | Me₂NHC(O) | OH | |
| 83 | 4-amidinophenyl | 0 | H | C(O) | 1 | H | H | OH | |
| 84 | 4-amidinophenyl | 0 | H | C(O) | 1 | H | H | OMe | |
| 85 | 4-amidinophenyl | 0 | H | C(O) | 1 | H | Me | OH | |
| 86 | 4-amidinophenyl | 0 | H | C(O) | 1 | H | Et | OH | |
| 87 | 4-amidinophenyl | 0 | H | C(O) | 1 | H | Propyl | OH | |
| 88 | 4-amidinophenyl | 0 | H | C(O) | 1 | H | butyl | OH | |
| 89 | 4-amidinophenyl | 0 | H | C(O) | 1 | H | hexyl | OH | |
| 90 | 4-amidinophenyl | 0 | H | C(O) | 1 | H | cyclopropyl | OH | |
| 91 | 4-amidinophenyl | 0 | H | C(O) | 1 | H | cyclohexyl | OH | |
| 92 | 4-amidinophenyl | 0 | H | C(O) | 1 | H | acetynyl | OH | |
| 93 | 4-amidinophenyl | 0 | H | C(O) | 1 | H | methylacetynyl | OH | |
| 94 | 4-amidinophenyl | 0 | H | C(O) | 1 | H | cyclopropylacetynyl | OH | |
| 95 | 4-amidinophenyl | 0 | H | C(O) | 1 | H | ethylacetynyl | OH | |
| 96 | 4-amidinophenyl | 0 | H | C(O) | 1 | H | butylacetynyl | OH | |
| 97 | 4-amidinophenyl | 0 | H | C(O) | 1 | H | vinyl | OH | |
| 98 | 4-amidinophenyl | 0 | H | C(O) | 1 | H | phenethyl | OH | |
| 99 | 4-amidinophenyl | 0 | H | C(O) | 1 | H | phenylmethyl | OH | |
| 100 | 4-amidinophenyl | 0 | H | C(O) | 1 | H | 3-pyridinyl | OH | |
| 101 | 4-amidinophenyl | 0 | H | C(O) | 1 | H | 2-pyridinyl | OH | |
| 102 | 4-amidinophenyl | 0 | H | C(O) | 1 | H | 4-pyridinyl | OH | |
| 103 | 4-amidinophenyl | 0 | H | C(O) | 1 | H | phenyl | OH | |
| 104 | 4-amidinophenyl | 0 | H | C(O) | 1 | H | 2-fluorophenyl | OH | |
| 105 | 4-amidinophenyl | 0 | H | C(O) | 1 | H | 3-fluorophenyl | OH | |
| 106 | 4-amidinophenyl | 0 | H | C(O) | 1 | H | 4-fluorophenyl | OH | |
| 107 | 4-amidinophenyl | 0 | H | C(O) | 1 | H | 2-methylphenyl | OH | |
| 108 | 4-amidinophenyl | 0 | H | C(O) | 1 | H | 3-methylphenyl | OH | |
| 109 | 4-amidinophenyl | 0 | H | C(O) | 1 | H | 4-methylphenyl | OH | |
| 110 | 4-amidinophenyl | 0 | H | C(O) | 1 | H | 2-methoxyphenyl | OH | |
| 111 | 4-amidinophenyl | 0 | H | C(O) | 1 | H | 3-methoxyphenyl | OH | |
| 112 | 4-amidinophenyl | 0 | H | C(O) | 1 | H | 4-methoxyphenyl | OH | |
| 113 | 4-amidinophenyl | 0 | H | C(O) | 1 | H | 2-bromophenyl | OH | |
| 114 | 4-amidinophenyl | 0 | H | C(O) | 1 | H | CH₃NHC(O) | OH | |
| 115 | 4-amidinophenyl | 0 | H | C(O) | 1 | H | CH₃CH₂NHC(O) | OH | |
| 116 | 4-amidinophenyl | 0 | H | C(O) | 1 | H | cyclopropyl-NHC(O) | OH | |
| 117 | 4-amidinophenyl | 0 | H | C(O) | 1 | H | CH₃OCH₂CH₂NHC(O) | OH | |
| 118 | 4-amidinophenyl | 0 | H | C(O) | 1 | H | Me₂N(CH₂)₃NHC(O) | OH | |
| 119 | 4-amidinophenyl | 0 | H | C(O) | 1 | H | PhNHC(O) | OH | |
| 120 | 4-amidinophenyl | 0 | H | C(O) | 1 | H | 2-MeOPhNH(CO) | OH | |
| 121 | 4-amidinophenyl | 0 | H | C(O) | 1 | H | Me₂NHC(O) | OH | |
| 122 | 4-amidinophenyl | 0 | H | C(O) | 1 | Me | H | OH | |
| 123 | 4-amidinophenyl | 0 | H | C(O) | 1 | Me | H | OMe | |
| 124 | 4-amidinophenyl | 0 | H | C(O) | 1 | Me | Me | OH | |
| 125 | 4-amidinophenyl | 0 | H | C(O) | 1 | Me | Et | OH | |
| 126 | 4-amidinophenyl | 0 | H | C(O) | 1 | Me | Propyl | OH | |
| 127 | 4-amidinophenyl | 0 | H | C(O) | 1 | Me | butyl | OH | |
| 128 | 4-amidinophenyl | 0 | H | C(O) | 1 | Me | hexyl | OH | |
| 129 | 4-amidinophenyl | 0 | H | C(O) | 1 | Me | cyclopropyl | OH | |
| 130 | 4-amidinophenyl | 0 | H | C(O) | 1 | Me | cyclohexyl | OH | |
| 131 | 4-amidinophenyl | 0 | H | C(O) | 1 | Me | acetynyl | OH | |
| 132 | 4-amidinophenyl | 0 | H | C(O) | 1 | Me | methylacetynyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 133 | 4-amidinophenyl | 0 | H | C(O) | 1 | Me | cyclopropylacetynyl | OH | |
| 134 | 4-amidinophenyl | 0 | H | C(O) | 1 | Me | ethylacetynyl | OH | |
| 135 | 4-amidinophenyl | 0 | H | C(O) | 1 | Me | butylacetynyl | OH | |
| 136 | 4-amidinophenyl | 0 | H | C(O) | 1 | Me | vinyl | OH | |
| 137 | 4-amidinophenyl | 0 | H | C(O) | 1 | Me | phenethyl | OH | |
| 138 | 4-amidinophenyl | 0 | H | C(O) | 1 | Me | phenylmethyl | OH | |
| 139 | 4-amidinophenyl | 0 | H | C(O) | 1 | Me | 3-pyridinyl | OH | |
| 140 | 4-amidinophenyl | 0 | H | C(O) | 1 | Me | 2-pyridinyl | OH | |
| 141 | 4-amidinophenyl | 0 | H | C(O) | 1 | Me | 4-pyridinyl | OH | |
| 142 | 4-amidinophenyl | 0 | H | C(O) | 1 | Me | phenyl | OH | |
| 143 | 4-amidinophenyl | 0 | H | C(O) | 1 | Me | 2-fluorophenyl | OH | |
| 144 | 4-amidinophenyl | 0 | H | C(O) | 1 | Me | 3-fluorophenyl | OH | |
| 145 | 4-amidinophenyl | 0 | H | C(O) | 1 | Me | 4-fluorophenyl | OH | |
| 146 | 4-amidinophenyl | 0 | H | C(O) | 1 | Me | 2-methylphenyl | OH | |
| 147 | 4-amidinophenyl | 0 | H | C(O) | 1 | Me | 3-methylphenyl | OH | |
| 148 | 4-amidinophenyl | 0 | H | C(O) | 1 | Me | 4-methylphenyl | OH | |
| 149 | 4-amidinophenyl | 0 | H | C(O) | 1 | Me | 2-methoxyphenyl | OH | |
| 150 | 4-amidinophenyl | 0 | H | C(O) | 1 | Me | 3-methoxyphenyl | OH | |
| 151 | 4-amidinophenyl | 0 | H | C(O) | 1 | Me | 4-methoxyphenyl | OH | |
| 152 | 4-amidinophenyl | 0 | H | C(O) | 1 | Me | 2-bromophenyl | OH | |
| 153 | 4-amidinophenyl | 0 | H | C(O) | 1 | Me | CH₃NHC(O) | OH | |
| 154 | 4-amidinophenyl | 0 | H | C(O) | 1 | Me | CH₃CH₂NHC(O) | OH | |
| 155 | 4-amidinophenyl | 0 | H | C(O) | 1 | Me | cyclopropyl-NHC(O) | OH | |
| 156 | 4-amidinophenyl | 0 | H | C(O) | 1 | Me | CH₃OCH₂CH₂NHC(O) | OH | |
| 157 | 4-amidinophenyl | 0 | H | C(O) | 1 | Me | Me₂N(CH₂)₃NHC(O) | OH | |
| 158 | 4-amidinophenyl | 0 | H | C(O) | 1 | Me | PhNHC(O) | OH | |
| 159 | 4-amidinophenyl | 0 | H | C(O) | 1 | Me | 2-MeOPhNH(CO) | OH | |
| 160 | 4-amidinophenyl | 0 | H | C(O) | 1 | Me | Me₂NHC(O) | OH | |
| 161 | 4-amidinophenyl | 0 | c-propyl | C(O) | 1 | H | H | OH | |
| 162 | 4-amidinophenyl | 0 | c-propyl | C(O) | 1 | H | H | OMe | |
| 163 | 4-amidinophenyl | 0 | c-propyl | C(O) | 1 | H | Me | OH | |
| 164 | 4-amidinophenyl | 0 | c-propyl | C(O) | 1 | H | Et | OH | |
| 165 | 4-amidinophenyl | 0 | c-propyl | C(O) | 1 | H | Propyl | OH | |
| 166 | 4-amidinophenyl | 0 | c-propyl | C(O) | 1 | H | butyl | OH | |
| 167 | 4-amidinophenyl | 0 | c-propyl | C(O) | 1 | H | hexyl | OH | |
| 168 | 4-amidinophenyl | 0 | c-propyl | C(O) | 1 | H | cyclopropyl | OH | |
| 169 | 4-amidinophenyl | 0 | c-propyl | C(O) | 1 | H | cyclohexyl | OH | |
| 170 | 4-amidinophenyl | 0 | c-propyl | C(O) | 1 | H | acetynyl | OH | |
| 171 | 4-amidinophenyl | 0 | c-propyl | C(O) | 1 | H | methylacetynyl | OH | |
| 172 | 4-amidinophenyl | 0 | c-propyl | C(O) | 1 | H | cyclopropylacetynyl | OH | |
| 173 | 4-amidinophenyl | 0 | c-propyl | C(O) | 1 | H | ethylacetynyl | OH | |
| 174 | 4-amidinophenyl | 0 | c-propyl | C(O) | 1 | H | butylacetynyl | OH | |
| 175 | 4-amidinophenyl | 0 | c-propyl | C(O) | 1 | H | vinyl | OH | |
| 176 | 4-amidinophenyl | 0 | c-propyl | C(O) | 1 | H | phenethyl | OH | |
| 177 | 4-amidinophenyl | 0 | c-propyl | C(O) | 1 | H | phenylmethyl | OH | |
| 178 | 4-amidinophenyl | 0 | c-propyl | C(O) | 1 | H | 3-pyridinyl | OH | |
| 179 | 4-amidinophenyl | 0 | c-propyl | C(O) | 1 | H | 2-pyridinyl | OH | |
| 180 | 4-amidinophenyl | 0 | c-propyl | C(O) | 1 | H | 4-pyridinyl | OH | |
| 181 | 4-amidinophenyl | 0 | c-propyl | C(O) | 1 | H | phenyl | OH | |
| 182 | 4-amidinophenyl | 0 | c-propyl | C(O) | 1 | H | 2-fluorophenyl | OH | |
| 183 | 4-amidinophenyl | 0 | c-propyl | C(O) | 1 | H | 3-fluorophenyl | OH | |
| 184 | 4-amidinophenyl | 0 | c-propyl | C(O) | 1 | H | 4-fluorophenyl | OH | |
| 185 | 4-amidinophenyl | 0 | c-propyl | C(O) | 1 | H | 2-methylphenyl | OH | |
| 186 | 4-amidinophenyl | 0 | c-propyl | C(O) | 1 | H | 3-methylphenyl | OH | |
| 187 | 4-amidinophenyl | 0 | c-propyl | C(O) | 1 | H | 4-methylphenyl | OH | |
| 188 | 4-amidinophenyl | 0 | c-propyl | C(O) | 1 | H | 2-methoxyphenyl | OH | |
| 189 | 4-amidinophenyl | 0 | c-propyl | C(O) | 1 | H | 3-methoxyphenyl | OH | |
| 190 | 4-amidinophenyl | 0 | c-propyl | C(O) | 1 | H | 4-methoxyphenyl | OH | |
| 191 | 4-amidinophenyl | 0 | c-propyl | C(O) | 1 | H | 2-bromophenyl | OH | |
| 192 | 4-amidinophenyl | 0 | c-propyl | C(O) | 1 | H | CH₃NHC(O) | OH | |
| 193 | 4-amidinophenyl | 0 | c-propyl | C(O) | 1 | H | CH₃CH₂NHC(O) | OH | |
| 194 | 4-amidinophenyl | 0 | c-propyl | C(O) | 1 | H | cyclopropyl-NHC(O) | OH | |
| 195 | 4-amidinophenyl | 0 | c-propyl | C(O) | 1 | H | CH₃OCH₂CH₂NHC(O) | OH | |
| 195 | 4-amidinophenyl | 0 | c-propyl | C(O) | 1 | H | Me₂N(CH₂)₃NHC(O) | OH | |
| 197 | 4-amidinophenyl | 0 | c-propyl | C(O) | 1 | H | PhNHC(O) | OH | |
| 198 | 4-amidinophenyl | 0 | c-propyl | C(O) | 1 | H | 2-MeOPhNH(CO) | OH | |
| 199 | 4-amidinophenyl | 0 | c-propyl | C(O) | 1 | H | Me₂NHC(O) | OH | |
| 200 | 4-amidinophenyl | 0 | Me | C(O) | 0 | H | H | OH | |

TABLE 1-continued

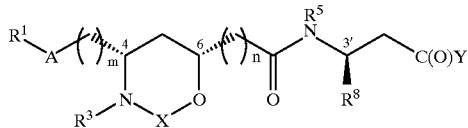

| Ex No. | R¹—A | m | R³ | X | n | R⁵ | R⁸ | Y | MS [(M + 1)⁺] |
|---|---|---|---|---|---|---|---|---|---|
| 201 | 4-amidinophenyl | 0 | Me | C(O) | 0 | H | H | OMe | |
| 201 | 4-amidinophenyl | 0 | Me | C(O) | 0 | H | Me | OH | |
| 203 | 4-amidinophenyl | 0 | Me | C(O) | 0 | H | Et | OH | |
| 204 | 4-amidinophenyl | 0 | Me | C(O) | 0 | H | Propyl | OH | |
| 205 | 4-amidinophenyl | 0 | Me | C(O) | 0 | H | butyl | OH | |
| 206 | 4-amidinophenyl | 0 | Me | C(O) | 0 | H | hexyl | OH | |
| 207 | 4-amidinophenyl | 0 | Me | C(O) | 0 | H | cyclopropyl | OH | |
| 208 | 4-amidinophenyl | 0 | Me | C(O) | 0 | H | cyclohexyl | OH | |
| 209 | 4-amidinophenyl | 0 | Me | C(O) | 0 | H | acetynyl | OH | |
| 210 | 4-amidinophenyl | 0 | Me | C(O) | 0 | H | methylacetynyl | OH | |
| 211 | 4-amidinophenyl | 0 | Me | C(O) | 0 | H | cyclopropylacetynyl | OH | |
| 212 | 4-amidinophenyl | 0 | Me | C(O) | 0 | H | ethylacetynyl | OH | |
| 213 | 4-amidinophenyl | 0 | Me | C(O) | 0 | H | butylacetynyl | OH | |
| 214 | 4-amidinophenyl | 0 | Me | C(O) | 0 | H | vinyl | OH | |
| 215 | 4-amidinophenyl | 0 | Me | C(O) | 0 | H | phenethyl | OH | |
| 216 | 4-amidinophenyl | 0 | Me | C(O) | 0 | H | phenylmethyl | OH | |
| 217 | 4-amidinophenyl | 0 | Me | C(O) | 0 | H | 3-pyridinyl | OH | |
| 218 | 4-amidinophenyl | 0 | Me | C(O) | 0 | H | 2-pyridinyl | OH | |
| 219 | 4-amidinophenyl | 0 | Me | C(O) | 0 | H | 4-pyridinyl | OH | |
| 220 | 4-amidinophenyl | 0 | Me | C(O) | 0 | H | phenyl | OH | |
| 221 | 4-amidinophenyl | 0 | Me | C(O) | 0 | H | 2-fluorophenyl | OH | |
| 222 | 4-amidinophenyl | 0 | Me | C(O) | 0 | H | 3-fluorophenyl | OH | |
| 223 | 4-amidinophenyl | 0 | Me | C(O) | 0 | H | 4-fluorophenyl | OH | |
| 224 | 4-amidinophenyl | 0 | Me | C(O) | 0 | H | 2-methylphenyl | OH | |
| 225 | 4-amidinophenyl | 0 | Me | C(O) | 0 | H | 3-methylphenyl | OH | |
| 226 | 4-amidinophenyl | 0 | Me | C(O) | 0 | H | 4-methylphenyl | OH | |
| 227 | 4-amidinophenyl | 0 | Me | C(O) | 0 | H | 2-methoxyphenyl | OH | |
| 228 | 4-amidinophenyl | 0 | Me | C(O) | 0 | H | 3-methoxyphenyl | OH | |
| 229 | 4-amidinophenyl | 0 | Me | C(O) | 0 | H | 4-methoxyphenyl | OH | |
| 230 | 4-amidinophenyl | 0 | Me | C(O) | 0 | H | 2-bromophenyl | OH | |
| 231 | 4-amidinophenyl | 0 | Me | C(O) | 0 | H | $CH_3NHC(O)$ | OH | |
| 232 | 4-amidinophenyl | 0 | Me | C(O) | 0 | H | $CH_3CH_2NHC(O)$ | OH | |
| 233 | 4-amidinophenyl | 0 | Me | C(O) | 0 | H | cyclopropyl-NHC(O) | OH | |
| 234 | 4-amidinophenyl | 0 | Me | C(O) | 0 | H | $CH_3OCH_2CH_2NHC(O)$ | OH | |
| 235 | 4-amidinophenyl | 0 | Me | C(O) | 0 | H | $Me_2N(CH_2)_3NHC(O)$ | OH | |
| 236 | 4-amidinophenyl | 0 | Me | C(O) | 0 | H | PhNHC(O) | OH | |
| 237 | 4-amidinophenyl | 0 | Me | C(O) | 0 | H | 2-MeOPhNH(CO) | OH | |
| 238 | 4-amidinophenyl | 0 | Me | C(O) | 0 | H | $Me_2NHC(O)$ | OH | |
| 239 | 4-amidinophenyl | 1 | Me | C(O) | 0 | H | H | OH | |
| 240 | 4-amidinophenyl | 1 | Me | C(O) | 0 | H | H | OMe | |
| 241 | 4-amidinophenyl | 1 | Me | C(O) | 0 | H | Me | OH | |
| 242 | 4-amidinophenyl | 1 | Me | C(O) | 0 | H | Et | OH | |
| 243 | 4-amidinophenyl | 1 | Me | C(O) | 0 | H | Propyl | OH | |
| 244 | 4-amidinophenyl | 1 | Me | C(O) | 0 | H | butyl | OH | |
| 245 | 4-amidinophenyl | 1 | Me | C(O) | 0 | H | hexyl | OH | |
| 246 | 4-amidinophenyl | 1 | Me | C(O) | 0 | H | cyclopropyl | OH | |
| 247 | 4-amidinophenyl | 1 | Me | C(O) | 0 | H | cyclohexyl | OH | |
| 248 | 4-amidinophenyl | 1 | Me | C(O) | 0 | H | acetynyl | OH | |
| 249 | 4-amidinophenyl | 1 | Me | C(O) | 0 | H | methylacetynyl | OH | |
| 250 | 4-amidinophenyl | 1 | Me | C(O) | 0 | H | cyclopropylacetynyl | OH | |
| 251 | 4-amidinophenyl | 1 | Me | C(O) | 0 | H | ethylacetynyl | OH | |
| 252 | 4-amidinophenyl | 1 | Me | C(O) | 0 | H | butylacetynyl | OH | |
| 253 | 4-amidinophenyl | 1 | Me | C(O) | 0 | H | vinyl | OH | |
| 254 | 4-amidinophenyl | 1 | Me | C(O) | 0 | H | phenethyl | OH | |
| 255 | 4-amidinophenyl | 1 | Me | C(O) | 0 | H | phenylmethyl | OH | |
| 256 | 4-amidinophenyl | 1 | Me | C(O) | 0 | H | 3-pyridinyl | OH | |
| 257 | 4-amidinophenyl | 1 | Me | C(O) | 0 | H | 2-pyridinyl | OH | |
| 258 | 4-amidinophenyl | 1 | Me | C(O) | 0 | H | 4-pyridinyl | OH | |
| 259 | 4-amidinophenyl | 1 | Me | C(O) | 0 | H | phenyl | OH | |
| 260 | 4-amidinophenyl | 1 | Me | C(O) | 0 | H | 2-fluorophenyl | OH | |
| 261 | 4-amidinophenyl | 1 | Me | C(O) | 0 | H | 3-fluorophenyl | OH | |
| 262 | 4-amidinophenyl | 1 | Me | C(O) | 0 | H | 4-fluorophenyl | OH | |
| 263 | 4-amidinophenyl | 1 | Me | C(O) | 0 | H | 2-methylphenyl | OH | |
| 264 | 4-amidinophenyl | 1 | Me | C(O) | 0 | H | 3-methylphenyl | OH | |
| 265 | 4-amidinophenyl | 1 | Me | C(O) | 0 | H | 4-methylphenyl | OH | |
| 266 | 4-amidinophenyl | 1 | Me | C(O) | 0 | H | 2-methoxyphenyl | OH | |
| 267 | 4-amidinophenyl | 1 | Me | C(O) | 0 | H | 3-methoxyphenyl | OH | |
| 268 | 4-amidinophenyl | 1 | Me | C(O) | 0 | H | 4-methoxyphenyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 269 | 4-amidinophenyl | 1 | Me | C(O) | 0 | H | 2-bromophenyl | OH | |
| 270 | 4-amidinophenyl | 1 | Me | C(O) | 0 | H | CH₃NHC(O) | OH | |
| 271 | 4-amidinophenyl | 1 | Me | C(O) | 0 | H | CH₃CH₂NHC(O) | OH | |
| 272 | 4-amidinophenyl | 1 | Me | C(O) | 0 | H | cyclopropyl-NHC(O) | OH | |
| 273 | 4-amidinophenyl | 1 | Me | C(O) | 0 | H | CH₃OCH₂CH₂NHC(O) | OH | |
| 274 | 4-amidinophenyl | 1 | Me | C(O) | 0 | H | Me₂N(CH₂)₃NHC(O) | OH | |
| 275 | 4-amidinophenyl | 1 | Me | C(O) | 0 | H | PhNHC(O) | OH | |
| 276 | 4-amidinophenyl | 1 | Me | C(O) | 0 | H | 2-MeOPhNH(CO) | OH | |
| 277 | 4-amidinophenyl | 1 | Me | C(O) | 0 | H | Me₂NHC(O) | OH | |
| 278 | 4-amidinophenyl | 0 | Me | C(O) | 2 | H | H | OH | |
| 279 | 4-amidinophenyl | 0 | Me | C(O) | 2 | H | H | OMe | |
| 280 | 4-amidinophenyl | 0 | Me | C(O) | 2 | H | Me | OH | |
| 281 | 4-amidinophenyl | 0 | Me | C(O) | 2 | H | Et | OH | |
| 282 | 4-amidinophenyl | 0 | Me | C(O) | 2 | H | Propyl | OH | |
| 283 | 4-amidinophenyl | 0 | Me | C(O) | 2 | H | butyl | OH | |
| 284 | 4-amidinophenyl | 0 | Me | C(O) | 2 | H | hexyl | OH | |
| 285 | 4-amidinophenyl | 0 | Me | C(O) | 2 | H | cyclopropyl | OH | |
| 286 | 4-amidinophenyl | 0 | Me | C(O) | 2 | H | cyclohexyl | OH | |
| 287 | 4-amidinophenyl | 0 | Me | C(O) | 2 | H | acetynyl | OH | |
| 288 | 4-amidinophenyl | 0 | Me | C(O) | 2 | H | methylacetynyl | OH | |
| 289 | 4-amidinophenyl | 0 | Me | C(O) | 2 | H | cyclopropylacetynyl | OH | |
| 290 | 4-amidinophenyl | 0 | Me | C(O) | 2 | H | ethylacetynyl | OH | |
| 291 | 4-amidinophenyl | 0 | Me | C(O) | 2 | H | butylacetynyl | OH | |
| 292 | 4-amidinophenyl | 0 | Me | C(O) | 2 | H | vinyl | OH | |
| 293 | 4-amidinophenyl | 0 | Me | C(O) | 2 | H | phenethyl | OH | |
| 294 | 4-amidinophenyl | 0 | Me | C(O) | 2 | H | phenylmethyl | OH | |
| 295 | 4-amidinophenyl | 0 | Me | C(O) | 2 | H | 3-pyridinyl | oH | |
| 296 | 4-amidinophenyl | 0 | Me | C(O) | 2 | H | 2-pyridinyl | OH | |
| 297 | 4-amidinophenyl | 0 | Me | C(O) | 2 | H | 4-pyridinyl | OH | |
| 298 | 4-amidinophenyl | 0 | Me | C(O) | 2 | H | phenyl | OH | |
| 299 | 4-amidinophenyl | 0 | Me | C(O) | 2 | H | 2-fluorophenyl | OH | |
| 300 | 4-amidinophenyl | 0 | Me | C(O) | 2 | H | 3-fluorophenyl | OH | |
| 301 | 4-amidinophenyl | 0 | Me | C(O) | 2 | H | 4-fluorophenyl | OH | |
| 302 | 4-amidinophenyl | 0 | Me | C(O) | 2 | H | 2-methylphenyl | OH | |
| 303 | 4-amidinophenyl | 0 | Me | C(O) | 2 | H | 3-methylphenyl | OH | |
| 304 | 4-amidinophenyl | 0 | Me | C(O) | 2 | H | 4-methylphenyl | OH | |
| 305 | 4-amidinophenyl | 0 | Me | C(O) | 2 | H | 2-methoxyphenyl | OH | |
| 306 | 4-amidinophenyl | 0 | Me | C(O) | 2 | H | 3-methoxyphenyl | OH | |
| 307 | 4-amidinophenyl | 0 | Me | C(O) | 2 | H | 4-methoxyphenyl | OH | |
| 308 | 4-amidinophenyl | 0 | Me | C(O) | 2 | H | 2-bromophenyl | OH | |
| 309 | 4-amidinophenyl | 0 | Me | C(O) | 2 | H | CH₃NHC(O) | OH | |
| 310 | 4-amidinophenyl | 0 | Me | C(O) | 2 | H | CH₃CH₂NHC(O) | OH | |
| 311 | 4-amidinophenyl | 0 | Me | C(O) | 2 | H | cyclopropyl-NHC(O) | OH | |
| 312 | 4-amidinophenyl | 0 | Me | C(O) | 2 | H | CH₃OCH₂CH₂NHC(O) | OH | |
| 313 | 4-amidinophenyl | 0 | Me | C(O) | 2 | H | Me₂N(CH₂)₃NHC(O) | OH | |
| 314 | 4-amidinophenyl | 0 | Me | C(O) | 2 | H | PhNHC(O) | OH | |
| 315 | 4-amidinophenyl | 0 | Me | C(O) | 2 | H | 2-MeOPhNH(CO) | OH | |
| 316 | 4-amidinophenyl | 0 | Me | C(O) | 2 | H | Me₂NHC(O) | OH | |
| 317 | 4-amidinophenyl | 0 | Me | C(O) | 1 | H | indole-3-ethyl | OH | 506 |
| 318 | 4-amidinophenyl | 0 | benzyl | C(O) | 1 | H | H | OH | 439 |
| 319 | 4-amidinophenyl 4-R, 6-S | 0 | benzyl | C(O) | 1 | H | H | OH | 439 |
| 320 | 4-amidinophenyl | 0 | benzyl | C(O) | 1 | H | Me | OH | 453 |
| 321 | 4-amidinophenyl | 0 | benzyl | C(O) | 1 | H | Et | OH | |
| 322 | 4-amidinophenyl | 0 | benzyl | C(O) | 1 | H | Propyl | OH | |
| 323 | 4-amidinophenyl | 0 | benzyl | C(O) | 1 | H | butyl | OH | |
| 324 | 4-amidinophenyl | 0 | benzyl | C(O) | 1 | H | hexyl | OH | |
| 325 | 4-amidinophenyl | 0 | benzyl | C(O) | 1 | H | cyclopropyl | OH | |
| 326 | 4-amidinophenyl | 0 | benzyl | C(O) | 1 | H | cyclohexyl | OH | |
| 327 | 4-amidinophenyl | 0 | benzyl | C(O) | 1 | H | acetynyl | OH | |
| 328 | 4-amidinophenyl | 0 | benzyl | C(O) | 1 | H | methylacetynyl | OH | |
| 329 | 4-amidinophenyl | 0 | benzyl | C(O) | 1 | H | cyclopropylacetynyl | OH | |
| 330 | 4-amidinophenyl | 0 | benzyl | C(O) | 1 | H | ethylacetynyl | OH | |
| 331 | 4-amidinophenyl | 0 | benzyl | C(O) | 1 | H | butylacetynyl | OH | |
| 332 | 4-amidinophenyl | 0 | benzyl | C(O) | 1 | H | vinyl | OH | |
| 333 | 4-amidinophenyl | 0 | benzyl | C(O) | 1 | H | phenethyl | OH | |
| 334 | 4-amidinophenyl | 0 | benzyl | C(O) | 1 | H | phenylmethyl | OH | |
| 335 | 4-amidinophenyl | 0 | benzyl | C(O) | 1 | H | 3-pyridinyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 336 | 4-amidinophenyl | 0 | benzyl | C(O) | 1 | H | 2-pyridinyl | OH | |
| 337 | 4-amidinophenyl | 0 | benzyl | C(O) | 1 | H | 4-pyridinyl | OH | |
| 338 | 4-amidinophenyl | 0 | benzyl | C(O) | 1 | H | phenyl | OH | |
| 339 | 4-amidinophenyl | 0 | benzyl | C(O) | 1 | H | 2-fluorophenyl | OH | |
| 340 | 4-amidinophenyl | 0 | benzyl | C(O) | 1 | H | 3-fluorophenyl | OH | 471 |
| 341 | 4-amidinophenyl | 0 | benzyl | C(O) | 1 | H | 4-fluorophenyl | OH | |
| 342 | 4-amidinophenyl | 0 | benzyl | C(O) | 1 | H | 2-methylphenyl | OH | |
| 343 | 4-amidinophenyl | 0 | benzyl | C(O) | 1 | H | 3-methylphenyl | OH | |
| 344 | 4-amidinophenyl | 0 | benzyl | C(O) | 1 | H | 4-methylphenyl | OH | |
| 345 | 4-amidinophenyl | 0 | benzyl | C(O) | 1 | H | 2-methoxyphenyl | OH | |
| 346 | 4-amidinophenyl | 0 | benzyl | C(O) | 1 | H | 3-methoxyphenyl | OH | |
| 347 | 4-amidinophenyl | 0 | benzyl | C(O) | 1 | H | 4-methoxyphenyl | OH | |
| 348 | 4-amidinophenyl | 0 | benzyl | C(O) | 1 | H | 2-bromophenyl | OH | |
| 349 | 4-amidinophenyl | 0 | benzyl | C(O) | 1 | H | CH₃NHC(O) | OH | |
| 350 | 4-amidinophenyl | 0 | benzyl | C(O) | 1 | H | CH₃CH₂NHC(O) | OH | |
| 351 | 4-amidinophenyl | 0 | benzyl | C(O) | 1 | H | cyclopropyl-NHC(O) | OH | |
| 352 | 4-amidinophenyl | 0 | benzyl | C(O) | 1 | H | CH₃OCH₂CH₂NHC(O) | OH | |
| 353 | 4-amidinophenyl | 0 | benzyl | C(O) | 1 | H | Me₂N(CH₂)₃NHC(O) | OH | |
| 354 | 4-amidinophenyl | 0 | benzyl | C(O) | 1 | H | PhNHC(O) | OH | |
| 355 | 4-amidinophenyl | 0 | benzyl | C(O) | 1 | H | 2-MeOPhNH(CO) | OH | |
| 356 | 4-amidinophenyl | 0 | benzyl | C(O) | 1 | H | Me₂NHC(O) | OH | |
| 357 | 4-(N-methylamidino)phenyl | 0 | Me | C(O) | 1 | H | H | OH | |
| 358 | 4-(N-methylamidino)phenyl | 0 | Me | C(O) | 1 | H | H | OMe | |
| 359 | 4-(N-methylamidino)phenyl | 0 | Me | C(O) | 1 | H | Me | OH | |
| 360 | 4-(N-methylamidino)phenyl | 0 | Me | C(O) | 1 | H | Et | OH | |
| 361 | 4-(N-methylamidino)phenyl | 0 | Me | C(O) | 1 | H | Propyl | OH | |
| 362 | 4-(N-methylamidino)phenyl | 0 | Me | C(O) | 1 | H | butyl | OH | |
| 363 | 4-(N-methylamidino)phenyl | 0 | Me | C(O) | 1 | H | hexyl | OH | |
| 364 | 4-(N-methylamidino)phenyl | 0 | Me | C(O) | 1 | H | cyclopropyl | OH | |
| 365 | 4-(N-methylamidino)phenyl | 0 | Me | C(O) | 1 | H | cyclohexyl | OH | |
| 366 | 4-(N-methylamidino)phenyl | 0 | Me | C(O) | 1 | H | acetynyl | OH | |
| 367 | 4-(N-methylamidino)phenyl | 0 | Me | C(O) | 1 | H | methylacetynyl | OH | |
| 368 | 4-(N-methylamidino)phenyl | 0 | Me | C(O) | 1 | H | cyclopropylacetynyl | OH | |
| 369 | 4-(N-methylamidino)phenyl | 0 | Me | C(O) | 1 | H | ethylacetynyl | OH | |
| 370 | 4-(N-methylamidino)phenyl | 0 | Me | C(O) | 1 | H | butylacetynyl | OH | |
| 371 | 4-(N-methylamidino)phenyl | 0 | Me | C(O) | 1 | H | vinyl | OH | |
| 372 | 4-(N-methylamidino)phenyl | 0 | Me | C(O) | 1 | H | phenethyl | OH | |
| 373 | 4-(N-methylamidino)phenyl | 0 | Me | C(O) | 1 | H | phenylmethyl | OH | |
| 374 | 4-(N-methylamidino)phenyl | 0 | Me | C(O) | 1 | H | 3-pyridinyl | OH | |
| 375 | 4-(N-methylamidino)phenyl | 0 | Me | C(O) | 1 | H | 2-pyridinyl | OH | |
| 376 | 4-(N-methylamidino)phenyl | 0 | Me | C(O) | 1 | H | 4-pyridinyl | OH | |
| 377 | 4-(N-methylamidino)phenyl | 0 | Me | C(O) | 1 | H | phenyl | OH | |
| 378 | 4-(N-methylamidino)phenyl | 0 | Me | C(O) | 1 | H | 2-fluorophenyl | OH | |
| 379 | 4-(N-methylamidino)phenyl | 0 | Me | C(O) | 1 | H | 3-fluorophenyl | OH | |
| 380 | 4-(N-methylamidino)phenyl | 0 | Me | C(O) | 1 | H | 4-fluorophenyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 381 | 4-(N-methylamidino)phenyl | 0 | Me | C(O) | 1 | H | 2-methylphenyl | OH | |
| 382 | 4-(N-methylamidino)phenyl | 0 | Me | C(O) | 1 | H | 3-methylphenyl | OH | |
| 383 | 4-(N-methylamidino)phenyl | 0 | Me | C(O) | 1 | H | 4-methylphenyl | OH | |
| 384 | 4-(N-methylamidino)phenyl | 0 | Me | C(O) | 1 | H | 2-methoxyphenyl | OH | |
| 385 | 4-(N-methylamidino)phenyl | 0 | Me | C(O) | 1 | H | 3-methoxyphenyl | OH | |
| 386 | 4-(N-methylamidino)phenyl | 0 | Me | C(O) | 1 | H | 4-methoxyphenyl | OH | |
| 387 | 4-(N-methylamidino)phenyl | 0 | Me | C(O) | 1 | H | 2-bromophenyl | OH | |
| 388 | 4-(N-methylamidino)phenyl | 0 | Me | C(O) | 1 | H | $CH_3NHC(O)$ | OH | |
| 389 | 4-(N-methylamidino)phenyl | 0 | Me | C(O) | 1 | H | $CH_3CH_2NHC(O)$ | OH | |
| 390 | 4-(N-methylamidino)phenyl | 0 | Me | C(O) | 1 | H | cyclopropyl-NHC(O) | OH | |
| 391 | 4-(N-methylamidino)phenyl | 0 | Me | C(O) | 1 | H | $CH_3OCH_2CH_2NHC(O)$ | OH | |
| 392 | 4-(N-methylamidino)phenyl | 0 | Me | C(O) | 1 | H | $Me_2N(CH_2)_3NHC(O)$ | OH | |
| 393 | 4-(N-methylamidino)phenyl | 0 | Me | C(O) | 1 | H | PhNHC(O) | OH | |
| 394 | 4-(N-methylamidino)phenyl | 0 | Me | C(O) | 1 | H | 2-MeOPhNH(CO) | OH | |
| 395 | 4-(N-methylamidino)phenyl | 0 | Me | C(O) | 1 | H | $Me_2NHC(O)$ | OH | |
| 396 | 4-(N-butylamidino)phenyl | 0 | Me | C(O) | 1 | H | H | OH | |
| 397 | 4-(N-butylamidino)phenyl | 0 | Me | C(O) | 1 | H | H | OMe | |
| 398 | 4-(N-butylamidino)phenyl | 0 | Me | C(O) | 1 | H | Me | OH | |
| 399 | 4-(N-butylamidino)phenyl | 0 | Me | C(O) | 1 | H | Et | OH | |
| 400 | 4-(N-butylamidino)phenyl | 0 | Me | C(O) | 1 | H | Propyl | OH | |
| 401 | 4-(N-butylamidino)phenyl | 0 | Me | C(O) | 1 | H | butyl | OH | |
| 402 | 4-(N-butylamidino)phenyl | 0 | Me | C(O) | 1 | H | hexyl | OH | |
| 403 | 4-(N-hutylamidino)phenyl | 0 | Me | C(O) | 1 | H | cyclopropyl | OH | |
| 404 | 4-(N-butylamidino)phenyl | 0 | Me | C(O) | 1 | H | cyclohexyl | OH | |
| 405 | 4-(N-butylamidino)phenyl | 0 | Me | C(O) | 1 | H | acetynyl | OH | |
| 406 | 4-(N-butylamidino)phenyl | 0 | Me | C(O) | 1 | H | methylacetynyl | OH | |
| 407 | 4-(N-butylamidino)phenyl | 0 | Me | C(O) | 1 | H | cyclopropylacetynyl | OH | |
| 408 | 4-(N-butylamidino)phenyl | 0 | Me | C(O) | 1 | H | ethylacetynyl | OH | |
| 409 | 4-(N-butylamidino)phenyl | 0 | Me | C(O) | 1 | H | butylacetynyl | OH | |
| 410 | 4-(N-butylamidino)phenyl | 0 | Me | C(O) | 1 | H | vinyl | OH | |
| 411 | 4-(N-butylamidino)phenyl | 0 | Me | C(O) | 1 | H | phenethyl | OH | 523 |
| 412 | 4-(N-butylamidino)phenyl | 0 | Me | C(O) | 1 | H | phenylmethyl | OH | |
| 413 | 4-(N-butylamidino)phenyl | 0 | Me | C(O) | 1 | H | 3-pyridinyl | OH | |
| 414 | 4-(N-butylamidino) | 0 | Me | C(O) | 1 | H | 2-pyridinyl | OH | |

TABLE 1-continued

Structure: R¹—A—(CH₂)ₘ—[ring with N(R³)—X—O and position 6]—(CH₂)ₙ—C(O)—N(R⁵)—CH(R⁸)—CH₂—C(O)Y (with 3' stereocenter)

| Ex No. | R¹—A | m | R³ | X | n | R⁵ | R⁸ | Y | MS [(M + 1)⁺] |
|---|---|---|---|---|---|---|---|---|---|
| 415 | 4-(N-butylamidino)phenyl | 0 | Me | C(O) | 1 | H | 4-pyridinyl | OH | |
| 416 | 4-(N-butylamidino)phenyl | 0 | Me | C(O) | 1 | H | phenyl | OH | |
| 417 | 4-(N-butylamidino)phenyl | 0 | Me | C(O) | 1 | H | 2-fluorophenyl | OH | |
| 418 | 4-(N-butylamidino)phenyl | 0 | Me | C(O) | 1 | H | 3-fluorophenyl | OH | |
| 419 | 4-(N-butylamidino)phenyl | 0 | Me | C(O) | 1 | H | 4-fluorophenyl | OH | |
| 420 | 4-(N-butylamidino)phenyl | 0 | Me | C(O) | 1 | H | 2-methylphenyl | OH | |
| 421 | 4-(N-butylamidino)phenyl | 0 | Me | C(O) | 1 | H | 3-methylphenyl | OH | |
| 422 | 4-(N-butylamidino)phenyl | 0 | Me | C(O) | 1 | H | 4-methylphenyl | OH | |
| 423 | 4-(N-butylamidino)phenyl | 0 | Me | C(O) | 1 | H | 2-methoxyphenyl | OH | |
| 424 | 4-(N-butylamidino)phenyl | 0 | Me | C(O) | 1 | H | 3-methoxyphenyl | OH | |
| 425 | 4-(N-butylamidino)phenyl | 0 | Me | C(O) | 1 | H | 4-methoxyphenyl | OH | |
| 426 | 4-(N-butylamidino)phenyl | 0 | Me | C(O) | 1 | H | 2-bromophenyl | OH | |
| 427 | 4-(N-butylamidino)phenyl | 0 | Me | C(O) | 1 | H | CH₃NHC(O) | OH | |
| 428 | 4-(N-butylamidino)phenyl | 0 | Me | C(O) | 1 | H | CH₃CH₂NHC(O) | OH | |
| 429 | 4-(N-butylamidino)phenyl | 0 | Me | C(O) | 1 | H | cyclopropyl-NHC(O) | OH | |
| 430 | 4-(N-butylamidino)phenyl | 0 | Me | C(O) | 1 | H | CH₃OCH₂CH₂NHC(O) | OH | |
| 431 | 4-(N-butylamidino)phenyl | 0 | Me | C(O) | 1 | H | Me₂N(CH₂)₃NHC(O) | OH | |
| 432 | 4-(N-butylamidino)phenyl | 0 | Me | C(O) | 1 | H | PhNHC(O) | OH | |
| 433 | 4-(N-butylamidino)phenyl | 0 | Me | C(O) | 1 | H | 2-MeOPhNH(CO) | OH | |
| 434 | 4-(N-butylamidino)phenyl | 0 | Me | C(O) | 1 | H | Me₂NHC(O) | OH | |
| 435 | 4-(N-butylamidino)phenyl | 0 | benzyl | C(O) | 1 | H | H | OH | |
| 436 | 4-(N-butylamidino)phenyl | 0 | benzyl | C(O) | 1 | H | H | OMe | |
| 437 | 4-(N-butylamidino)phenyl | 0 | benzyl | C(O) | 1 | H | Me | OH | |
| 438 | 4-(N-butylamidino)phenyl | 0 | benzyl | C(O) | 1 | H | Et | OH | |
| 439 | 4-(N-butylamidino)phenyl | 0 | benzyl | C(O) | 1 | H | Propyl | OH | |
| 440 | 4-(N-butylamidino)phenyl | 0 | benzyl | C(O) | 1 | H | butyl | OH | |
| 441 | 4-(N-butylamidino)phenyl | 0 | benzyl | C(O) | 1 | H | hexyl | OH | |
| 442 | 4-(N-butylamidino)phenyl | 0 | benzyl | C(O) | 1 | H | cyclopropyl | OH | |
| 443 | 4-(N-butylamidino)phenyl | 0 | benzyl | C(O) | 1 | H | cyclohexyl | OH | |
| 444 | 4-(N-butylamidino)phenyl | 0 | benzyl | C(O) | 1 | H | acetynyl | OH | |
| 445 | 4-(N-butylamidino)phenyl | 0 | benzyl | C(O) | 1 | H | methylacetynyl | OH | |
| 446 | 4-(N-butylamidino)phenyl | 0 | benzyl | C(O) | 1 | H | cyclopropylacetynyl | OH | |
| 447 | 4-(N-butylamidino)phenyl | 0 | benzyl | C(O) | 1 | H | ethylacetynyl | OH | |
| 448 | 4-(N-butylamidino)phenyl | 0 | benzyl | C(O) | 1 | H | butylacetynyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 449 | 4-(N-butylamidino)phenyl | 0 | benzyl | C(O) | 1 | H | vinyl | OH | |
| 450 | 4-(N-butylamidino)phenyl | 0 | benzyl | C(O) | 1 | H | phenethyl | OH | 523 |
| 451 | 4-(N-butylamidino)phenyl | 0 | benzyl | C(O) | 1 | H | phenylmethyl | OH | |
| 452 | 4-(N-butylamidino)phenyl | 0 | benzyl | C(O) | 1 | H | 3-pyridinyl | OH | |
| 453 | 4-(N-butylamidino)phenyl | 0 | benzyl | C(O) | 1 | H | 2-pyridinyl | OH | |
| 454 | 4-(N-butylamidino)phenyl | 0 | benzyl | C(O) | 1 | H | 4-pyridinyl | OH | |
| 455 | 4-(N-butylamidino)phenyl | 0 | benzyl | C(O) | 1 | H | phenyl | OH | |
| 456 | 4-(N-butylamidino)phenyl | 0 | benzyl | C(O) | 1 | H | 2-fluorophenyl | OH | |
| 457 | 4-(N-butylamidino)phenyl | 0 | benzyl | C(O) | 1 | H | 3-fluorophenyl | OH | |
| 458 | 4-(N-butylamidino)phenyl | 0 | benzyl | C(O) | 1 | H | 4-fluorophenyl | OH | |
| 459 | 4-(N-butylamidino)phenyl | 0 | benzyl | C(O) | 1 | H | 2-methylphenyl | OH | |
| 460 | 4-(N-butylamidino)phenyl | 0 | benzyl | C(O) | 1 | H | 3-methylphenyl | OH | |
| 461 | 4-(N-butylamidino)phenyl | 0 | benzyl | C(O) | 1 | H | 4-methylphenyl | OH | |
| 462 | 4-(N-butylamidino)phenyl | 0 | benzyl | C(O) | 1 | H | 2-methoxyphenyl | OH | |
| 463 | 4-(N-butylamidino)phenyl | 0 | benzyl | C(O) | 1 | H | 3-methoxyphenyl | OH | |
| 464 | 4-(N-butylamidino)phenyl | 0 | benzyl | C(O) | 1 | H | 4-methoxyphenyl | OH | |
| 465 | 4-(N-butylamidino)phenyl | 0 | benzyl | C(O) | 1 | H | 2-bromophenyl | OH | |
| 466 | 4-(N-butylamidino)phenyl | 0 | benzyl | C(O) | 1 | H | $CH_3NHC(O)$ | OH | |
| 467 | 4-(N-butylamidino)phenyl | 0 | benzyl | C(O) | 1 | H | $CH_3CH_2NHC(O)$ | OH | |
| 468 | 4-(N-butylamidino)phenyl | 0 | benzyl | C(O) | 1 | H | cyclopropyl-NHC(O) | OH | |
| 469 | 4-(N-butylamidino)phenyl | 0 | benzyl | C(O) | 1 | H | $CH_3OCH_2CH_2NHC(O)$ | OH | |
| 470 | 4-(N-butylamidino)phenyl | 0 | bnenzyl | C(O) | 1 | H | $Me_2N(CH_2)_3NHC(O)$ | OH | |
| 471 | 4-(N-butylamidino)phenyl | 0 | benzyl | C(O) | 1 | H | PhNHC(O) | OH | |
| 472 | 4-(N-butylamidino)phenyl | 0 | benzyl | C(O) | 1 | H | 2-MeOPhNH(CO) | OH | |
| 473 | 4-(N-butylamidino)phenyl | 0 | benzyl | C(O) | 1 | H | $Me_2NHC(O)$ | OH | |
| 474 | 4-piperidinyl | 2 | benzyl | C(O) | 1 | H | Me | OH | |
| 475 | 4-piperidinyl | 2 | benzyl | C(O) | 1 | H | Et | OH | |
| 476 | 4-piperidinyl | 2 | benzyl | C(O) | 1 | H | Propyl | OH | |
| 477 | 4-piperidinyl | 2 | benzyl | C(O) | 1 | H | butyl | OH | |
| 478 | 4-piperidinyl | 2 | benzyl | C(O) | 1 | H | hexyl | OH | |
| 479 | 4-piperidinyl | 2 | benzyl | C(O) | 1 | H | cyclopropyl | OH | |
| 480 | 4-piperidinyl | 2 | benzyl | C(O) | 1 | H | cyclohexyl | OH | |
| 481 | 4-piperidinyl | 2 | benzyl | C(O) | 1 | H | acetynyl | OH | |
| 482 | 4-piperidinyl | 2 | benzyl | C(O) | 1 | H | methylacetynyl | OH | |
| 483 | 4-piperidinyl | 2 | benzyl | C(O) | 1 | H | cyclopropylacetynyl | OH | |
| 484 | 4-piperidinyl | 2 | benzyl | C(O) | 1 | H | ethylacetynyl | OH | |
| 485 | 4-piperidinyl | 2 | benzyl | C(O) | 1 | H | butylacetynyl | OH | |
| 486 | 4-piperidinyl | 2 | benzyl | C(O) | 1 | H | vinyl | OH | |
| 487 | 4-piperidinyl | 2 | benzyl | C(O) | 1 | H | phenethyl | OH | |
| 488 | 4-piperidinyl | 2 | benzyl | C(O) | 1 | H | phenylmethyl | OH | |
| 489 | 4-piperidinyl | 2 | benzyl | C(O) | 1 | H | 3-pyridinyl | OH | |
| 490 | 4-piperidinyl | 2 | benzyl | C(O) | 1 | H | 2-pyridinyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 491 | 4-piperidinyl | 2 | benzyl | C(O) | 1 | H | 4-pyridinyl | OH | |
| 492 | 4-piperidinyl | 2 | benzyl | C(O) | 1 | H | phenyl | OH | |
| 493 | 4-piperidinyl | 2 | benzyl | C(O) | 1 | H | 2-fluorophenyl | OH | |
| 494 | 4-piperidinyl | 2 | benzyl | C(O) | 1 | H | 3-fluorophenyl | OH | |
| 495 | 4-piperidinyl | 2 | benzyl | C(O) | 1 | H | 4-fluorophenyl | OH | |
| 496 | 4-piperidinyl | 2 | benzyl | C(O) | 1 | H | 2-methylphenyl | OH | |
| 497 | 4-piperidinyl | 2 | benzyl | C(O) | 1 | H | 3-methylphenyl | OH | |
| 498 | 4-piperidinyl | 2 | benzyl | C(O) | 1 | H | 4-methylphenyl | OH | |
| 499 | 4-piperidinyl | 2 | benzyl | C(O) | 1 | H | 2-methoxyphenyl | OH | |
| 500 | 4-piperidinyl | 2 | benzyl | C(O) | 1 | H | 3-methoxyphenyl | OH | |
| 501 | 4-piperidinyl | 2 | benzyl | C(O) | 1 | H | 4-methoxyphenyl | OH | |
| 502 | 4-piperidinyl | 2 | benzyl | C(O) | 1 | H | 2-bromophenyl | OH | |
| 503 | 4-piperidinyl | 2 | benzyl | C(O) | 1 | H | $CH_3NHC(O)$ | OH | |
| 504 | 4-piperidinyl | 2 | benzyl | C(O) | 1 | H | $CH_3CH_2NHC(O)$ | OH | |
| 505 | 4-piperidinyl | 2 | benzyl | C(O) | 1 | H | cyclopropyl-NHC(O) | OH | |
| 506 | 4-piperidinyl | 2 | benzyl | C(O) | 1 | H | $CH_3OCH_2CH_2NHC(O)$ | OH | |
| 507 | 4-piperidinyl | 2 | benzyl | C(O) | 1 | H | $Me_2N(CH_2)_3NHC(O)$ | OH | |
| 508 | 4-piperidinyl | 2 | benzyl | C(O) | 1 | H | PhNHC(O) | OH | |
| 509 | 4-piperidinyl | 2 | benzyl | C(O) | 1 | H | 2-MeOPhNH(CO) | OH | |
| 510 | 4-piperidinyl | 2 | benzyl | C(O) | 1 | H | $Me_2NHC(O)$ | OH | |
| 511 | 4-amidinophenyl | 0 | Me | none | 1 | H | H | OH | 335 |
| 512 | 4-amidinophenyl 4-R, 6-S | 0 | Me | none | 1 | H | H | OH | 335 |
| 514 | 4-amidinophenyl | 0 | Me | none | 1 | H | Me | OH | 349 |
| 515 | 4-amidinophenyl | 0 | Me | none | 1 | H | Et | OH | |
| 516 | 4-amidinophenyl | 0 | Me | none | 1 | H | Propyl | OH | |
| 517 | 4-amidinophenyl | 0 | Me | none | 1 | H | butyl | OH | |
| 518 | 4-amidinophenyl | 0 | Me | none | 1 | H | hexyl | OH | |
| 519 | 4-amidinophenyl | 0 | Me | none | 1 | H | cyclopropyl | OH | |
| 520 | 4-amidinophenyl | 0 | Me | none | 1 | H | cyclohexyl | OH | |
| 521 | 4-amidinophenyl | 0 | Me | none | 1 | H | acetynyl | OH | |
| 522 | 4-amidinophenyl | 0 | Me | none | 1 | H | methylacetynyl | OH | |
| 523 | 4-amidinophenyl | 0 | Me | none | 1 | H | cyclopropylacetynyl | OH | |
| 524 | 4-amidinophenyl | 0 | Me | none | 1 | H | ethylacetynyl | OH | |
| 525 | 4-amidinophenyl | 0 | Me | none | 1 | H | butylacetynyl | OH | |
| 526 | 4-amidinophenyl | 0 | Me | none | 1 | H | vinyl | OH | |
| 527 | 4-amidinophenyl | 0 | Me | none | 1 | H | phenethyl | OH | |
| 528 | 4-amidinophenyl | 0 | Me | none | 1 | H | phenylmethyl | OH | |
| 529 | 4-amidinophenyl | 0 | Me | none | 1 | H | 3-pyridinyl | OH | |
| 530 | 4-amidinophenyl | 0 | Me | none | 1 | H | 2-pyridinyl | OH | |
| 531 | 4-amidinophenyl | 0 | Me | none | 1 | H | 4-pyridinyl | OH | |
| 532 | 4-amidinophenyl | 0 | Me | none | 1 | H | phenyl | OH | |
| 533 | 4-amidinophenyl | 0 | Me | none | 1 | H | 2-fluorophenyl | OH | |
| 534 | 4-amidinophenyl | 0 | Me | none | 1 | H | 3-fluorophenyl | OH | |
| 535 | 4-amidinophenyl | 0 | Me | none | 1 | H | 4-fluorophenyl | OH | |
| 536 | 4-amidinophenyl | 0 | Me | none | 1 | H | 2-methylphenyl | OH | |
| 537 | 4-amidinophenyl | 0 | Me | none | 1 | H | 3-methylphenyl | OH | |
| 538 | 4-amidinophenyl | 0 | Me | none | 1 | H | 4-methylphenyl | OH | |
| 539 | 4-amidinophenyl | 0 | Me | none | 1 | H | 2-methoxyphenyl | OH | |
| 540 | 4-amidinophenyl | 0 | Me | none | 1 | H | 3-methoxyphenyl | OH | |
| 541 | 4-amidinophenyl | 0 | Me | none | 1 | H | 4-methoxyphenyl | OH | |
| 542 | 4-amidinophenyl | 0 | Me | none | 1 | H | 2-bromophenyl | OH | |
| 543 | 4-amidinophenyl | 0 | Me | none | 1 | H | $CH_3NHC(O)$ | OH | |
| 544 | 4-amidinophenyl | 0 | Me | none | 1 | H | $CH_3CH_2NHC(O)$ | OH | |
| 545 | 4-amidinophenyl | 0 | Me | none | 1 | H | cyclopropyl-NHC(O) | OH | |
| 546 | 4-amidinophenyl | 0 | Me | none | 1 | H | $CH_3OCH_2CH_2NHC(O)$ | OH | |
| 547 | 4-amidinophenyl | 0 | Me | none | 1 | H | $Me_2N(CH_2)_3NHC(O)$ | OH | |
| 548 | 4-amidinophenyl | 0 | Me | none | 1 | H | PhNHC(O) | OH | |
| 549 | 4-amidinophenyl | 0 | Me | none | 1 | H | 2-MeOPhNH(CO) | OH | |
| 550 | 4-amidinophenyl | 0 | Me | none | 1 | H | $Me_2NC(O)$ | OH | |
| 551 | 4-amidinophenyl | 0 | Et | none | 1 | H | H | OH | |
| 552 | 4-amidinophenyl | 0 | Et | none | 1 | H | Me | OH | |
| 553 | 4-amidinophenyl | 0 | Et | none | 1 | H | Et | OH | |
| 554 | 4-amidinophenyl | 0 | Et | none | 1 | H | Propyl | OH | |
| 555 | 4-amidinophenyl | 0 | Et | none | 1 | H | butyl | OH | |
| 556 | 4-amidinophenyl | 0 | Et | none | 1 | H | hexyl | OH | |
| 557 | 4-amidinophenyl | 0 | Et | none | 1 | H | cyclopropyl | OH | |
| 558 | 4-amidinophenyl | 0 | Et | none | 1 | H | cyclohexyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 559 | 4-amidinophenyl | 0 | Et | none | 1 | H | acetynyl | OH | |
| 560 | 4-amidinophenyl | 0 | Et | none | 1 | H | methylacetynyl | OH | |
| 561 | 4-amidinophenyl | 0 | Et | none | 1 | H | cyclopropylacetynyl | OH | |
| 562 | 4-amidinophenyl | 0 | Et | none | 1 | H | ethylacetynyl | OH | |
| 563 | 4-amidinophenyl | 0 | Et | none | 1 | H | butylacetynyl | OH | |
| 564 | 4-amidinophenyl | 0 | Et | none | 1 | H | vinyl | OH | |
| 565 | 4-amidinophenyl | 0 | Et | none | 1 | H | phenethyl | OH | |
| 566 | 4-amidinophenyl | 0 | Et | none | 1 | H | phenylmethyl | OH | |
| 567 | 4-amidinophenyl | 0 | Et | none | 1 | H | 3-pyridinyl | OH | |
| 568 | 4-amidinophenyl | 0 | Et | none | 1 | H | 2-pyridinyl | OH | |
| 569 | 4-amidinophenyl | 0 | Et | none | 1 | H | 4-pyridinyl | OH | |
| 570 | 4-amidinophenyl | 0 | Et | none | 1 | H | phenyl | OH | |
| 571 | 4-amidinophenyl | 0 | Et | none | 1 | H | 2-fluorophenyl | OH | |
| 572 | 4-amidinophenyl | 0 | Et | none | 1 | H | 3-fluorophenyl | OH | |
| 573 | 4-amidinophenyl | 0 | Et | none | 1 | H | 4-fluorophenyl | OH | |
| 574 | 4-amidinophenyl | 0 | Et | none | 1 | H | 2-methylphenyl | OH | |
| 575 | 4-amidinophenyl | 0 | Et | none | 1 | H | 3-methylphenyl | OH | |
| 576 | 4-amidinophenyl | 0 | Et | none | 1 | H | 4-methylphenyl | OH | |
| 577 | 4-amidinophenyl | 0 | Et | none | 1 | H | 2-methoxyphenyl | OH | |
| 578 | 4-amidinophenyl | 0 | Et | none | 1 | H | 3-methoxyphenyl | OH | |
| 578 | 4-amidinophenyl | 0 | Et | none | 1 | H | 4-methoxyphenyl | OH | |
| 579 | 4-amidinophenyl | 0 | Et | none | 1 | H | 2-bromophenyl | OH | |
| 580 | 4-amidinophenyl | 0 | Et | none | 1 | H | $CH_3NHC(O)$ | OH | |
| 581 | 4-amidinophenyl | 0 | Et | none | 1 | H | $CH_3CH_2NHC(O)$ | OH | |
| 582 | 4-amidinophenyl | 0 | Et | none | 1 | H | cyclopropyl-NHC(O) | OH | |
| 583 | 4-amidinophenyl | 0 | Et | none | 1 | H | $CH_3OCH_2CH_2NHC(O)$ | OH | |
| 584 | 4-amidinophenyl | 0 | Et | none | 1 | H | $Me_2N(CH_2)_3NHC(O)$ | OH | |
| 585 | 4-amidinophenyl | 0 | Et | none | 1 | H | PhNHC(O) | OH | |
| 586 | 4-amidinophenyl | 0 | Et | none | 1 | H | 2-MeOPhNH(CO) | OH | |
| 587 | 4-amidinophenyl | 0 | Et | none | 1 | H | $Me_2NHC(O)$ | OH | |
| 588 | 4-amidinophenyl | 0 | H | none | 1 | H | Me | OH | |
| 589 | 4-amidinophenyl | 0 | H | none | 1 | H | Et | OH | |
| 590 | 4-amidinophenyl | 0 | H | none | 1 | H | Propyl | OH | |
| 591 | 4-amidinophenyl | 0 | H | none | 1 | H | butyl | OH | |
| 592 | 4-amidinophenyl | 0 | H | none | 1 | H | hexyl | OH | |
| 593 | 4-amidinophenyl | 0 | H | none | 1 | H | cyclopropyl | OH | |
| 594 | 4-amidinophenyl | 0 | H | none | 1 | H | cyclohexyl | OH | |
| 595 | 4-amidinophenyl | 0 | H | none | 1 | H | acetynyl | OH | |
| 596 | 4-amidinophenyl | 0 | H | none | 1 | H | methylacetynyl | OH | |
| 597 | 4-amidinophenyl | 0 | H | none | 1 | H | cyclopropylacetynyl | OH | |
| 598 | 4-amidinophenyl | 0 | H | none | 1 | H | ethylacetynyl | OH | |
| 599 | 4-amidinophenyl | 0 | H | none | 1 | H | butylacetynyl | OH | |
| 600 | 4-amidinophenyl | 0 | H | none | 1 | H | vinyl | OH | |
| 601 | 4-amidinophenyl | 0 | H | none | 1 | Me | Me | OH | |
| 602 | 4-amidinophenyl | 0 | H | none | 1 | Me | Et | OH | |
| 603 | 4-amidinophenyl | 0 | H | none | 1 | Me | Propyl | OH | |
| 604 | 4-amidinophenyl | 0 | H | none | 1 | Me | butyl | OH | |
| 605 | 4-amidinophenyl | 0 | H | none | 1 | Me | hexyl | OH | |
| 606 | 4-amidinophenyl | 0 | H | none | 1 | Me | cyclopropyl | OH | |
| 607 | 4-amidinophenyl | 0 | H | none | 1 | Me | cyclohexyl | OH | |
| 608 | 4-amidinophenyl | 0 | H | none | 1 | Me | acetynyl | OH | |
| 609 | 4-amidinophenyl | 0 | H | none | 1 | Me | methylacetynyl | OH | |
| 610 | 4-amidinophenyl | 0 | H | none | 1 | Me | cyclopropylacetynyl | OH | |
| 611 | 4-amidinophenyl | 0 | H | none | 1 | Me | ethylacetynyl | OH | |
| 612 | 4-amidinophenyl | 0 | H | none | 1 | Me | butylacetynyl | OH | |
| 613 | 4-amidinophenyl | 0 | H | none | 1 | Me | vinyl | OH | |
| 614 | 4-amidinophenyl | 0 | H | none | 1 | Me | phenethyl | OH | |
| 615 | 4-amidinophenyl | 0 | H | none | 1 | Me | phenylmethyl | OH | |
| 616 | 4-amidinophenyl | 0 | H | none | 1 | Me | 3-pyridinyl | OH | |
| 617 | 4-amidinophenyl | 0 | H | none | 1 | Me | 2-pyridinyl | OH | |
| 618 | 4-amidinophenyl | 0 | H | none | 1 | Me | 4-pyridinyl | OH | |
| 619 | 4-amidinophenyl | 0 | H | none | 1 | Me | phenyl | OH | |
| 620 | 4-amidinophenyl | 0 | H | none | 1 | Me | 2-fluorophenyl | OH | |
| 621 | 4-amidinophenyl | 0 | H | none | 1 | Me | 3-fluorophenyl | OH | |
| 622 | 4-amidinophenyl | 0 | H | none | 1 | Me | 4-fluorophenyl | OH | |
| 623 | 4-amidinophenyl | 0 | H | none | 1 | Me | 2-methylphenyl | OH | |
| 624 | 4-amidinophenyl | 0 | H | none | 1 | Me | 3-methylphenyl | OH | |
| 625 | 4-amidinophenyl | 0 | H | none | 1 | Me | 4-methylphenyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 626 | 4-amidinophenyl | 0 | H | none | 1 | Me | 2-methoxyphenyl | OH | |
| 627 | 4-amidinophenyl | 0 | c-propyl | none | 1 | H | Me | OH | |
| 628 | 4-amidinophenyl | 0 | c-propyl | none | 1 | H | Et | OH | |
| 629 | 4-amidinophenyl | 0 | c-propyl | none | 1 | H | Propyl | OH | |
| 630 | 4-amidinophenyl | 0 | c-propyl | none | 1 | H | butyl | OH | |
| 631 | 4-amidinophenyl | 0 | c-propyl | none | 1 | H | hexyl | OH | |
| 632 | 4-amidinophenyl | 0 | c-propyl | none | 1 | H | cyclopropyl | OH | |
| 633 | 4-amidinophenyl | 0 | c-propyl | none | 1 | H | cyclohexyl | OH | |
| 634 | 4-amidinophenyl | 0 | c-propyl | none | 1 | H | acetynyl | OH | |
| 635 | 4-amidinophenyl | 0 | c-propyl | none | 1 | H | methylacetynyl | OH | |
| 636 | 4-amidinophenyl | 0 | c-propyl | none | 1 | H | cyclopropylacetynyl | OH | |
| 637 | 4-amidinophenyl | 0 | c-propyl | none | 1 | H | ethylacetynyl | OH | |
| 638 | 4-amidinophenyl | 0 | c-propyl | none | 1 | H | butylacetynyl | OH | |
| 639 | 4-amidinophenyl | 0 | c-propyl | none | 1 | H | vinyl | OH | |
| 640 | 4-amidinophenyl | 0 | c-propyl | none | 1 | H | phenethyl | OH | |
| 641 | 4-amidinophenyl | 0 | c-propyl | none | 1 | H | phenylmethyl | OH | |
| 642 | 4-amidinophenyl | 0 | c-propyl | none | 1 | H | 3-pyridinyl | OH | |
| 643 | 4-amidinophenyl | 0 | c-propyl | none | 1 | H | 2-pyridinyl | OH | |
| 644 | 4-amidinophenyl | 0 | c-propyl | none | 1 | H | 4-pyridinyl | OH | |
| 645 | 4-amidinophenyl | 0 | c-propyl | none | 1 | H | phenyl | OH | |
| 646 | 4-amidinophenyl | 0 | c-propyl | none | 1 | H | 2-fluorophenyl | OH | |
| 647 | 4-amidinophenyl | 0 | c-propyl | none | 1 | H | 3-fluorophenyl | OH | |
| 648 | 4-amidinophenyl | 0 | c-propyl | none | 1 | H | 4-fluorophenyl | OH | |
| 649 | 4-amidinophenyl | 0 | c-propyl | none | 1 | H | 2-methylphenyl | OH | |
| 650 | 4-amidinophenyl | 0 | c-propyl | none | 1 | H | 3-methylphenyl | OH | |
| 651 | 4-amidinophenyl | 0 | c-propyl | none | 1 | H | 4-methylphenyl | OH | |
| 652 | 4-amidinophenyl | 0 | c-propyl | none | 1 | H | 2-methoxyphenyl | OH | |
| 653 | 4-amidinophenyl | 0 | c-propyl | none | 1 | H | 3-methoxyphenyl | OH | |
| 654 | 4-amidinophenyl | 0 | c-propyl | none | 1 | H | 4-methoxyphenyl | OH | |
| 655 | 4-amidinophenyl | 0 | Me | none | 0 | H | Me | OH | |
| 656 | 4-amidinophenyl | 0 | Me | none | 0 | H | Et | OH | |
| 657 | 4-amidinophenyl | 0 | Me | none | 0 | H | Propyl | OH | |
| 658 | 4-amidinophenyl | 0 | Me | none | 0 | H | butyl | OH | |
| 659 | 4-amidinophenyl | 0 | Me | none | 0 | H | hexyl | OH | |
| 660 | 4-amidinophenyl | 0 | Me | none | 0 | H | cyclopropyl | OH | |
| 661 | 4-amidinophenyl | 0 | Me | none | 0 | H | cyclohexyl | OH | |
| 662 | 4-amidinophenyl | 0 | Me | none | 0 | H | acetynyl | OH | |
| 663 | 4-amidinophenyl | 0 | Me | none | 0 | H | methylacetynyl | OH | |
| 664 | 4-amidinophenyl | 0 | Me | none | 0 | H | cyclopropylacetynyl | OH | |
| 665 | 4-amidinophenyl | 0 | Me | none | 0 | H | ethylacetynyl | OH | |
| 666 | 4-amidinophenyl | 0 | Me | none | 0 | H | butylacetynyl | OH | |
| 667 | 4-amidinophenyl | 0 | Me | none | 0 | H | vinyl | OH | |
| 668 | 4-amidinophenyl | 0 | Me | none | 0 | H | phenethyl | OH | |
| 669 | 4-amidinophenyl | 0 | Me | none | 0 | H | phenylmethyl | OH | |
| 670 | 4-amidinophenyl | 0 | Me | none | 0 | H | 3-pyridinyl | OH | |
| 671 | 4-amidinophenyl | 0 | Me | none | 0 | H | 2-pyridinyl | OH | |
| 672 | 4-amidinophenyl | 0 | Me | none | 0 | H | 4-pyridinyl | OH | |
| 673 | 4-amidinophenyl | 0 | Me | none | 0 | H | phenyl | OH | |
| 674 | 4-amidinophenyl | 0 | Me | none | 0 | H | 2-fluorophenyl | OH | |
| 675 | 4-amidinophenyl | 0 | Me | none | 0 | H | 3-fluorophenyl | OH | |
| 676 | 4-amidinophenyl | 0 | Me | none | 0 | H | 4-fluorophenyl | OH | |
| 677 | 4-amidinophenyl | 0 | Me | none | 0 | H | 2-methylphenyl | OH | |
| 678 | 4-amidinophenyl | 0 | Me | none | 0 | H | 3-methylphenyl | OH | |
| 679 | 4-amidinophenyl | 0 | Me | none | 0 | H | 4-methylphenyl | OH | |
| 680 | 4-amidinophenyl | 0 | Me | none | 0 | H | 2-methoxyphenyl | OH | |
| 681 | 4-amidinophenyl | 0 | Me | none | 0 | H | 3-methoxyphenyl | OH | |
| 682 | 4-amidinophenyl | 0 | Me | none | 0 | H | 4-methoxyphenyl | OH | |
| 683 | 4-amidinophenyl | 0 | Me | none | 0 | H | 2-bromophenyl | OH | |
| 684 | 4-amidinophenyl | 1 | Me | none | 0 | H | Me | OH | |
| 685 | 4-amidinophenyl | 1 | Me | none | 0 | H | Et | OH | |
| 686 | 4-amidinophenyl | 1 | Me | none | 0 | H | Propyl | OH | |
| 687 | 4-amidinophenyl | 1 | Me | none | 0 | H | butyl | OH | |
| 688 | 4-amidinophenyl | 1 | Me | none | 0 | H | hexyl | OH | |
| 689 | 4-amidinophenyl | 1 | Me | none | 0 | H | cyclopropyl | OH | |
| 690 | 4-amidinophenyl | 1 | Me | none | 0 | H | cyclohexyl | OH | |
| 691 | 4-amidinophenyl | 1 | Me | none | 0 | H | acetynyl | OH | |
| 692 | 4-amidinophenyl | 1 | Me | none | 0 | H | methylacetynyl | OH | |
| 693 | 4-amidinophenyl | 1 | Me | none | 0 | H | cyclopropylacetynyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 694 | 4-amidinophenyl | 1 | Me | none | 0 | H | ethylacetynyl | OH | |
| 695 | 4-amidinophenyl | 1 | Me | none | 0 | H | butylacetynyl | OH | |
| 696 | 4-amidinophenyl | 1 | Me | none | 0 | H | vinyl | OH | |
| 697 | 4-amidinophenyl | 1 | Me | none | 0 | H | phenethyl | OH | |
| 698 | 4-amidinophenyl | 1 | Me | none | 0 | H | phenylmethyl | OH | |
| 699 | 4-amidinophenyl | 1 | Me | none | 0 | H | 3-pyridinyl | OH | |
| 700 | 4-amidinophenyl | 1 | Me | none | 0 | H | 2-pyridinyl | OH | |
| 701 | 4-amidinophenyl | 1 | Me | none | 0 | H | 4-pyridinyl | OH | |
| 702 | 4-amidinophenyl | 1 | Me | none | 0 | H | phenyl | OH | |
| 703 | 4-amidinophenyl | 1 | Me | none | 0 | H | 2-fluorophenyl | OH | |
| 704 | 4-amidinophenyl | 0 | Me | none | 2 | H | Me | OH | |
| 705 | 4-amidinophenyl | 0 | Me | none | 2 | H | Et | OH | |
| 706 | 4-amidinophenyl | 0 | Me | none | 2 | H | Propyl | OH | |
| 707 | 4-amidinophenyl | 0 | Me | none | 2 | H | butyl | OH | |
| 708 | 4-amidinophenyl | 0 | Me | none | 2 | H | hexyl | OH | |
| 709 | 4-amidinophenyl | 0 | Me | none | 2 | H | cyclopropyl | OH | |
| 710 | 4-amidinophenyl | 0 | Me | none | 2 | H | cyclohexyl | OH | |
| 711 | 4-amidinophenyl | 0 | Me | none | 2 | H | acetynyl | OH | |
| 712 | 4-amidinophenyl | 0 | Me | none | 2 | H | methylacetynyl | OH | |
| 713 | 4-amidinophenyl | 0 | Me | none | 2 | H | cyclopropylacetynyl | OH | |
| 714 | 4-amidinophenyl | 0 | Me | none | 2 | H | ethylacetynyl | OH | |
| 715 | 4-amidinophenyl | 0 | Me | none | 2 | H | butylacetynyl | OH | |
| 716 | 4-amidinophenyl | 0 | Me | none | 2 | H | vinyl | OH | |
| 717 | 4-amidinophenyl | 0 | Me | none | 2 | H | phenethyl | OH | |
| 718 | 4-amidinophenyl | 0 | Me | none | 2 | H | phenylmethyl | OH | |
| 719 | 4-amidinophenyl | 0 | Me | none | 2 | H | 3-pyridinyl | OH | |
| 720 | 4-amidinophenyl | 0 | Me | none | 2 | H | 2-pyridinyl | OH | |
| 721 | 4-amidinophenyl | 0 | Me | none | 2 | H | 4-pyridinyl | OH | |
| 722 | 4-amidinophenyl | 0 | Me | none | 2 | H | phenyl | OH | |
| 723 | 4-amidinophenyl | 0 | Me | none | 2 | H | 2-fluorophenyl | OH | |
| 724 | 4-amidinophenyl | 0 | Me | none | 2 | H | 3-fluorophenyl | OH | |
| 725 | 4-amidinophenyl | 0 | benzyl | none | 1 | H | Et | OH | |
| 726 | 4-amidinophenyl | 0 | benzyl | none | 1 | H | Propyl | OH | |
| 727 | 4-amidinophenyl | 0 | benzyl | none | 1 | H | butyl | OH | |
| 728 | 4-amidinophenyl | 0 | benzyl | none | 1 | H | hexyl | OH | |
| 729 | 4-amidinophenyl | 0 | benzyl | none | 1 | H | cyclopropyl | OH | |
| 730 | 4-amidinophenyl | 0 | benzyl | none | 1 | H | cyclohexyl | OH | |
| 731 | 4-amidinophenyl | 0 | benzyl | none | 1 | H | acetynyl | OH | |
| 732 | 4-amidinophenyl | 0 | benzyl | none | 1 | H | methylacetynyl | OH | |
| 733 | 4-amidinophenyl | 0 | benzyl | none | 1 | H | cyclopropylacetynyl | OH | |
| 734 | 4-amidinophenyl | 0 | benzyl | none | 1 | H | ethylacetynyl | OH | |
| 735 | 4-amidinophenyl | 0 | benzyl | none | 1 | H | butylacetynyl | OH | |
| 736 | 4-amidinophenyl | 0 | benzyl | none | 1 | H | vinyl | OH | |
| 737 | 4-amidinophenyl | 0 | benzyl | none | 1 | H | phenethyl | OH | |
| 738 | 4-amidinophenyl | 0 | benzyl | none | 1 | H | phenylmethyl | OH | |
| 739 | 4-amidinophenyl | 0 | benzyl | none | 1 | H | 3-pyridinyl | OH | |
| 740 | 4-amidinophenyl | 0 | benzyl | none | 1 | H | 2-pyridinyl | OH | |
| 741 | 4-amidinophenyl | 0 | benzyl | none | 1 | H | 4-pyridinyl | OH | |
| 742 | 4-amidinophenyl | 0 | benzyl | none | 1 | H | phenyl | OH | |
| 743 | 4-amidinophenyl | 0 | benzyl | none | 1 | H | 2-fluorophenyl | OH | |
| 744 | 4-(N-methylamidino)phenyl | 0 | Me | none | 1 | H | Me | OH | |
| 745 | 4-(N-methylamidino)phenyl | 0 | Me | none | 1 | H | Et | OH | |
| 746 | 4-(N-methylamidino)phenyl | 0 | Me | none | 1 | H | Propyl | OH | |
| 747 | 4-(N-methylamidino)phenyl | 0 | Me | none | 1 | H | butyl | OH | |
| 748 | 4-(N-methylamidino)phenyl | 0 | Me | none | 1 | H | hexyl | OH | |
| 749 | 4-(N-methylamidino)phenyl | 0 | Me | none | 1 | H | cyclopropyl | OH | |
| 750 | 4-(N-methylamidino)phenyl | 0 | Me | none | 1 | H | cyclohexyl | OH | |
| 751 | 4-(N-methylamidino)phenyl | 0 | Me | none | 1 | H | acetynyl | OH | |
| 752 | 4-(N-methylamidino)phenyl | 0 | Me | none | 1 | H | methylacetynyl | OH | |

TABLE 1-continued

| Ex No. | R¹—A | m | R³ | X | n | R⁵ | R⁸ | Y | MS [(M + 1)⁺] |
|---|---|---|---|---|---|---|---|---|---|
| 753 | 4-(N-methylamidino)phenyl | 0 | Me | none | 1 | H | cyclopropylacetynyl | OH | |
| 754 | 4-(N-methylamidino)phenyl | 0 | Me | none | 1 | H | ethylacetynyl | OH | |
| 755 | 4-(N-methylamidino)phenyl | 0 | Me | none | 1 | H | butylacetynyl | OH | |
| 756 | 4-(N-butylamidino)phenyl | 0 | Me | none | 1 | H | Me | OH | |
| 757 | 4-(N-butylamidino)phenyl | 0 | Me | none | 1 | H | Et | OH | |
| 758 | 4-(N-butylamidino)phenyl | 0 | Me | none | 1 | H | Propyl | OH | |
| 759 | 4-(N-butylamidino)phenyl | 0 | Me | none | 1 | H | butyl | OH | |
| 760 | 4-(N-butylamidino)phenyl | 0 | Me | none | 1 | H | hexyl | OH | |
| 761 | 4-(N-butylamidino)phenyl | 0 | Me | none | 1 | H | cyclopropyl | OH | |
| 762 | 4-(N-butylamidino)phenyl | 0 | Me | none | 1 | H | cyclohexyl | OH | |
| 763 | 4-(N-butylamidino)phenyl | 0 | Me | none | 1 | H | acetynyl | OH | |
| 764 | 4-(N-butylamidino)phenyl | 0 | Me | none | 1 | H | methylacetynyl | OH | |
| 765 | 4-(N-butylamidino)phenyl | 0 | Me | none | 1 | H | cyclopropylacetynyl | OH | |
| 766 | 4-(N-butylamidino)phenyl | 0 | Me | none | 1 | H | ethylacetynyl | OH | |
| 767 | 4-(N-butylamidino)phenyl | 0 | Me | none | 1 | H | butylacetynyl | OH | |
| 768 | 4-(N-butylamidino)phenyl | 0 | Me | none | 1 | H | vinyl | OH | |

TABLE 2

| Ex No. | R¹—A | m | R³ | X | n | U | V | j | Y | MS [(M + 1)⁺] |
|---|---|---|---|---|---|---|---|---|---|---|
| 769 | 4-amidinophenyl | 0 | Me | C(O) | 1 | N | none | 1 | OH | |
| 770 | 4-amidinophenyl | 0 | Me | C(O) | 1 | N | none | 1 | OMe | |
| 771 | 4-amidinophenyl 4-R, 6-S | 0 | Me | C(O) | 1 | N | none | 1 | OH | |
| 772 | 4-amidinophenyl | 0 | Me | C(O) | 1 | N | none | 2 | OH | |
| 773 | 4-amidinophenyl | 0 | Me | C(O) | 1 | N | none | 3 | OH | |
| 774 | 4-amidinophenyl | 0 | Me | C(O) | 1 | CH | none | 1 | OH | 417 |
| 775 | 4-amidinophenyl | 0 | Me | C(O) | 1 | CH | none | 2 | OH | |
| 776 | 4-amidinophenyl | 0 | Me | C(O) | 1 | CH | none | 3 | OH | |
| 777 | 4-amidinophenyl | 0 | Me | C(O) | 1 | CH | O | 1 | OH | |
| 778 | 4-amidinophenyl | 0 | Me | C(O) | 1 | CH | O | 2 | OH | |
| 779 | 4-amidinophenyl | 0 | Me | C(O) | 1 | CH | O | 3 | OH | |
| 780 | 4-amidinophenyl | 0 | Me | C(O) | 1 | N | O | 1 | OH | |
| 781 | 4-amidinophenyl | 0 | Me | C(O) | 1 | N | O | 2 | OH | |
| 782 | 4-amidinophenyl | 0 | Me | C(O) | 1 | N | NH | 1 | OH | |
| 783 | 4-amidinophenyl | 0 | Me | C(O) | 0 | N | none | 1 | OH | |
| 784 | 4-amidinophenyl | 0 | Me | C(O) | 0 | N | none | 1 | OMe | |
| 785 | 4-amidinophenyl | 0 | Me | C(O) | 0 | N | none | 2 | OH | |

TABLE 2-continued

| Ex No. | R¹—A | m | R³ | X | n | U | V | j | Y | MS [(M + 1)⁺] |
|---|---|---|---|---|---|---|---|---|---|---|
| 786 | 4-amidinophenyl | 0 | Me | C(O) | 0 | N | none | 3 | OH | |
| 787 | 4-amidinophenyl | 0 | Me | C(O) | 0 | CH | none | 1 | OH | |
| 788 | 4-amidinophenyl | 0 | Me | C(O) | 0 | CH | none | 2 | OH | |
| 789 | 4-amidinophenyl | 0 | Me | C(O) | 0 | CH | none | 3 | OH | |
| 790 | 4-amidinophenyl | 0 | Me | C(O) | 0 | CH | O | 1 | OH | |
| 791 | 4-amidinophenyl | 0 | Me | C(O) | 0 | CH | O | 2 | OH | |
| 792 | 4-amidinophenyl | 0 | Me | C(O) | 0 | N | O | 1 | OH | |
| 793 | 4-amidinophenyl | 0 | Me | C(O) | 0 | N | O | 2 | OH | |
| 794 | 4-amidinophenyl | 0 | Me | C(O) | 0 | N | NH | 1 | OH | |
| 795 | 4-amidinophenyl | 1 | Me | C(O) | 0 | N | none | 1 | OH | |
| 796 | 4-amidinophenyl | 1 | Me | C(O) | 0 | N | none | 1 | OMe | |
| 797 | 4-amidinophenyl | 1 | Me | C(O) | 0 | N | none | 2 | OH | |
| 798 | 4-amidinophenyl | 1 | Me | C(O) | 0 | N | none | 3 | OH | |
| 799 | 4-amidinophenyl | 1 | Me | C(O) | 0 | CH | none | 1 | OH | |
| 800 | 4-amidinophenyl | 1 | Me | C(O) | 0 | CH | none | 2 | OH | |
| 801 | 4-amidinophenyl | 1 | Me | C(O) | 0 | CH | none | 3 | OH | |
| 802 | 4-amidinophenyl | 1 | Me | C(O) | 0 | CH | O | 1 | OH | |
| 803 | 4-amidinophenyl | 1 | Me | C(O) | 0 | CH | O | 2 | OH | |
| 804 | 4-amidinophenyl | 1 | Me | C(O) | 0 | CH | O | 3 | OH | |
| 805 | 4-amidinophenyl | 1 | Me | C(O) | 0 | N | O | 1 | OH | |
| 806 | 4-amidinophenyl | 1 | Me | C(O) | 0 | N | O | 2 | OH | |
| 807 | 4-amidinophenyl | 1 | Me | C(O) | 0 | N | NH | 1 | OH | |
| 808 | 4-amidinophenyl | 1 | Et | C(O) | 0 | N | none | 1 | OH | |
| 809 | 4-amidinophenyl | 1 | Et | C(O) | 0 | N | none | 1 | OMe | |
| 810 | 4-amidinophenyl | 1 | Et | C(O) | 0 | N | none | 2 | OH | |
| 811 | 4-amidinophenyl | 1 | Et | C(O) | 0 | N | none | 3 | OH | |
| 812 | 4-amidinophenyl | 1 | Et | C(O) | 0 | CH | none | 1 | OH | |
| 813 | 4-amidinophenyl | 1 | Et | C(O) | 0 | CH | none | 2 | OH | |
| 814 | 4-amidinophenyl | 1 | Et | C(O) | 0 | CH | none | 3 | OH | |
| 815 | 4-amidinophenyl | 1 | Et | C(O) | 0 | CH | O | 1 | OH | |
| 816 | 4-amidinophenyl | 1 | Et | C(O) | 0 | CH | O | 2 | OH | |
| 817 | 4-amidinophenyl | 1 | Et | C(O) | 0 | CH | O | 3 | OH | |
| 818 | 4-amidinophenyl | 1 | Et | C(O) | 0 | N | O | 1 | OH | |
| 819 | 4-amidinophenyl | 1 | Et | C(O) | 0 | N | O | 2 | OH | |
| 820 | 4-amidinophenyl | 1 | Et | C(O) | 0 | N | NH | 1 | OH | |
| 821 | 4-amidinophenyl | 1 | benzyl | C(O) | 0 | N | none | 1 | OH | |
| 822 | 4-amidinophenyl | 1 | benzyl | C(O) | 0 | N | none | 1 | OMe | |
| 823 | 4-amidinophenyl | 1 | benzyl | C(O) | 0 | N | none | 2 | OH | |
| 824 | 4-amidinophenyl | 1 | benzyl | C(O) | 0 | N | none | 3 | OH | |
| 825 | 4-amidinophenyl | 1 | benzyl | C(O) | 0 | CH | none | 1 | OH | |
| 826 | 4-amidinophenyl | 1 | benzyl | C(O) | 0 | CH | none | 2 | OH | |
| 827 | 4-amidinophenyl | 1 | benzyl | C(O) | 0 | CH | none | 3 | OH | |
| 828 | 4-amidinophenyl | 1 | benzyl | C(O) | 0 | CH | O | 1 | OH | |
| 829 | 4-amidinophenyl | 1 | benzyl | C(O) | 0 | CH | O | 2 | OH | |
| 830 | 4-amidinophenyl | 1 | benzyl | C(O) | 0 | CH | O | 3 | OH | |
| 831 | 4-amidinophenyl | 1 | benzyl | C(O) | 0 | N | O | 1 | OH | |
| 832 | 4-amidinophenyl | 1 | benzyl | C(O) | 0 | N | O | 2 | OH | |
| 833 | 4-amidinophenyl | 1 | benzyl | C(O) | 0 | N | NH | 1 | OH | |
| 834 | 4-(N-methylamidino)phenyl | 1 | benzyl | C(O) | 0 | N | none | 1 | OH | |
| 835 | 4-(N-methylamidino)phenyl | 1 | benzyl | C(O) | 0 | N | none | 1 | OMe | |
| 836 | 4-(N-methylamidino)phenyl | 1 | benzyl | C(O) | 0 | N | none | 2 | OH | |
| 837 | 4-(N-methylamidino)phenyl | 1 | benzyl | C(O) | 0 | N | none | 3 | OH | |
| 838 | 4-(N-methylamidino)phenyl | 1 | benzyl | C(O) | 0 | CH | none | 1 | OH | |
| 839 | 4-(N-methylamidino)phenyl | 1 | benzyl | C(O) | 0 | CH | none | 2 | OH | |
| 840 | 4-(N-methylamidino)phenyl | 1 | benzyl | C(O) | 0 | CH | none | 3 | OH | |
| 841 | 4-(N-methylamidino)phenyl | 1 | benzyl | C(O) | 0 | CH | O | 1 | OH | |
| 842 | 4-(N-methylamidino)phenyl | 1 | benzyl | C(O) | 0 | CH | O | 2 | OH | |

TABLE 2-continued

| Ex No. | R¹—A | m | R³ | X | n | U | V | j | Y | MS [(M + 1)⁺] |
|---|---|---|---|---|---|---|---|---|---|---|
| 843 | 4-(N-methylamidino)phenyl | 1 | benzyl | C(O) | 0 | CH | O | 3 | OH | |
| 844 | 4-(N-methylamidino)phenyl | 1 | benzyl | C(O) | 0 | N | O | 1 | OH | |
| 845 | 4-(N-methylamidino)phenyl | 1 | benzyl | C(O) | 0 | N | O | 2 | OH | |
| 846 | 4-(N-methylamidino)phenyl | 1 | benzyl | C(O) | 0 | N | NH | 1 | OH | |
| 847 | 4-(N-butylamidino)phenyl | 1 | benzyl | C(O) | 0 | N | none | 1 | OH | |
| 848 | 4-(N-butylamidino)phenyl | 1 | benzyl | C(O) | 0 | N | none | 1 | OMe | |
| 849 | 4-(N-butylamidino)phenyl | 1 | benzyl | C(O) | 0 | N | none | 2 | OH | |
| 850 | 4-(N-butylamidino)phenyl | 1 | benzyl | C(O) | 0 | N | none | 3 | OH | |
| 851 | 4-(N-butylamidino)phenyl | 1 | benzyl | C(O) | 0 | CH | none | 1 | OH | |
| 852 | 4-(N-butylamidino)phenyl | 1 | benzyl | C(O) | 0 | CH | none | 2 | OH | |
| 853 | 4-(N-butylamidino)phenyl | 1 | benzyl | C(O) | 0 | CH | none | 3 | OH | |
| 854 | 4-(N-butylamidino)phenyl | 1 | benzyl | C(O) | 0 | CH | O | 1 | OH | |
| 855 | 4-(N-butylamidino)phenyl | 1 | benzyl | C(O) | 0 | CH | O | 2 | OH | |
| 856 | 4-(N-butylamidino)phenyl | 1 | benzyl | C(O) | 0 | CH | O | 3 | OH | |
| 857 | 4-(N-butylamidino)phenyl | 1 | benzyl | C(O) | 0 | N | O | 1 | OH | |
| 858 | 4-(N-butylamidino)phenyl | 1 | benzyl | C(O) | 0 | N | O | 2 | OH | |
| 859 | 4-(N-butylamidino)phenyl | 1 | benzyl | C(O) | 0 | N | NH | 1 | OH | |
| 860 | 4-(N-butylamidino)phenyl | 0 | benzyl | C(O) | 1 | N | none | 1 | OH | |
| 861 | 4-(N-butylamidino)phenyl | 0 | benzyl | C(O) | 1 | N | none | 1 | OMe | |
| 862 | 4-(N-butylamidino)phenyl | 0 | benzyl | C(O) | 1 | N | none | 2 | OH | |
| 863 | 4-(N-butylamidino)phenyl | 0 | benzyl | C(O) | 1 | N | none | 3 | OH | |
| 864 | 4-(N-butylamidino)phenyl | 0 | benzyl | C(O) | 1 | CH | none | 1 | OH | |
| 865 | 4-(N-butylamidino)phenyl | 0 | benzyl | C(O) | 1 | CH | none | 2 | OH | |
| 866 | 4-(N-butylamidino)phenyl | 0 | benzyl | C(O) | 1 | CH | none | 3 | OH | |
| 867 | 4-(N-butylamidino)phenyl | 0 | benzyl | C(O) | 1 | CH | O | 1 | O | |
| 868 | 4-(N-butylamidino)phenyl | 0 | benzyl | C(O) | 1 | CH | O | 2 | OH | |
| 869 | 4-(N-butylamidino)phenyl | 0 | benzyl | C(O) | 1 | CH | O | 3 | OH | |
| 870 | 4-(N-butylamidino)phenyl | 0 | benzyl | C(O) | 1 | N | O | 1 | OH | |
| 871 | 4-(N-butylamidino)phenyl | 0 | benzyl | C(O) | 1 | N | O | 2 | OH | |
| 872 | 4-(N-butylamidino)phenyl | 0 | benzyl | C(O) | 0 | N | NH | 1 | OH | |
| 873 | 4-piperidinyl | 1 | benzyl | C(O) | 0 | N | none | 1 | OH | |
| 874 | 4-piperidinyl | 1 | benzyl | C(O) | 0 | N | none | 1 | OMe | |
| 875 | 4-piperidinyl | 1 | benzyl | C(O) | 0 | N | none | 2 | OH | |
| 876 | 4-piperidinyl | 1 | benzyl | C(O) | 0 | N | none | 3 | OH | |
| 877 | 4-piperidinyl | 1 | benzyl | C(O) | 0 | CH | none | 1 | OH | |
| 878 | 4-piperidinyl | 1 | benzyl | C(O) | 0 | CH | none | 2 | OH | |

TABLE 2-continued

| Ex No. | R¹—A | m | R³ | X | n | U | V | j | Y | MS [(M + 1)⁺] |
|---|---|---|---|---|---|---|---|---|---|---|
| 879 | 4-piperidinyl | 1 | benzyl | C(O) | 0 | CH | none | 3 | OH | |
| 880 | 4-piperidinyl | 1 | benzyl | C(O) | 0 | CH | O | 1 | OH | |
| 881 | 4-piperidinyl | 1 | benzyl | C(O) | 0 | CH | O | 2 | OH | |
| 882 | 4-piperidinyl | 1 | benzyl | C(O) | 0 | CH | O | 3 | OH | |
| 883 | 4-piperidinyl | 1 | benzyl | C(O) | 0 | N | O | 1 | OH | |
| 884 | 4-piperidinyl | 1 | benzyl | C(O) | 0 | N | O | 2 | OH | |
| 885 | 4-piperidinyl | 1 | benzyl | C(O) | 0 | N | NH | 1 | OH | |
| 886 | 4-piperidinyl | 1 | benzyl | C(O) | 0 | N | none | 1 | OH | |
| 887 | 4-piperidinyl | 2 | benzyl | C(O) | 0 | N | none | 1 | OMe | |
| 888 | 4-piperidinyl | 2 | benzyl | C(O) | 0 | N | none | 2 | OH | |
| 889 | 4-piperidinyl | 2 | benzyl | C(O) | 0 | N | none | 3 | OH | |
| 890 | 4-piperidinyl | 2 | benzyl | C(O) | 0 | CH | none | 1 | OH | |
| 891 | 4-piperidinyl | 2 | benzyl | C(O) | 0 | CH | none | 2 | OH | |
| 892 | 4-piperidinyl | 2 | benzyl | C(O) | 0 | CH | none | 3 | OH | |
| 893 | 4-piperidinyl | 2 | benzyl | C(O) | 0 | CH | O | 1 | OH | |
| 894 | 4-piperidinyl | 2 | benzyl | C(O) | 0 | CH | O | 2 | OH | |
| 895 | 4-piperidinyl | 2 | benzyl | C(O) | 0 | CH | O | 3 | OH | |
| 896 | 4-piperidinyl | 2 | benzyl | C(O) | 0 | N | O | 1 | OH | |
| 897 | 4-piperidinyl | 2 | benzyl | C(O) | 0 | N | O | 2 | OH | |
| 898 | 4-piperidinyl | 2 | benzyl | C(O) | 0 | N | NH | 1 | OH | |
| 899 | 4-piperidinyl | 2 | benzyl | C(O) | 1 | N | none | 1 | OH | |
| 900 | 4-piperidinyl | 2 | benzyl | C(O) | 1 | N | none | 1 | OMe | |
| 901 | 4-piperidinyl | 2 | benzyl | C(O) | 1 | N | none | 2 | OH | |
| 902 | 4-piperidinyl | 2 | benzyl | C(O) | 1 | N | none | 3 | OH | |
| 903 | 4-piperidinyl | 2 | benzyl | C(O) | 1 | CH | none | 1 | OH | |
| 904 | 4-piperidinyl | 2 | benzyl | C(O) | 1 | CH | none | 2 | OH | |
| 905 | 4-piperidinyl | 2 | benzyl | C(O) | 1 | CH | none | 3 | OH | |
| 906 | 4-piperidinyl | 2 | benzyl | C(O) | 1 | CH | O | 1 | OH | |
| 907 | 4-piperidinyl | 2 | benzyl | C(O) | 1 | CH | O | 2 | OH | |
| 908 | 4-piperidinyl | 2 | benzyl | C(O) | 1 | CH | O | 3 | OH | |
| 909 | 4-piperidinyl | 2 | benzyl | C(O) | 1 | N | O | 1 | OH | |
| 910 | 4-piperidinyl | 2 | benzyl | C(O) | 1 | N | O | 2 | OH | |
| 911 | 4-piperidinyl | 2 | benzyl | C(O) | 1 | N | NH | 1 | OH | |
| 912 | 4-amidinophenyl | 0 | Me | none | 1 | N | none | 1 | OH | |
| 913 | 4-amidinophenyl | 0 | Me | none | 1 | N | none | 1 | OMe | |
| 914 | 4-amidinophenyl 4-R, 6-S | 0 | Me | none | 1 | N | none | 1 | OH | |
| 915 | 4-amidinophenyl | 0 | Me | none | 1 | N | none | 2 | OH | |
| 916 | 4-amidinophenyl | 0 | Me | none | 1 | N | none | 3 | OH | |
| 917 | 4-amidinophenyl | 0 | Me | none | 1 | CH | none | 1 | OH | |
| 918 | 4-amidinophenyl | 0 | Me | none | 1 | CH | none | 2 | OH | |
| 919 | 4-amidinophenyl | 0 | Me | none | 1 | CH | none | 3 | OH | |
| 920 | 4-amidinophenyl | 0 | Me | none | 1 | CH | O | 1 | OH | |
| 921 | 4-amidinophenyl | 0 | Me | none | 1 | CH | O | 2 | OH | |
| 922 | 4-amidinophenyl | 0 | Me | none | 1 | CH | O | 3 | OH | |
| 923 | 4-amidinophenyl | 0 | Me | none | 1 | N | O | 1 | OH | |
| 924 | 4-amidinophenyl | 0 | Me | none | 1 | N | O | 2 | OH | |
| 925 | 4-amidinophenyl | 0 | Me | | 1 | N | NH | 1 | OH | |
| 926 | 4-amidinophenyl | 0 | Me | none | 0 | N | none | 1 | OH | |
| 927 | 4-amidinophenyl | 0 | Me | none | 0 | N | none | 1 | OMe | |
| 928 | 4-amidinophenyl | 0 | Me | none | 0 | N | none | 2 | OH | |
| 929 | 4-amidinophenyl | 0 | Me | none | 0 | N | none | 3 | OH | |
| 930 | 4-amidinophenyl | 0 | Me | none | 0 | CH | none | 1 | OH | |
| 931 | 4-amidinophenyl | 0 | Me | none | 0 | CH | none | 2 | OH | |
| 932 | 4-amidinophenyl | 0 | Me | none | 0 | CH | none | 3 | OH | |
| 933 | 4-amidinophenyl | 0 | Me | none | 0 | CH | O | 1 | OH | |
| 934 | 4-amidinophenyl | 0 | Me | none | 0 | CH | O | 2 | OH | |
| 935 | 4-amidinophenyl | 0 | Me | none | 0 | CH | O | 3 | OH | |
| 936 | 4-amidinophenyl | 0 | Me | none | 0 | N | O | 1 | OH | |
| 937 | 4-amidinophenyl | 0 | Me | none | 0 | N | O | 2 | OH | |
| 938 | 4-amidinophenyl | 0 | Me | none | 0 | N | NH | 1 | OH | |
| 939 | 4-amidinophenyl | 1 | Me | | 0 | N | none | 1 | OH | |
| 940 | 4-amidinophenyl | 1 | Me | none | 0 | N | none | 1 | OMe | |
| 941 | 4-amidinophenyl | 1 | Me | none | 0 | N | none | 2 | OH | |
| 942 | 4-amidinophenyl | 1 | Me | none | 0 | N | none | 3 | OH | |
| 943 | 4-amidinophenyl | 1 | Me | none | 0 | CH | none | 1 | OH | |

TABLE 2-continued

| Ex No. | R¹—A | m | R³ | X | n | U | V | j | Y | MS [(M + 1)⁺] |
|---|---|---|---|---|---|---|---|---|---|---|
| 944 | 4-amidinophenyl | 1 | Me | none | 0 | CH | none | 2 | OH | |
| 945 | 4-amidinophenyl | 1 | Me | none | 0 | CH | none | 3 | OH | |
| 946 | 4-amidinophenyl | 1 | Me | none | 0 | CH | O | 1 | OH | |
| 948 | 4-amidinophenyl | 1 | Me | none | 0 | CH | O | 2 | OH | |
| 949 | 4-amidinophenyl | 1 | Me | none | 0 | CH | O | 3 | OH | |
| 950 | 4-amidinophenyl | 1 | Me | none | 0 | N | O | 1 | OH | |
| 951 | 4-amidinophenyl | 1 | Me | none | 0 | N | O | 2 | OH | |
| 952 | 4-amidinophenyl | 1 | Me | none | 0 | N | NH | 1 | OH | |
| 953 | 4-amidinophenyl | 1 | Et | none | 0 | N | none | 1 | OH | |
| 954 | 4-amidinophenyl | 1 | Et | none | 0 | N | none | 1 | OMe | |
| 955 | 4-amidinophenyl | 1 | Et | none | 0 | N | none | 2 | OH | |
| 956 | 4-amidinophenyl | 1 | Et | none | 0 | N | none | 3 | OH | |
| 957 | 4-amidinophenyl | 1 | Et | none | 0 | CH | none | 1 | OH | |
| 958 | 4-amidinophenyl | 1 | Et | none | 0 | CH | none | 2 | OH | |
| 959 | 4-amidinophenyl | 1 | Et | none | 0 | CH | none | 3 | OH | |
| 960 | 4-amidinophenyl | 1 | Et | none | 0 | CH | O | 1 | OH | |
| 961 | 4-amidinophenyl | 1 | Et | none | 0 | CH | O | 2 | OH | |
| 962 | 4-amidinophenyl | 1 | Et | none | 0 | CH | O | 3 | OH | |
| 963 | 4-amidinophenyl | 1 | Et | none | 0 | N | O | 1 | OH | |
| 964 | 4-amidinophenyl | 1 | Et | none | 0 | N | O | 2 | OH | |
| 965 | 4-amidinophenyl | 1 | Et | none | 0 | N | NH | 1 | OH | |
| 966 | 4-amidinophenyl | 1 | benzyl | none | 0 | N | none | 1 | OH | |
| 967 | 4-amidinophenyl | 1 | benzyl | none | 0 | N | none | 1 | OMe | |
| 968 | 4-amidinophenyl | 1 | benzyl | none | 0 | N | none | 2 | OH | |
| 969 | 4-amidinophenyl | 1 | benzyl | none | 0 | N | none | 3 | OH | |
| 970 | 4-amidinophenyl | 1 | benzyl | none | 0 | CH | none | 1 | OH | |
| 971 | 4-amidinophenyl | 1 | benzyl | none | 0 | CH | none | 2 | OH | |
| 972 | 4-amidinophenyl | 1 | benzyl | none | 0 | CH | none | 3 | OH | |
| 973 | 4-amidinophenyl | 1 | benzyl | none | 0 | CH | O | 1 | OH | |
| 974 | 4-amidinophenyl | 1 | benzyl | none | 0 | CH | O | 2 | OH | |
| 975 | 4-amidinophenyl | 1 | benzyl | none | 0 | CH | O | 3 | OH | |
| 976 | 4-amidinophenyl | 1 | benzyl | none | 0 | N | O | 1 | OH | |
| 977 | 4-amidinophenyl | 1 | benzyl | none | 0 | N | O | 2 | OH | |
| 978 | 4-amidinophenyl | 1 | benzyl | none | 0 | N | NH | 1 | OH | |
| 979 | 4-(N-methylamidino)phenyl | 1 | benzyl | none | 0 | N | none | 1 | OH | |
| 980 | 4-(N-methylamidino)phenyl | 1 | benzyl | none | 0 | N | none | 1 | OMe | |
| 981 | 4-(N-methylamidino)phenyl | 1 | benzyl | none | 0 | N | none | 2 | OH | |
| 982 | 4-(N-methylamidino)phenyl | 1 | benzyl | none | 0 | N | none | 3 | OH | |
| 983 | 4-(N-methylamidino)phenyl | 1 | benzyl | none | 0 | CH | none | 1 | OH | |
| 984 | 4-(N-methylamidino)phenyl | 1 | benzyl | none | 0 | CH | none | 2 | OH | |
| 985 | 4-(N-methylamidino)phenyl | 1 | benzyl | none | 0 | CH | none | 3 | OH | |
| 986 | 4-(N-methylamidino)phenyl | 1 | benzyl | none | 0 | CH | O | 1 | OH | |
| 987 | 4-(N-methylamidino)phenyl | 1 | benzyl | none | 0 | CH | O | 2 | OH | |
| 988 | 4-(N-methylamidino)phenyl | 1 | benzyl | none | 0 | CH | O | 3 | OH | |
| 989 | 4-(N-methylamidino)phenyl | 1 | benzyl | none | 0 | N | O | 1 | OH | |
| 990 | 4-(N-methylamidino)phenyl | 1 | benzyl | none | 0 | N | O | 2 | OH | |
| 991 | 4-(N-methylamidino)phenyl | 1 | benzyl | none | 0 | N | NH | 1 | OH | |
| 992 | 4-(N-butylamidino)phenyl | 1 | benzyl | none | 0 | N | none | 1 | OH | |
| 993 | 4-(N-butylamidino)phenyl | 1 | benzyl | none | 0 | N | none | 1 | OMe | |
| 994 | 4-(N-butylamidino)phenyl | 1 | benzyl | none | 0 | N | none | 2 | OH | |

TABLE 2-continued

| Ex No. | R¹—A | m | R³ | X | n | U | V | j | Y | MS [(M + 1)⁺] |
|---|---|---|---|---|---|---|---|---|---|---|
| 995 | 4-(N-butylamidino)phenyl | 1 | benzyl | none | 0 | N | none | 3 | OH | |
| 996 | 4-(N-butylamidino)phenyl | 1 | benzyl | none | 0 | CH | none | 1 | OH | |
| 997 | 4-(N-butylamidino)phenyl | 1 | benzyl | none | 0 | CH | none | 2 | OH | |
| 998 | 4-(N-butylamidino)phenyl | 1 | benzyl | none | 0 | CH | none | 3 | OH | |
| 999 | 4-(N-butylamidino)phenyl | 1 | benzyl | none | 0 | CH | O | 1 | OH | |
| 1000 | 4-(N-butylamidino)phenyl | 1 | benzyl | none | 0 | CH | O | 2 | OH | |
| 1001 | 4-(N-butylamidino)phenyl | 1 | benzyl | none | 0 | CH | O | 3 | OH | |
| 1002 | 4-(N-butylamidino)phenyl | 1 | benzyl | none | 0 | N | O | 1 | OH | |
| 1003 | 4-(N-butylamidino)phenyl | 1 | benzyl | none | 0 | N | O | 2 | OH | |
| 1004 | 4-(N-butylamidino)phenyl | 1 | benzyl | none | 0 | N | NH | 1 | OH | |
| 1005 | 4-(N-butylamidino)phenyl | 0 | benzyl | none | 1 | N | none | 1 | OH | |
| 1006 | 4-(N-butylamidino)phenyl | 0 | benzyl | none | 1 | N | none | 1 | OMe | |
| 1007 | 4-(N-butylamidino)phenyl | 0 | benzyl | none | 1 | N | none | 2 | OH | |
| 1008 | 4-(N-butylamidino)phenyl | 0 | benzyl | none | 1 | N | none | 3 | OH | |
| 1009 | 4-(N-butylamidino)phenyl | 0 | benzyl | none | 1 | CH | none | 1 | OH | |
| 1010 | 4-(N-butylamidino)phenyl | 0 | benzyl | none | 1 | CH | none | 2 | OH | |
| 1011 | 4-(N-butylamidino)phenyl | 0 | benzyl | none | 1 | CH | none | 3 | OH | |
| 1012 | 4-(N-butylamidino)phenyl | 0 | benzyl | none | 1 | CH | O | 1 | OH | |
| 1013 | 4-(N-butylamidino)phenyl | 0 | benzyl | none | 1 | CH | O | 2 | OH | |
| 1014 | 4-(N-butylamidino)phenyl | 0 | benzyl | none | 1 | CH | O | 3 | OH | |
| 1015 | 4-(N-butylamidino)phenyl | 0 | benzyl | none | 1 | N | O | 1 | OH | |
| 1016 | 4-(N-butylamidino)phenyl | 0 | benzyl | none | 1 | N | O | 2 | OH | |
| 1017 | 4-(N-butylamidino)phenyl | 0 | benzyl | none | 0 | N | NH | 1 | OH | |
| 1018 | 4-piperidinyl | 1 | benzyl | none | 0 | N | none | 1 | OH | |
| 1019 | 4-piperidinyl | 1 | benzyl | none | 0 | N | none | 1 | OMe | |
| 1020 | 4-piperidinyl | 1 | benzyl | none | 0 | N | none | 2 | OH | |
| 1021 | 4-piperidinyl | 1 | benzyl | none | 0 | N | none | 3 | OH | |
| 1022 | 4-piperidinyl | 1 | benzyl | none | 0 | CH | none | 1 | OH | |
| 1023 | 4-piperidinyl | 1 | benzyl | none | 0 | CH | none | 2 | OH | |
| 1024 | 4-piperidinyl | 1 | benzyl | none | 0 | CH | none | 3 | OH | |
| 1025 | 4-piperidinyl | 1 | benzyl | none | 0 | CH | O | 1 | OH | |
| 1026 | 4-piperidinyl | 1 | benzyl | none | 0 | CH | O | 2 | OH | |
| 1027 | 4-piperidinyl | 1 | benzyl | none | 0 | CH | O | 3 | OH | |
| 1028 | 4-piperidinyl | 1 | benzyl | none | 0 | N | O | 1 | OH | |
| 1029 | 4-piperidinyl | 1 | benzyl | none | 0 | N | O | 2 | OH | |
| 1030 | 4-piperidinyl | 1 | benzyl | none | 0 | N | NH | 1 | OH | |
| 1031 | 4-piperidinyl | 2 | benzyl | none | 0 | N | none | 1 | OH | |
| 1032 | 4-piperidinyl | 2 | benzyl | none | 0 | N | none | 1 | OMe | |
| 1033 | 4-piperidinyl | 2 | benzyl | none | 0 | N | none | 2 | OH | |
| 1034 | 4-piperidinyl | 2 | benzyl | none | 0 | N | none | 3 | OH | |
| 1035 | 4-piperidinyl | 2 | benzyl | none | 0 | CH | none | 1 | OH | |
| 1036 | 4-piperidinyl | 2 | benzyl | none | 0 | CH | none | 2 | OH | |
| 1037 | 4-piperidinyl | 2 | benzyl | none | 0 | CH | none | 3 | OH | |

TABLE 2-continued

| Ex No. | R¹—A | m | R³ | X | n | U | V | j | Y | MS [(M + 1)⁺] |
|---|---|---|---|---|---|---|---|---|---|---|
| 1038 | 4-piperidinyl | 2 | benzyl | none | 0 | CH | O | 1 | OH | |
| 1039 | 4-piperidinyl | 2 | benzyl | none | 0 | CH | O | 2 | OH | |
| 1040 | 4-piperidinyl | 2 | benzyl | none | 0 | CH | O | 3 | OH | |
| 1041 | 4-piperidinyl | 2 | benzyl | none | 0 | N | O | 1 | OH | |
| 1042 | 4-piperidinyl | 2 | benzyl | none | 0 | N | O | 2 | OH | |
| 1043 | 4-piperidinyl | 2 | benzyl | none | 0 | N | NH | 1 | OH | |
| 1044 | 4-piperidinyl | 2 | benzyl | none | 1 | N | none | 1 | OH | |
| 1045 | 4-piperidinyl | 2 | benzyl | none | 1 | N | none | 1 | OMe | |
| 1046 | 4-piperidinyl | 2 | benzyl | none | 1 | N | none | 2 | OH | |
| 1048 | 4-piperidinyl | 2 | benzyl | none | 1 | N | none | 3 | OH | |
| 1049 | 4-piperidinyl | 2 | benzyl | none | 1 | CH | none | 1 | OH | |
| 1050 | 4-piperidinyl | 2 | benzyl | none | 1 | CH | none | 2 | OH | |
| 1051 | 4-piperidinyl | 2 | benzyl | none | 1 | CH | none | 3 | OH | |
| 1052 | 4-piperidinyl | 2 | benzyl | none | 1 | CH | O | 1 | OH | |
| 1053 | 4-piperidinyl | 2 | benzyl | none | 1 | CH | O | 2 | OH | |
| 1054 | 4-piperidinyl | 2 | benzyl | none | 1 | CH | O | 3 | OH | |
| 1055 | 4-piperidinyl | 2 | benzyl | none | 1 | N | O | 1 | OH | |
| 1056 | 4-piperidinyl | 2 | benzyl | none | 1 | N | O | 2 | OH | |
| 1057 | 4-piperidinyl | 2 | benzyl | none | 1 | N | NH | 1 | OH | |

Utility

The compounds of this invention possess antiplatelet efficacy, as evidenced by their activity in standard platelet aggregation assays or platelet fibrinogen binding assays, as described below. A compound is considered to be active in these assays if it has an $IC_{50}$ value of less than about 1 mM. Platelet aggregation and fibrinogen binding assays which may be used to demonstrate the antiplatelet activity of the compounds of the invention are described below.

Platelet Aggregation Assay: Venous blood was obtained from the arm of a healthy human donor who was drug-free and aspirin-free for at least two weeks prior to blood collection. Blood was collected into 10 mL citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 µL of PRP was added to each micro test tube, and transmittance was set to 0%. 20 µL of various agonists (ADP, collagen, arachidonate, epinephrine, thrombin) were added to each tube, and the aggregation profiles were plotted (% transmittance versus time). The results are expressed as % inhibition of agonist-induced platelet aggregation. For the $IC_{50}$ evaluation, the test compounds were added at various concentrations prior to the activation of the platelets.

Ester prodrugs were preincubated ($10^{-3}$ M F.C.) with 100 IU/mL Porcine liver esterase (Sigma Chemical Co., St. Louis, Mo., #E-3128) for 2 hours at 37° C. Aliquots are then diluted in 0.1 M Tris, pH 7.4, to the desired concentrations. Aliquots of 20 µl of the esterase pretreated prodrugs are added to 200 µl of human platelet rich plasma. Samples were placed in platelet profiler (aggregometer) for 8 minutes at 37° C., followed by the addition of 100 µM Adenosine Diphosphate, (Sigma Chemical Co., St. Louis, Mo., #A-6521), to induce platelet aggregation. Platelet aggregation was allowed to proceed for 5 minutes. Percent inhibition is calculated using percent aggregation in the presence of the test compound divided by percent aggregation of control, times 100. This value is subtracted from 100, yielding percent inhibition. Calculation of $IC_{50}$ is performed on a Texas Instruments TI59 with an $IC_{50}$ program.

Compounds of the present invention have demonstrated $IC_{50}$ values less than 1 µM.

Purified GPIIb/IIIa-Fibrinogen Binding ELISA

The following reagents are used in the GPIIb/IIIa-fibrinogen binding ELISA:

purified GPIIb/IIIa (148.8 µg/mL);
biotinylated fibrinogen (~1 mg/mL or 3000 nM);
anti-biotin alkaline phosphatase conjugate (Sigma no. A7418);
flat-bottom, high binding, 96-well plates (Costar Cat. no. 3590);
phosphatase substrate (Sigma 104) (40 mg capsules);
bovine serum albumin (BSA) (Sigma no. A3294);
Alkaline Phosphatase buffer–0.1 M glycine-HCl, 1 mM $MgCl_2.6H_2O$, 1 mM $ZnCl_2$, pH 10.4;
Binding buffer–20 mM Tris-HCl, 150 mM NaCl, 1 mM $CaCl_2.2H_2O$, 0.02% $NaN_3$, pH 7.0;
Buffer A–50 mM Tris-HCl, 100 mM NaCl, 2 mM $CaCl_2.2H_2O$, 0.02% $NaN_3$, pH 7.4;
Buffer A+3.5% BSA (Blocking buffer);
Buffer A+0.1% BSA (Dilution buffer);
2N NaOH.

The following method steps are used in the GPIIb/IIIa-fibrinogen binding ELISA:

Coat plates with GPIIb/IIIa in Binding buffer (125 ng/100 µL/well) overnight at 4° C. (Leave first column uncoated for non-specific binding). Cover and freeze plates at −70° C.

until used. Thaw plate 1 hour at room temperature or overnight at 4° C. Discard coating solution and wash once with 200 μL Binding buffer per well. Block plate 2 hours at room temperature on shaker with 200 μL Buffer A+3.5% BSA (Blocking buffer) per well. Discard Blocking buffer and wash once with 200 μL Buffer A+0.1% BSA (Dilution buffer) per well. Pipet 11 μL of test compound (10×the concentration to be tested in Dilution buffer) into duplicate wells. Pipet 11 μL Dilution buffer into non-specific and total binding wells. Add 100 μL Biotinylated fibrinogen (1/133 in Dilution buffer, final concentration=20 nM) to each well. Incubate plates for 3 hours at room temperature on a plate shaker. Discard assay solution and wash twice with 300 μL Binding buffer per well. Add 100 μL Anti-biotin alkaline phosphatase conjugate (1/1500 in Dilution buffer) to each well. Incubate plates for 1 hour at room temperature on plate shaker. Discard conjugate and wash twice with 300 5l Binding buffer per well. Add 100 μL Phosphatase substrate (1.5 mg/mL in Alkaline phosphatase buffer) to each well. Incubate plate at room temperature on shaker until color develops. Stop color development by adding 25 μL 2N NaOH per well. Read plate at 405 nm. Blank against non-specific binding (NSB) well. % Inhibition is calculated as 100−(Test Compound Abs/Total Abs)×100;

Platelet-Fibrinogen Binding Assay: Binding of $^{125}$I-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets ($5 \times 10^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated platelets was separated from the free form by centrifugation and then counted on a gamma counter. For an $IC_{50}$ evaluation, the test compounds were added at various concentrations prior to the activation of the platelets.

The compounds of Formula (I) of the present invention may also possess thrombolytic efficacy, that is, they are capable of lysing (breaking up) already formed platelet-rich fibrin blood clots, and thus are useful in treating a thrombus formation, as evidenced by their activity in the tests described below. Preferred compounds of the present invention for use in thrombolysis include those compounds having an $IC_{50}$ value (that is, the molar concentration of the compound capable of achieving 50% clot lysis) of less than about 1 μM, more preferably an $IC_{50}$ value of less than about 0.1 μM.

Thrombolytic Assay: Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500×g at room temperature, and platelet rich plasma (PRP) was removed. To the PRP was then added $1 \times 10^{-3}$ M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

The compounds of Formula (I) of the present invention are also useful for administration in combination with anti-coagulant agents such as warfarin or heparin, or anti-platelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof.

The compounds of Formula (I) of the present invention may also be useful as antagonists of other integrins such as for example, the $a_v/b_3$ or vitronectin receptor, $a_4/b_1$ or $a_5/b_1$ and as such may also have utility in the treatment and diagnosis of osteoporosis, cancer metastasis, diabetic retinopathy, rheumatoid arthritis, inflammation, and autoimmune disorders. The compounds of Formula (I) of the present invention may be useful for the treatment or prevention of other diseases which involve cell adhesion processes, including, but not limited to, infammation, bone degradation, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, inflammatory bowel disease and other autoimmune diseases.

Dosage and Formulation

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an anti-aggregation agent. Finally, the compounds of the invention may also be administered intranasally.

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin or ticlopidine which are agonist-specific. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. At ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences,* Mack Publishing Company, a standard reference text in this field.

Representative useful pharmaceutical dosage-forms for administration of the compounds of this invention can be illustrated as follows:

Capsules

A large number of unit capsules are prepared by filling standard two-piece hard gelatin capsules each with 1–20 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 1–20 milligrams of the active ingredient. The capsules are washed and dried.

Tablets

A large number of tablets are prepared by conventional procedures so that the dosage unit was 1–20 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 1–20 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent selected from: an anti-coagulant agent such as warfarin or heparin; an anti-platelet agent such as aspirin, piroxicam or ticlopidine; a thrombin inhibitor such as a boropeptide thrombin inhibitor, or hirudin; or a thrombolytic agent such as plasminogen activators, such as tissue plasminogen activator, anistreplase, urokinase or streptokinase. The compound of Formula (I) and such second therapeutic agent can be administered separately or as a physical combination in a single dosage unit, in any dosage form and by various routes of administration, as described above.

The compound of Formula (I) may be formulated together with the second therapeutic agent in a single dosage unit (that is, combined together in one capsule, tablet, powder, or liquid, etc.). When the compound of Formula (I) and the second therapeutic agent are not formulated together in a single dosage unit, the compound of Formula (I) and the second therapeutic agent (anti-coagulant agent, anti-platelet agent, thrombin inhibitor, and/or thrombolytic agent) may be administered essentially at the same time, or in any order; for example the compound of Formula (I) may be administered first, followed by administration of the second agent (anti-coagulant agent, anti-platelet agent, thrombin inhibitor, and/or thrombolytic agent). When not administered at the same time, preferably the administration of the compound of Formula (I) and the second therapeutic agent occurs less than about one hour apart.

A preferable route of administration of the compound of Formula (I) is oral. Although it is preferable that the compound of Formula (I) and the second therapeutic agent (anti-coagulant agent, anti-platelet agent, thrombin inhibitor, and/or thrombolytic agent) are both administered by the same route (that is, for example, both orally), if desired, they may each be administered by different routes and in different dosage forms (that is, for example, one component of the combination product may be administered orally, and another component may be administered intravenously).

The dosage of the compound of Formula (I) when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the compound of Formula (I) when administered in combination with the second therapeutic agent will be readily ascertainable by a medical practitioner skilled in the art, once armed with the present disclosure, by way of general guidance, where the compounds of this invention are combined with anti-coagulant agents, for example, a daily dosage may be about 0.1 to 100 milligrams of the compound of Formula (I) and about 1 to 7.5 milligrams of the anticoagulant, per kilogram of patient body weight. For a tablet dosage form, the novel compounds of this invention generally may be present in an amount of about 1 to 10 milligrams per dosage unit, and the anticoagulant in an amount of about 1 to 5 milligrams per dosage unit.

Where the compounds of Formula (I) are administered in combination with a second anti-platelet agent, by way of general guidance, typically a daily dosage may be about 0.01 to 25 milligrams of the compound of Formula (I) and about 50 to 150 milligrams of the additional anti-platelet agent, preferably about 0.1 to 1 milligrams of the compound of Formula (I) and about 1 to 3 milligrams of antiplatelet agents, per kilogram of patient body weight.

Further, by way of general guidance, where the compounds of Formula (I) are adminstered in combination with thrombolytic agent, typically a daily dosage may be about 0.1 to 1 milligrams of the compound of Formula (I), per kilogram of patient body weight and, in the case of the thrombolytic agents, the usual dosage of the thrombolyic agent when administered alone may be reduced by about 70–80% when administered with a compound of Formula (I).

Where two or more of the foregoing second therapeutic agents are administered with the compound of Formula (I), generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula (I) and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the inhibition of platelet aggregation, the treatment of blood clots, and/or the treatment of thromboembolic disorders, which comprise one or more containers containing a pharmaceutical composition comprising a therapeutically effective amount of a compound of Formula (I). Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

What is claimed is:

1. A compound of the Formula (I):

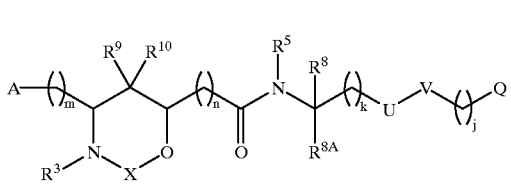

or their pharmaceutically acceptable salts thereof, wherein:

A is selected from $R^1$;
 phenyl substituted with $R^1$ and 0–2 $R^6$;
 piperidinyl substituted with 0–1 $R^1$ and 0–2 $R^6$; and
 pyridyl substituted with 0–1 $R^1$ and 0–2 $R^6$;

$R^1$ is —$NHR^2$, —$C(=NR^2)NHR^2$, —$Z(CH_2)_qNHR^2$, —$Z(CH_2)_qC(=NR^2)NHR^2$, —$N(R^2)C(=NR^2)NHR^2$, —$C(=O)NHR^2$, —$C(=NR^2)N(OR^{2A})R^2$, or —$C(=NOR^{2A})NHR^2$;

q is 1, 2, or 3;

Z is a bond, O, S, S(=O), or S(=O)$_2$;

$R^2$ is, independently at each occurence, H, $C_1$–$C_4$ alkyl, $C_2$–$C_6$ alkenyl, $C_1$–$C_{10}$ alkoxycarbonyl, or aryl($C_1$–$C_{10}$ alkoxy carbonyl;

$R^{2A}$ is H or $C_1$–$C_{10}$ alkyl substituted with 0–1 $R^4$;

$R^3$ is H,
 $C_1$–$C_6$ alkyl substituted with 0–1 $R^6$,
 $C_2$–$C_6$ alkenyl substituted with 0–1 $R^6$,
 $C_2$–$C_6$ alkynyl substituted with 0–1 $R^6$,
 $C_3$–$C_7$ cycloalkyl substituted with 0–2 $R^{6A}$,
 phenyl substituted with 0–2 $R^{6A}$, or
 pyridyl substituted with 0–2 $R^{6A}$;

X is —C(=O)—;

$R^4$ is $C_1$–$C_6$ alkyl, $C_2$–$C_6$ alkenyl, $C_2$–$C_6$ alkynyl, $C_3$–$C_7$ cycloalkyl, $C_7$–$C_{14}$ bicycloalkyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, $C_1$–$C_6$ alkylcarbonyl, $C_6$–$C_{10}$ aryl, —$N(R^{12})R^{13}$; halo, $CF_3$, CN, $NO_2$, $C_1$–$C_6$ alkoxycarbonyl, carboxy, piperidinyl, morpholinyl, or pyridinyl;

$R^5$ is H or $C_1$–$C_{10}$ alkyl substituted with 0–1 $R^4$;

$R^6$ is $C_3$–$C_7$ cycloalkyl substituted with 0–2 $R^{6A}$ or 0–6 $R^1$;
 phenyl substituted with 0–2 $R^{6A}$ or 0–1 $R^1$; or
 pyridyl substituted with 0–2 $R^{6A}$ or 0–1 $R^1$;

$R^{6A}$ is $C_1$–$C_4$ alkyl, $C_1$–$C_4$ alkoxy, halo, $CF_3$, $NO_2$ or $NR^{12}R^{13}$;

U is —$C(R^7)(R^{7A})$— or —$N(R^7)$—;

$R^7$ is selected from:
 H,
 $C_1$–$C_4$ alkyl substituted with 0–2 $R^{16}$,
 $C_2$–$C_4$ alkenyl substituted with 0–2 $R^{16}$,
 $C_2$–$C_4$ alkynyl substituted with 0–2 $R^{16}$,
 $C_3$–$C_6$ cycloalkyl substituted with 0–2 $R^{16}$,
 $C_3$–$C_6$ cycloalkyl($C_1$–$C_4$ alkyl) substituted with 0–2 $R^{16}$,
 aryl substituted with 0–4 $R^{16}$,
 aryl($C_1$–$C_4$ alkyl) substituted with 0–4 $R^{16}$,
 a 5–6 membered heterocyclic ring system having 1–3 heteroatoms selected independently from O,S, and N, said heterocyclic ring being substituted with 0–4 $R^{16}$, and
 $C_1$–$C_4$ alkyl substituted with a 5–6 membered heterocyclic ring system having 1–3 heteroatoms selected independently from O,S, and N, said heterocyclic ring being substituted with 0–4 $R^{16}$;

$R^{7A}$ is selected from:
 H,
 $C_1$–$C_4$ alkyl substituted with 0–2 $R^{16}$,
 $C_2$–$C_4$ alkenyl substituted with 0–2 $R^{16}$, and
 $C_2$–$C_4$ alkynyl substituted with 0–2 $R^{16}$;

$R^8$ is selected from:
 H,
 —$C(=O)N(R^{20})_2$,
 $C_1$–$C_6$ alkyl substituted with 0–2 $R^{16}$,
 $C_2$–$C_4$ alkenyl substituted with 0–2 $R^{16}$,
 $C_2$–$C_4$ alkynyl substituted with 0–2 $R^{16}$,
 $C_3$–$C_6$ cycloalkyl substituted with 0–2 $R^{16}$,
 aryl substituted with 0–4 $R^{16}$,
 aryl($C_1$–$C_4$ alkyl) substituted with 0–4 $R^{16}$,
 a 5–6 membered heterocyclic ring system having 1–3 heteroatoms selected independently from O,S, and N, said heterocyclic ring being substituted with 0–4 $R^{16}$, and
 $C_1$–$C_4$ alkyl substituted with a 5–10 membered heterocyclic ring system having 1–3 heteroatoms selected independently from O,S, and N, said heterocyclic ring being substituted with 0–4 $R^{16}$;

alternatively, $R^5$ and $R^8$ are taken together to form a piperidinyl or a pyrrolidinyl ring;

alternatively, $R^7$ and $R^8$ are taken together to form a 5–6 membered carbocyclic ring, wherein said carbocyclic ring is either saturated, partially unsaturated or aromatic;

$R^{8A}$ is selected from:
 H,
 $C_1$–$C_4$ alkyl substituted with 0–2 $R^{16}$,
 $C_2$–$C_4$ alkenyl substituted with 0–2 $R^{16}$, and
 $C_2$–$C_4$ alkynyl substituted with 0–2 $R^{16}$;

k is 0 or 1;

j is 0, 1, 2, or 3;

V is O, NH, or a single bond;

Q is —$C(=O)Y$, —$SO_3H$, or —$PO_3H$;

Y is hydroxy,
 $C_1$–$C_{10}$ alkyloxy, $C_3$–$C_{11}$ cycloalkyloxy,
$C_6$–$C_{10}$ aryloxy,
$C_7$–$C_{11}$ aralkyloxy,
$C_3$–$C_{10}$ alkylcarbonyloxyalkyloxy,
$C_3$–$C_{10}$ alkoxycarbonyloxyalkyloxy,
$C_2$–$C_{10}$ alkoxycarbonylalkyloxy,
$C_5$–$C_{10}$ cycloalkylcarbonyloxyalkyloxy,
$C_5$–$C_{10}$ cycloalkoxycarbonyloxyalkyloxy,
$C_5$–$C_{10}$ cycloalkoxycarbonylalkyloxy,
$C_7$–$C_{11}$ aryloxycarbonylalkyloxy,
$C_8$–$C_{12}$ aryloxycarbonyloxyalkyloxy,
$C_8$–$C_{12}$ arylcarbonyloxyalkyloxy,
$C_5$–$C_{10}$ alkoxyalkylcarbonyloxyalkyloxy,
$C_5$–$C_{10}$ (5-alkyl-1,3-dioxa-cyclopenten-2-one-yl) methyloxy,
$C_{10}$–$C_{14}$ (5-aryl-1,3-dioxa-cyclopenten-2-one-yl) methyloxy, or
$(R^2)HN$—$(C_1$–$C_{10}$ alkyl)oxy;

m is 0, 1, or 2;
n is 0, 1, 2, 3, or 4;
$R^9$ and $R^{10}$ are each independently H, $C_1$–$C_6$ alkyl, $C_2$–$C_6$ alkenyl, $C_2$–$C_6$ alkynyl, $C_3$–$C_7$ cycloalkyl, phenyl substituted with 0–2 $R^{6A}$, or pyridyl substituted with 0–2 $R^{6A}$;

$R^{12}$ and $R^{13}$ are each independently H, $C_1$–$C_{10}$ alkyl, $C_1$–$C_{10}$ alkoxycarbonyl, $C_1$–$C_{10}$ alkylcarbonyl, $C_1$–$C_{10}$ alkylsulfonyl, heteroaryl($C_1$–$C_4$ alkyl)sulfonyl, aryl($C_1$–$C_{10}$ alkyl)sulfonyl, arylsulfonyl, aryl, heteroarylcarbonyl, heteroarylsulfonyl, or heteroarylalkylcarbonyl, wherein said aryls and heteroaryls are optionally substituted with 0–3 substituents selected from the group consisting of $C_1$–$C_4$ alkyl, $C_1$–$C_4$ alkoxy, halo, $CF_3$, and $NO_2$;

$R^{16}$ is H, halogen, —$CF_3$, —CN, —$NO_2$, —$NR^{17}R^{18}$, methyl, ethyl, propyl, butyl, cyclopropyl, methoxy, ethoxy, propoxy, butoxy, or $C_1$–$C_4$ alkoxycarbonyl;

$R^{17}$ and $R^{18}$ are each independently H, methyl, ethyl, propyl, or butyl;
alternatively, $R^{17}$ and $R^{18}$ can be taken together to form —($CH_2$)$_4$—, —($CH_2$)$_5$—, or —$CH_2CH_2NHCH_2CH_2$—;

$R^{20}$ is selected from:
H,
$C_1$–$C_4$ alkyl substituted with 0–1 $R^{21}$,
$C_3$–$C_6$ cycloalkyl substituted with 0–2 $R^{21}$,
aryl substituted with 0–3 $R^{21}$, and
aryl($C_1$–$C_4$ alkyl) substituted with 0–4 $R^{21}$; and $R^{21}$ is H, halogen, —$CF_3$, —CN, —$NR^{17}R^{18}$, methyl, ethyl, propyl, butyl, cyclopropyl, methoxy, ethoxy, propoxy, or butoxy;

provided that m and n are chosen such that the number of atoms connecting $R^1$ and Y is in the range of 10–18.

2. A compound according to claim 1, wherein;
A is selected from $R^1$;
phenyl substituted with $R^1$ and 0–2 $R^6$;
piperidinyl substituted with 0–1 $R^1$ and 0–2 $R^6$; and
pyridyl substituted with 0–1 $R^1$ and 0–2 $R^6$;

$R^1$ is —$NHR^2$, —C(=$NR^2$)$NHR^2$, —Z($CH_2$)$_q$$NHR^2$, —Z($CH_2$)$_q$C(=$NR^2$)$NHR^2$, —N($R^2$)C(=$NR^2$)$NHR^2$, —C(=$NR^2$)N(O$R^{24}$)$R^2$, or —C(=NO$R^{24}$)$NHR^2$;
q is 1, 2 or, 3;
Z is a bond or O;
$R^2$ is, independently at each occurence, H, $C_1$–$C_4$ alkyl, $C_2$–$C_4$ alkenyl, $C_1$–$C_6$ alkoxycarbonyl, or aryl($C_1$–$C_6$ alkoxy)carbonyl;

$R^{2A}$ is H or $C_1$–$C_6$ alkyl substituted with 0–1 $R^4$;
$R^3$ is H,
$C_1$–$C_4$ alkyl substituted with 0–1 $R^6$,
$C_2$–$C_4$ alkenyl substituted with 0–1 $R^6$,
$C_2$–$C_4$ alkynyl substituted with 0–1 $R^6$,
$C_3$–$C_6$ cycloalkyl substituted with 0–2 $R^{6A}$,
phenyl substituted with 0–2 $R^{6A}$, or
pyridyl substituted with 0–2 $R^{6A}$;

X is —C(=O)—;

$R^4$ is $C_1$–$C_4$ alkyl, $C_2$–$C_4$ alkenyl, $C_2$–$C_4$ alkynyl, $C_3$–$C_6$ cycloalkyl, $C_7$–$C_{12}$ bicycloalkyl, hydroxy, $C_1$–$C_4$ alkoxy, $C_1$–$C_4$ alkylthio, $C_1$–$C_4$ alkylsulfinyl, $C_1$–$C_4$ alkylsulfonyl, nitro, $C_1$–$C_4$ alkylcarbonyl, $C_6$–$C_{10}$ aryl, —N($R^{12}$)$R^{13}$; halo, $CF_3$, CN, $NO_2$, $C_1$–$C_5$ alkoxycarbonyl, carboxy, piperidinyl, morpholinyl, or pyridinyl;

$R^5$ is H or $C_1$–$C_6$ alkyl substituted with 0–1 $R^4$;
$R^6$ is $C_3$–$C_7$ cycloalkyl substituted with 0–2 $R^{6A}$ or 0–1 $R^1$;
phenyl substituted with 0–2 $R^{6A}$ or 0–1 $R^1$; or
pyridyl substituted with 0–2 $R^{6A}$ or 0–1 $R^1$;

$R^{6A}$ is $C_1$–$C_4$ alkyl, $C_1$–$C_4$ alkoxy, halo, $CF_3$, $NO_2$, or $NR^{12}R^{13}$;

U is —C($R^7$)($R^{7A}$)— or —N($R^7$)—;
$R^7$ is selected from:
H,
$C_1$–$C_4$ alkyl substituted with 0–1 $R^{16}$,
$C_2$–$C_4$ alkenyl substituted with 0–1 $R^{16}$,
$C_2$–$C_4$ alkynyl substituted with 0–1 $R^{16}$,
$C_3$–$C_6$ cycloalkyl substituted with 0–2 $R^{16}$,
$C_3$–$C_6$ cycloalkyl($C_1$–$C_4$ alkyl) substituted with 0–1 $R^{16}$,
aryl substituted with 0–4 $R^{16}$, and
aryl($C_1$–$C_4$ alkyl) substituted with 0–4 $R^{16}$;

$R^{7A}$ is H;

$R^8$ is selected from:
H,
—C(=O)$NHR^{20}$,
$C_1$–$C_6$ alkyl substituted with 0–1 $R^{16}$,
$C_2$–$C_4$ alkenyl substituted with 0–1 $R^{16}$,
$C_2$–$C_4$ alkynyl substituted with 0–1 $R^{16}$,
$C_3$–$C_6$ cycloalkyl substituted with 0–2 $R^{16}$,
aryl substituted with 0–4 $R^{16}$,
aryl($C_1$–$C_4$ alkyl) substituted with 0–4 $R^{16}$,
a 5–6 membered heterocyclic ring system having 1–3 heteroatoms selected independently from O,S, and N, said heterocyclic ring being substituted with 0–4 $R^{16}$, and
$C_1$–$C_4$ alkyl substituted with a 5–10 membered heterocyclic ring system having 1–3 heteroatoms selected independently from O,S, and N, said heterocyclic ring being substituted with 0–4 $R^{16}$;

alternatively, $R^5$ and $R^8$ are taken together to form a piperidinyl or a pyrrolidinyl ring;
alternatively, $R^7$ and $R^8$ are taken together to form a 5–6 membered carbocyclic ring, wherein said carbocyclic ring is selected from phenyl, cyclohexyl, cyclopentyl, cyclohexenyl, or cyclopentenyl;

$R^{8A}$ is H or $C_1$–$C_4$ alkyl substituted with 0–1 $R^{16}$;
k is 0 or 1;
j is 0, 1, or 2;
V is O or a single bond;
Q is —C(=O)Y or —$SO_3H$;
Y is hydroxy, $C_1$–$C_{10}$ alkyloxy,
$C_3$–$C_{11}$ cycloalkoxy,
$C_6$–$C_{10}$ aryloxy,
$C_7$–$C_{11}$ aralkyloxy,
$C_3$–$C_{10}$ alkylcarbonyloxyalkyloxy,
$C_3$–$C_{10}$ alkoxycarbonyloxyalkyloxy,
$C_2$–$C_{10}$ alkoxycarbonylalkyloxy,
$C_5$–$C_{10}$ cycloalkylcarbonyloxyalkyloxy,
$C_5$–$C_{10}$ cycloalkoxycarbonyloxyalkyloxy,
$C_5$–$C_{10}$ cycloalkoxycarbonylalkyloxy,
$C_7$–$C_{11}$ aryloxycarbonylalkyloxy,
$C_8$–$C_{12}$ aryloxycarbonyloxyalkyloxy,
$C_8$–$C_{12}$ arylcarbonyloxyalkyloxy,
$C_5$–$C_{10}$ alkoxyalkylcarbonyloxyalkyloxy,
$C_5$–$C_{10}$ (5-alkyl-1,3-dioxa-cyclopenten-2-one-yl) methyloxy,
$C_{10}$–$C_{14}$ (5-aryl-1,3-dioxa-cyclopenten-2-one-yl) methyloxy, or
$(R^2)HN$—$(C_1$–$C_{10}$ alkyl)oxy;

m is 0, 1, or 2;

n is 0, 1, 2, or 3;

$R^9$ is H, $C_1$–$C_4$ alkyl, $C_2$–$C_4$ alkenyl, $C_2$–$C_4$ alkynyl, $C_3$–$C_6$ cycloalkyly, phenyl substituted with 0–2 $R^{6A}$, or pyridyl substituted with 0–2 $R^{6A}$;

$R^{10}$ is H, methyl, ethyl, propyl, or butyl;

$R^{12}$ and $R^{13}$ are each independently H, $C_1$–$C_6$ alkyl, $C_1$–$C_6$ alkoxycarbonyl, $C_1$–$C_6$ alkylcarbonyl, $C_1$–$C_6$ alkylsulfonyl, heteroaryl($C_1$–$C_4$ alkyl)sulfonyl, aryl ($C_1$–$C_6$ alkyl)sulfonyl, arylsulfonyl, aryl, heteroarylcarbonyl, heteroarylsulfonyl, or heteroarylalkylcarbonyl, wherein said aryls and heteroaryls are optionally substituted with 0–3 substituents selected from the group consisting of $C_1$–$C_4$ alkyl, $C_1$–$C_4$ alkoxy, halo, $CF_3$, and $NO_2$;

$R^{16}$ is H, halogen, —$CF_3$, —CN, —$NO_2$, —$NR^{17}R^{18}$, methyl, ethyl, propyl, butyl, cyclopropyl, methoxy, ethoxy, propoxy, butoxy, or $C_1$–$C_4$ alkoxycarbonyl;

$R^{17}$ and $R^{18}$ are each independently H, methyl, ethyl, propyl, or butyl;

alternatively, $R^{17}$ and $R^{18}$ can be taken together to form —($CH_2$)$_4$—, —($CH_2$)$_5$—, or —$CH_2CH_2NHCH_2CH_2$—;

$R^{20}$ is selected from:
H,
$C_1$–$C_4$ alkyl substituted with 0–1 $R^{21}$,
$C_3$–$C_6$ cycloalkyl substituted with 0–2 $R^{21}$,
aryl substituted with 0–3 $R^{21}$, and
aryl($C_1$–$C_4$ alkyl) substituted with 0–3 $R^{21}$; and $R^{21}$ is H, halogen, —$CF_3$, —CN, —$NR^{17}R^{18}$, methyl, ethyl, propyl, butyl, cyclopropyl, methoxy, ethoxy, propoxy, or butoxy;

provided that m and n are chosen such that the number of atoms connecting $R^1$ and Y is in the range of 10–18.

3. A compound according to claim 1, wherein:

A is phenyl substituted with $R^1$ and 0–1 $R^6$, or piperidinyl substituted with 0–1 $R^6$;

$R^1$ is —$NHR^2$, —C(=$NR^2$)$NHR^2$, —($CH_2$)$_q$$NHR^2$, —($CH_2$)$_q$C(=$NR^2$)$NHR^2$, or —N($R^2$)C(=$NR^2$)$NHR^2$;

q is 1, 2, or 3;

$R^2$ is, independently at each occurence, H, methyl, ethyl, propyl, butyl, or $C_2$–$C_4$ alkenyl;

$R^3$ is H,
$C_1$–$C_4$ alkyl substituted with 0–1 $R^6$ or
$C_2$–$C_4$ alkenyl substituted with 0–1 $R^6$;

X is —C(=O)—;

$R^4$ is methyl, ethyl, propyl, butyl, methoxy, ethoxy, propoxy, or butoxy, fluoro, chloro, bromo, iodo, $CF_3$, $NO_2$, $NH_2$, or $N(CH_3)_2$;

$R^5$ is H or $C_1$–$C_2$ alkyl substituted with 0–1 $R^4$;

$R^6$ is $C_3$–$C_6$ cycloalkyl substituted with 0–2 $R^{6A}$;
phenyl substituted with 0–2 $R^{6A}$; or
pyridyl substituted with 0–2 $R^{6A}$;

$R^{6A}$ is methyl, ethyl, propyl, butyl, methoxy, ethoxy, propoxy, or butoxy, fluoro, chloro, bromo, iodo, $CF_3$, $NO_2$, $NH_2$, $N(CH_3)_2$, or $N(CH_2CH_3)_2$;

U is —C($R^7$)($R^{7A}$)— or —N($R^7$)—;

$R^7$ is selected from:
H, methyl, ethyl, propyl, and butyl;

$R^{7A}$ is H;

$R^8$ is selected from:
H,
—C(=O)$NHR^{20}$,
$C_1$–$C_6$ alkyl substituted with 0–1 $R^{16}$,
$C_2$–$C_4$ alkenyl substituted with 0–1 $R^{16}$,
$C_2$–$C_4$ alkynyl substituted with 0–1 $R^{16}$,
$C_3$–$C_6$ cycloalkyl substituted with 0–2 $R^{16}$,
aryl substituted with 0–4 $R^{16}$,
aryl($C_1$–$C_4$ alkyl) substituted with 0–2 $R^{16}$,
a 5–6 membered heterocyclic ring system having 1–3 heteroatoms selected independently from O,S, and N, said heterocyclic ring being substituted with 0–2 $R^{16}$, and
$C_1$–$C_4$ alkyl substituted with a 5–10 membered heterocyclic ring system having 1–3 heteroatoms selected independently from O,S, and N, said heterocyclic ring being substituted with 0–2 $R^{16}$;

$R^{8A}$ is H, methyl, ethyl, propyl, or butyl;

k is 0;

j is 0;

V is a single bond;

Q is —C(=O)Y;

Y is hydroxy-,
$C_1$–$C_4$ alkoxy-,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
t-butyloxycarbonyloxymethoxy-,
i-propyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-,
1-(2-(2-methoxypropyl)carbonyloxy)ethoxy-,
$(R^2)HN$—$(C_1$–$C_6$ alkyl)oxy-, m is 0 or 1;

n is 0 or 1;

$R^9$ is H, methyl, ethyl, propyl, butyl, phenyl substituted with 0–2 $R^6$, or pyridyl substituted with 0–2 $R^{6A}$;

$R^{10}$ is H;
$R^{16}$ is H, halogen, —$CF_3$, —CN, —$NO_2$, —$NR^{17}R^{18}$, methyl, ethyl, propyl, butyl, cyclopropyl, methoxy, ethoxy, propoxy or butoxy;
$R^{17}$ and $R^{18}$ are each independently H, methyl, ethyl, propyl or butyl.
$R^{20}$ is selected from:
  H,
  $C_1$–$C_3$ alkyl substituted with 0–1 $R^{21}$,
  $C_3$–$C_6$ cycloalkyl substituted with 0–1 $R^{21}$,
  aryl substituted with 0–2 $R^{21}$, and
  aryl($C_1$–$C_2$ alkyl) substituted with 0–2 $R^{21}$; and
$R^{21}$ is H, F, Cl, Br, I, —$CF_3$, —CN, $NH_2$, $N(CH_3)_2$, $N(CH_2CH_3)_2$, methyl, ethyl, cyclopropyl, methoxy, or ethoxy.

4. A compound according to claim 3 of Formula (Ia), wherein:

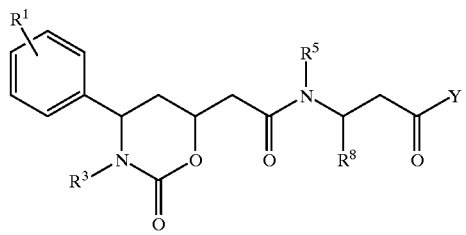

(Ia)

$R^1$ is —C(=$NR^2$)$NHR^2$, —($CH_2$)$_q$C(=$NR^2$)$NHR^2$ or —N($R^2$)C(=$NR^2$)$NHR^2$;
q is 1 or 2;
$R^2$ is, independently at each occurence, H, methyl or ethyl;
$R^3$ is H,
  methyl substituted with 0–1 $R^6$, or
  ethyl substituted with 0–1 $R^6$;
$R^5$ is H, methyl or ethyl;
$R^6$ is $C_3$–$C_6$ cycloalkyl substituted with 0–2 $R^{6A}$;
  phenyl substituted with 0–2 $R^{6A}$; or
  pyridyl substituted with 0–2 $R^{6A}$;
$R^{6A}$ is methyl, ethyl, propyl, butyl, methoxy, ethoxy, propoxy, or butoxy, fluoro, chloro, bromo, iodo, $CF_3$, $NO_2$, $NH_2$ or $N(CH_3)_2$;
$R^8$ is selected from:
  H,
  —C(=O)NHCH$_2$R$^{21}$,
  —C(=O)NH(CH$_2$)$_2$R$^{21}$,
  —C(=O)NH(CH$_2$)$_3$R$^{21}$,
  methyl substituted with 0–1 $R^{16}$,
  ethyl substituted with 0–1 $R^{16}$,
  phenyl substituted with 0–2 $R^{16}$,
  phenyl(CH$_2$)— substituted with 0–2 $R^{16}$,
  phenyl(CH$_2$CH$_2$)— substituted with 0–2 $R^{16}$,
  a 5–6 membered heterocyclic ring system selected from pyrrolyl, indolyl, 2-isobenzazolyl-, indazolyl, isoindazolyl, pyridinyl, quinolinyl, isoquinolinyl, and piperidinyl;
  methyl substituted with a 5–6 membered heterocyclic ring system selected from pyrrolyl, indolyl, 2-isobenzazolyl-, indazolyl, isoindazolyl, pyridinyl, quinolinyl, isoquinolinyl, and piperidinyl; and
  ethyl substituted with a 5–6 membered heterocyclic ring system selected from pyrrolyl, indolyl, 2-isobenzazolyl-, indazolyl, isoindazolyl, pyridinyl, quinolinyl, isoquinolinyl, and piperidinyl;

Y is hydroxy-, methoxy-, ethoxy-, n-butoxy-, isopropoxy-, isobutoxy-, benzyloxy-, methylcarbonyloxymethoxy-, ethylcarbonyloxymethoxy-, tert-butylcarbonyloxymethoxy-, cyclohexylcarbonyloxymethoxy-, tert-butyloxycarbonyloxymethoxy-, dimethylaminoethoxy-, diethylaminoethoxy-;
$R^{16}$ is H, halogen, —$CF_3$, methyl, ethyl, methoxy, ethoxy, —$NH_2$, —$N(CH_3)_2$, or —$N(CH_2CH_3)_2$;
$R^{17}$ and $R^{18}$ are each independently H, methyl, or ethyl; and
$R^{21}$ is H, F, Cl, Br, I, —$CF_3$, —CN, $NH_2$, $N(CH_3)_2$, $N(CH_2CH_3)_2$, methyl, ethyl, cyclopropyl, methoxy, or ethoxy.

5. A compound of claim 1 selected from the group consisting of:

3-[[4(S)-[4-(aminoiminomethyl)phenyl]tetrahydro-3-methyl-2-oxo-2H-1,3-oxazin-6(R)-yl]acetyl]aminopropionic acid;
3-[[4(R)-[4-(aminoiminomethyl)phenyl]tetrahydro-3-methyl-2-oxo-2H-1,3-oxazin-6(S)-yl]acetyl]amino propionic acid;
Trans-3-[[4-[4-(aminoiminomethyl)phenyl]tetrahydro-3-methyl-2-oxo-2H-1,3-oxazin-6-yl]acetyl]amino propionic acid;
3(R)-[[4(S)-[4-(aminoiminomethyl)phenyl]tetrahydro-3-methyl-2-oxo-2H-1,3-oxazin-6(R)-yl]acetyl]aminobutyric acid;
3(R)-[[4(S)-[4-(aminoiminomethyl)phenyl]tetrahydro-3-methyl-2-oxo-2H-1,3-oxazin-6(R)-yl]acetyl]amino-5-phenylvaleric acid;
3(S)-[[4(S)-[4-(aminoiminomethyl)phenyl]tetrahydro-3-methyl-2-oxo-2H-1,3-oxazin-6(R)-yl]acetyl]amino-3-(pyridin-3-yl)propionic acid;
3(R)-[[4(S)-[4-(aminoiminomethyl)phenyl]tetrahydro-3-methyl-2-oxo-2H-1,3-oxazin-6(R)-yl]acetyl]amino-3-(pyridin-3-yl)propionic acid;
3(S)-[[4(S)-[4-(aminoiminomethyl)phenyl]tetrahydro-3-methyl-2-oxo-2H-1,3-oxazin-6(R)-yl]acetyl]amino-3-phenylpropionic acid;
3(R)-[[4(S)-[4-(aminoiminomethyl)phenyl]tetrahydro-3-methyl-2-oxo-2H-1,3-oxazin-6(R)-yl]acetyl]amino-3-phenylpropionic acid;
3(R)-[[4(S)-[4-(aminoiminomethyl)phenyl]tetrahydro-3-methyl-2-oxo-2H-1,3-oxazin-6(R)-yl]acetyl]amino-4-[(3-dimethylamino)propyl]amino-4-oxobutanoic acid;
3(R)-[[4(S)-[4-(aminoiminomethyl)phenyl]tetrahydro-3-methyl-2-oxo-2H-1,3-oxazin-6(R)-yl]acetyl]amino-5-indole-3-valeric acid;
3-[[4(S)-[4-(aminoiminomethyl)phenyl]tetrahydro-3-benzyl-2-oxo-2H-1,3-oxazin-6(R)-yl]acetyl]aminopropionic acid;
3-[[4(R)-[4-(aminoiminomethyl)phenyl]tetrahydro-3-benzyl-2-oxo-2H-1,3-oxazin-6(S)-yl]acetyl]aminopropionic acid;
3(R)-[[4(S)-[4-(aminoiminomethyl)phenyl]tetrahydro-3-benzyl-2-oxo-2H-1,3-oxazin-6(R)-yl]acetyl]aminobutyric acid;
[N-[[4(S)-[4-(N-butylaminoiminomethyl)phenyl]tetrahydro-3-benzyl-2-oxo-2H-1,3-oxazin-6(R)-yl]acetyl]piperidin-4-yl]acetic acid;
3(R)-[[4(S)-[4-(N-butylaminoiminomethyl)phenyl]tetrahydro-3-methyl-2-oxo-2H-1,3-oxazin-6(R)-yl]acetyl]amino-5-phenylvaleric acid;
3-[[2-methyl-3(S)-[4-(aminoiminomethyl)phenyl]-isoxazolidin-5(R)-yl]acetyl]aminopropionic acid;

3-[[2-methyl-3(R)-[4-(aminoiminomethyl)phenyl]-isoxazolidin-5(S)-yl]acetyl]aminopropionic acid;
3(R)-[[2-methyl-3(R)-[4-(aminoiminomethyl)phenyl]-isoxazolidin-5(S)-yl]acetyl]aminobutyric acid; and
[N-[[4(S)-[4-(N-butylaminoiminomethyl)phenyl]tetrahydro-3-methyl-2-oxo-2H-1,3-oxazin-6(R)-yl]acetyl]piperidin-4-yl]acetic acid.

6. A compound of claim 1 of formula (II)

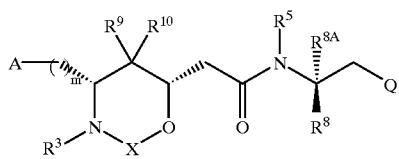

(II)

or their pharmaceutically acceptable salts thereof.

7. A compound of claim 2 of formula (II)

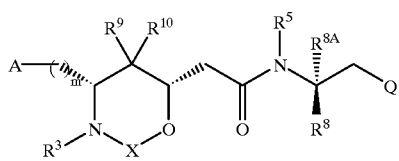

(II)

or their pharmaceutically acceptable salts thereof.

8. A compound of claim 3 of formula (II)

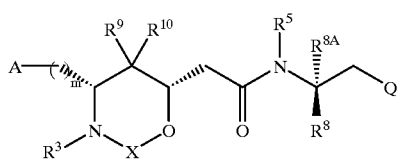

(II)

or their pharmaceutically acceptable salts thereof.

9. A compound of claim 4 of formula (IIa)

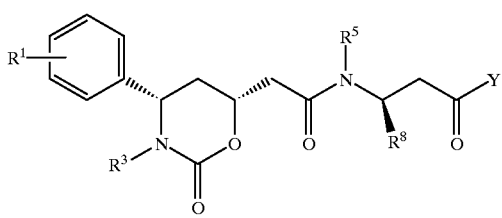

(IIa)

or their pharmaceutically acceptable salts thereof.

10. A pharmaceutical composition comprising a pharmaceutical carrier and a therapeutically effective amount of a compound of claim 1 or a pharmaceutically acceptable salt form thereof.

11. A pharmaceutical composition comprising a pharmaceutical carrier and a therapeutically effective amount of a compound of claim 2 or a pharmaceutically acceptable salt form thereof.

12. A pharmaceutical composition comprising a pharmaceutical carrier and a therapeutically effective amount of a compound of claim 3 or a pharmaceutically acceptable salt form thereof.

13. A pharmaceutical composition comprising a pharmaceutical carrier and a therapeutically effective amount of a compound of claim 4 or a pharmaceutically acceptable salt form thereof.

14. A pharmaceutical composition comprising a pharmaceutical carrier and a therapeutically effective amount of a compound of claim 5 or a pharmaceutically acceptable salt form thereof.

15. A method in inhibiting the aggregation of blood platelets which comprises administering to a host in need of such inhibition a therapeutically effective amount of a compound of claim 1.

16. A method of inhibiting the aggregation of blood platelets which comprises administering to a host in need of such inhibition a therapeutically effective amount of a compound of claim 2.

17. A method of inhibiting the aggregation of blood platelets which comprises administering to a host in need of such inhibition a therapeutically effective amount of a compound of claim 3.

18. A method of inhibiting the aggregation of blood platelets which comprises administering to a host in need of such inhibition a therapeutically effective amount of a compound of claim 4.

19. A method of inhibiting the aggregation of blood platelets which comprises administering to a host in need of such inhibition a therapeutically effective amount of a compound of claim 5.

20. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a therapeutically effective amount of a compound of claim 1.

21. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a threapeutically effective amount of a compound of claim 2.

22. A method of treating thromboembolic disorders selected from thrombus or embolus formation, harmful platelet aggregation, reocclusion following thrombolysis, reperfusion injury, restenosis, atherosclerosis, stroke myocardial infarction, and unstable angina, which comprises administering to a host in need of such treatment a therapeutically effective amount of a compound of claim 3.

23. A method of treating thromboembolic disorders selected from thrombus or embolus formation, harmful platelet aggregation, reocclusion following thrombolysis, reperfusion injury, restenosis, atherosclerosis, stroke myocardial infarction, and unstable angina, which comprises administering to a host in need of such treatment a therapeutically effective amount of a compound of claim 4.

24. A method of treating thromboembolic disorders selected from thrombus or embolus formation, harmful platelet aggregation, reocclusion following thrombolysis, reperfusion injury, restenosis, atherosclerosis, stroke myocardial infarction, and unstable angina, which comprises administering to a host in need of such treatment a therapeutically effective amount of a compound of claim 5.

25. A pharmaceutical composition comprising a pharmaceutical carrier and a therapeutically effective amount of a compound of claim 6 or a pharmaceutically acceptable salt form thereof.

26. A pharmaceutical composition comprising a pharmaceutical carrier and a therapeutically effective amount of a compound of claim 7 or a pharmaceutically acceptable salt form thereof.

27. A pharmaceutical composition comprising a pharmaceutical carrier and a therapeutically effective amount of a compound of claim 8 or a pharmaceutically acceptable salt form thereof.

28. A pharmaceutical composition comprising a pharmaceutical carrier and a therapeutically effective amount of a compound of claim 9 or a pharmaceutically acceptable salt form thereof.

* * * * *